United States Patent [19]

Redmond et al.

[11] Patent Number: 5,298,244
[45] Date of Patent: Mar. 29, 1994

[54] ASSEMBLED VIRAL PARTICLES AND THEIR USE IN A VACCINE TO ROTAVIRAL DISEASE

[75] Inventors: Mark J. Redmond; Mohammed K. Ijaz; Michael D. Parker, all of Saskatoon, Canada

[73] Assignee: University of Saskatchewan, Saskatoon, Canada

[21] Appl. No.: 603,133

[22] Filed: Oct. 25, 1990

[51] Int. Cl.$^5$ .................... A61K 39/15; C07K 13/00; C12N 15/46

[52] U.S. Cl. .................................. 424/89; 424/88; 514/12; 530/350; 530/826; 536/23.72

[58] Field of Search ............... 424/82, 88, 89; 514/12; 530/350, 826

[56] References Cited

U.S. PATENT DOCUMENTS 5,071,651 12/1991 Sabara et al. .................. 424/89

FOREIGN PATENT DOCUMENTS 0259149 3/1988 European Pat. Off. .
0273366 7/1988 European Pat. Off. .

OTHER PUBLICATIONS

Ijaz et al., *J. Virol.* (1990) Pre-publication copy.
Flores et al., *J. Clin. Microbiol.* (1989) 27:512–518.
Estes et al., *Microbiol. Rev.* (1989) 53:410–449.
Sabara et al., *J. Virol.* (1985) 53:58–66.
Potter et al., *Nucl. Acid Res.* (1987) 15(10):4361.
Mackow et al., *Proc. Natl. Acad. Sci. USA* (1988) 85:645–649.
Offit et al., *J. Virol.* (1986) 58:700–703.
Redmond et al., *Mol. Immunol.* (1990) 28(3):269–278.
Ready et al., *Virology* (1988) 167:269–273.
Estes et al., *J. Virol.* (1987) 61(5):1488–1494.
Estes et al., *Nucl. Acids Res.* (1984) 12(4):1875–1887.
Ready et al., *Virology* (1987) 157:189–198.
Sabara et al., *J. Gen Virol.* (1987) 68:123–133.

Taniguchi et al., *J. Virol.* (1989) 63(9):4101–4106.
Bass et al., "NS35 and not VP7 is the soluble rotavirus protein which binds to target cells"*Journal of Virology* (1990) 64(1):322–330.
Chen et al., "Specific interactions between rotavirus outer capsid proteins VP4 and VP7 determine expression of a cross-reactive, neutralizing VP-4-specific epitope" *Journal of Virology* (1992) 66(1):432–439.
Ijaz et al., "Heterotypic passive protection induced by synthetic peptides corresponding to VP7 and VP4 of bovine rotavirus" *Journal of Virology* (1991) 65(6):3106–3113.
Redmond et al., "Rotavirus vaccinology" Kurstak, E., ed., *Control of Virus Diseases* (1992) Marcel Dekker, Inc., New York, Chapter 16, pp. 387–404.
Redmond et al., "Assembly of recombinant rotavirus proteins into virus-like particles and assessment of vaccine potential" *Vaccine* (1992) 11(2):273–281.
Redmond et al., "Rotavirus particles function as immunological carriers for the delivery of peptides from infectious agents and endogenous proteins" *Molecular Immunology* (1991) 28(3):269–278.
Brüssow et al.,, *J. Virol.* (1990) 64(8):3635–3642.
Biologizal Abstracts/RRM 41:19066.
Shendan, J. E. et al. "Prevention of Rotavirus–Induced Diarrhea in Neonatal Mice Born to Dams Immunized with Empty Capsids of Simian Rotavirus SA-11", J. Infect. Diseasses 149 (3) 434–438 (Mar. 1984).

*Primary Examiner*—Robert A. Wax
*Assistant Examiner*—Rebeeca Prouty
*Attorney, Agent or Firm*—Morrison & Forrester

[57] ABSTRACT

Assembled viral particles derived from rotavirus proteins are disclosed. The assembled particles include the inner capsid protein, VP6, in combination with either or both of the outer capsid proteins, VP4 and VP7. These assemblies can be used in vaccine compositions for the treatment and prevention of rotaviral disease.

8 Claims, 55 Drawing Sheets

Sequence Range: 1 to 1356

```
                10                  20                  30                  40
                 *                   *                   *                   *
GG CTT TTA AAC GAA GTC TTC AAC ATG GAT GTC CTG TAC TCC TTG
CC GAA AAT TTG CTT CAG AAG TTG TAC CTA CAG GAC ATG AGG AAC
                                Met Asp Val Leu Tyr Ser Leu>

50                  60                  70                  80
                 *                   *                   *                   *
TCA AAA ACT CTT AAA GAT GCT AGA GAC AAA ATT GTC GAA GGC ACA
AGT TTT TGA GAA TTT CTA CGA TCT CTG TTT TAA CAG CTT CCG TGT
Ser Lys Thr Leu Lys Asp Ala Arg Asp Lys Ile Val Glu Gly Thr>

90                 100                 110                 120                 130
                 *                   *                   *                   *                   *
TTA TAC TCC AAT GTA AGT TCA CAT GAT CTA ATT CAA CAA TTT AAA ATG
AAT ATG AGG TTA CAT TCA AGT GTA CTA GAT TAA GTT GTT AAA TTT TAC
Leu Tyr Ser Asn Val Ser His Asp Leu Ile Gln Gln Phe Asn Gln Met>

140                 150                 160                 170
                 *                   *                   *                   *
ATA ATT ACT ATG AAT GGA AAT GAG TTC CAA ACT GGA GGA ATT GGT
TAT TAA TGA TAC TTA CCT TTA CTC AAG GTT TGA CCT CCT TAA CCA
Ile Ile Thr Met Asn Gly Asn Glu Phe Gln Thr Gly Gly Ile Gly>

180                 190                 200                 210                 220
                 *                   *                   *                   *                   *
AAT CTA CCG ATT AGA AAT TGG AAT TTT GAT TTT AAA CTA CTT GAA CCT
TTA GAT GGC TAA TCT TTA ACC TTA AAA CTA AAA TTT GAT GAA CTT GGA
Asn Leu Pro Ile Arg Asn Trp Asn Phe Asp Phe Lys Leu Leu Gly>
```

Fig. 1A

```
230         240         250         260
 *           *           *           *
ACA ACT CTA AAT TTA GAT GCT CTA AAT TAC GTC GAA ACG GCC CGC
TGT TGA GAT GAT TTA AAT CTA CGA TTG CAG ATG TGC CGG GCG
Thr Thr Leu Leu Asn Leu Asp Ala Asn Tyr Val Glu Thr Ala Arg>

270         280         290         300         310
 *           *           *           *           *
AAT ACA AAT GAT TAT TTT GTA GAT TTT GTA GAT AAT GTA TGT ATG
TTA TGT TTA CTA ATA AAA CAT CTA AAA CAT CTA TTA CAT ACA TAC
Asn Thr Asn Asp Tyr Phe Val Asp Phe Val Asp Asn Val Cys Met>

320         330         340         350
 *           *           *           *
GAC GAA ATG GTT AGA GAA TCA CAA AGA AAT GGA ATT GCA CCA CAA
CTG CTT TAC CAA TCT CTT AGT GTT TCT TTA CCT TAA CGT GGT GTT
Asp Glu Met Val Arg Glu Ser Gln Arg Asn Gly Ile Ala Pro Gln>

360         370         380         390         400
 *           *           *           *           *
TCA GAT TCA CTT ATA AAG TTA TCA GGC ATT CCG ATT AAA TTT AAA AGA ATA
AGT CTA AGT GAA TTC AAT AGT CCG TAA CGT TAA TTT AAA TTT TCT TAT
Ser Asp Ser Leu Ile Lys Leu Ser Gly Ile Pro Ile Lys Phe Lys Arg Ile>

410         420         430         440
 *           *           *           *
AAT TTT GAC AAT TCA TCA GAA TAC ATA GAG AAC TGG AAT TTG CCA
TTA AAA CTG TTA AGT AGT CTT ATG CTC TTG ACC TTA AAC GGT
Asn Phe Asp Asn Ser Ser Glu Tyr Ile Glu Asn Trp Asn Leu Pro>
```

Fig. 1B

```
450         460         470         480         490
 *           *           *           *           *
AAT AGA AGA ACG GGT CAA AGA ACG TTT CAT AAA CCA AAC ATT
TTA TCT TCT TGC CCA GTT TCT TGC AAA GTA TTT GGT TTG TAA
Asn Arg Arg Thr Gly Gln Arg Cys Phe His Lys Pro Asn Ile>

500         510         520         530
             *           *           *           *
TTC CCT TAT TCA GCT TCA TTC ACG AAC AGA TCA CAA CCT TCT
AAG GGA ATA AGT CGA AGT AAG TGC TTG TCT AGT GTT GGA AGA
Phe Pro Tyr Ser Ala Ser Phe Thr Asn Arg Ser Gln Pro Ser>

540         550         560         570         580
 *           *           *           *           *
CAT GAT AAC TTG ATG GGT ACG ATG CTC AAT GCG GGA TCA GAA
GTA CTA TTG AAC TAC CCA TGC TAC GAG TTA CGC CCT AGT CTT
His Asp Asn Leu Met Gly Thr Met Trp Leu Asn Ala Gly Ser Glu>

590         600         610         620
             *           *           *           *
ATT CAG GTC GCT GGA TTC AAG TAC TCA TGT GCA ATA AAC GCG CCA
TAA GTC CAG CGA CCT AAG TTC ATG AGT ACA CGT TAT TTG CGC GGT
Ile Gln Val Ala Gly Phe Asp Tyr Ser Cys Ala Ile Asn Ala Pro>

630         640         650         660         670
 *           *           *           *           *
GCT AAT ACG CAA CAA TTT GAG CAT ATT GTA CAG CTT CGA AGG GTG
CGA TTA TGC GTT GTT AAA CTC GTA TAA CAT GTC GAA GCT TCC CAC
Ala Asn Thr Gln Gln Phe Glu His Ile Val Gln Leu Arg Arg Val>
```

Fig. 1C

```
680            690            700            710
 *              *              *              *
TTG ACT ACA GCT ACA ATA ACT CTT TTA CCA GAT GCA GAA AGA TTT
AAC TGA TGT CGA TGT TAT TGA GAA AAT GGT CTA CGT CTT TCT AAA
Leu Thr Thr Ala Thr Ile Thr Leu Leu Pro Asp Ala Glu Arg Phe>

720            730            740            750            760
 *              *              *              *              *
AGT TTT CCA AGA GTG ATT ACT TCA GCT GAC GGA GCG ACT ACA TGG
TCA AAA GGT TCT CAC TAA TGA AGT CGA CTG CCT CGC TGA TGT ACC
Ser Phe Pro Arg Val Ile Thr Ser Ala Asp Gly Ala Thr Thr Trp>

770            780            790            800
 *              *              *              *
TAC TTC AAT CCA GTG ATT CTT AGA TCT CCA AAT AAC GTT GAA ATA GAG
ATG AAG GTT AGT CAC TAA GAA TCT AGA GGT TTA TTG CAA CTT TAT CTC
Tyr Phe Asn Pro Val Ile Leu Arg Ser Pro Asn Asn Val Glu Ile Glu>

810            820            830            840            850
 *              *              *              *              *
TTT CTA CTA AAC GGG CAG ATA ATA AAT ACT TAC CAA GCA AGA TTT
AAA GAT GAT TTG CCC GTC TAT TAT TTA TGA ATG GTT CGT TCT AAA
Phe Leu Leu Asn Gly Gln Ile Ile Asn Thr Tyr Gln Ala Arg Phe>

860            870            880            890
 *              *              *              *
GGA ACC ATC ATA GCT AGA AAT TTT GAT ACA ATT AGA TTG TCA TTT
CCT TGG TAG TAT CGA TCT TTA AAA CTA TGT TAA TCT AAC AGT AAA
Gly Thr Ile Ile Ala Arg Asn Phe Asp Thr Ile Arg Leu Ser Phe>
```

Fig. 1D

```
900         910         920         930         940
 *           *           *           *           *
CAG TTG ATG AGA CCA CCA AAT ATG ACA CCA GCG GTA GCG GCG TTA
GTC AAC TAC TCT GGT GGT TTA TAC TGT GGT CGC CAT CGC CGC AAT
Gln Leu Met Arg Pro Pro Asn Met Thr Pro Ala Val Ala Ala Leu>

950         960         970         980
 *           *           *           *
TTT CCA AAT GCG CAG CCA TTT GAA CAT CAC GCA ACA GTA GGA CTC
AAA GGT TTA CGC GTC GGT AAA CTT GTA GTG CGT TGT CAT CCT GAG
Phe Pro Asn Ala Gln Pro Phe Glu His Ala Thr Val Gly Leu>

990         1000        1010        1020        1030
 *           *           *           *           *
ACG CTT AGA ATT GAA TCT GCA GTT TGT GAA TCA GTA CTT GCC GAC
TGC GAA TCT TAA CTT AGA CGT CAA ACA CTT AGT CAT GAA CGG CTG
Thr Leu Arg Ile Glu Ser Ala Val Cys Glu Ser Val Leu Ala Asp>

1040        1050        1060        1070
 *           *           *           *
GCA AGC GAA ACA ATG CTA GCA AAT GTG ACA TCT GTT AGA CAA GAA
CGT TCG CTT TGT TAC GAT CGT TTA CAC TGT AGA TCT GTT CTT
Ala Ser Glu Thr Met Leu Ala Asn Val Thr Ser Val Arg Gln Glu>

1080        1090        1100        1110        1120
 *           *           *           *           *
TAC GCG ATA CCA GTT GGA CCA GTT TTT CCA CCA GGT ATG AAT TGG
ATG CGC TAT GGT CAA CCT GGT CAA AAA GGT CCA TAC TTA ACC
Tyr Ala Ile Pro Val Gly Pro Val Phe Pro Pro Gly Met Asn Trp>
```

Fig.1E

```
        1130            1140            1150            1160
          *               *               *               *
ACT GAT TTG ATC ACT AAC TAT TCA CCA TCT AGA GAG GAT AAC TTG
TGA CTA AAC TAG TGA TTG ATA AGT GGT AGA TCT CTC CTA TTG AAC
Thr Asp Leu Ile Thr Asn Tyr Ser Pro Ser Arg Glu Asp Asn Leu>

1170            1180            1190            1200            1210
      *               *               *               *               *
CAG CGT GTA TTT ACA GTG GCT TCC ATT AGA AGC ATG CTT GTC AAA
GTC GCA CAT AAA TGT CAC CGA AGG TAA TCT TCG TAC GAA CAG TTT
Gln Arg Val Phe Thr Val Ala Ser Ile Arg Ser Met Leu Val Lys>

1220            1230            1240            1250
          *               *               *               *
TGA GGA CCA AGC TAA CCA CTT GGT ATC CGA CTT TGG TGA GTA TGT
ACT CCT GGT TCG ATT GGT GAA CCA TAG GCT GAA ACC ACT CAT ACA 1260            1270            1280            1290            1300
      *               *               *               *               *
AGC TAC GTC AAG CTG TTT GAA CTC TGT AAG TAA GGA TGC GTC TAC
TCG ATG CAG TTC GAC AAA CTT GAG ACA TTC ATT CCT ACG CAG ATG 1310            1320            1330            1340
          *               *               *               *
GTA TTC GCT ACA CAG AGT AAT CAC TCA GAT GGC GTA GTG AGA GGA
CAT AAG CGA TGT GTC TCA TTA GTG AGT CTA CCG CAT CAC TCT CCT

1350
      *
TGT GAC C
ACA CTG G
```

Fig. 1F

```
Sequence Range: 1 to 451

10         20         30         40         50
                      *          *          *          *          *
Translatio  LLNEV FNMDV LYSLS KTLKD ARDKI VEGTL YSNVS DLIQQ FNQMI ITMNG ROBMCP         15    30    45    60    75    90   105   120   135   150
[ 2164 ]    LLNEV FNMDV LYSLS KTLKD ARDKI VEGTL YSNVS DLIQQ FNQMI ITMNG>
            ^^^^^ ^^^^^ ^^^^^ ^^^^^ ^^^^^ ^^^^^ ^^^^^ ^^^^^ ^^^^^ ^^^^^

RO1HVP6        15    30    45    60    75    90   105   120   135   150
[ 2061 ]    LLNEV FNMDV LYSLS KTLKD ARDKI VEGTL YSNVS DLIQQ FNQMI ITMNG>
            ^^^^^ ^^^^^ ^^^^^ ^^^^^ ^^^^^ ^^^^^ ^^^^^ ^^^^^ ^^^^^ ^^^^^

RO1VVP6H2      15    30    45    60    75    90   105   120   135   150
[ 1997 ]    LLNEV FNMDV LYSLS KTLKD ARDKI VEGTL YSNVS DLIQQ FNQMv ITMNG>
            ^^^^^ ^^^^^ ^^^^^ ^^^^^ ^^^^^ ^^^^^ ^^^^^ ^^^^^ ^^^^^ ^^^^^

RO1VVP6FI      15    30    45    60    75    90   105   120   135   150
[ 1974 ]    LLNEV FNMeV LYSiS KTLKD ARDKI VEGTL YSNVS DiIQQ FNQiI vTMNG>
            ^^^^^ ^^^^^ ^^^^^ ^^^^^ ^^^^^ ^^^^^ ^^^^^ ^^^^^ ^^^^^ ^^^^^

RO1PVP6        15    30    45    60    75    90   105   120   135   150
[ 1949 ]    LLNEV FNMeV LYSLS KTLKD ARDKI VEGTL YSNVS DLIQQ FNQMI vTMNG>
            ^^^^^ ^^^^^ ^^^^^ ^^^^^ ^^^^^ ^^^^^ ^^^^^ ^^^^^ ^^^^^ ^^^^^

RO2SEG6        15    30    45    60    75    90   105   120   135   150
[ 1939 ]    L*NEV FdMeV LYSLS KTLKD ARDKI VEGTL YSNVS DLIQQ FNQMI vTMNG>
            ^v^^^ ^^^^^ ^^^^^ ^^^^^ ^^^^^ ^^^^^ ^^^^^ ^^^^^ ^^^^^ ^^^^^

PRVVP6               25    40    55    70    85   100   115   130   145
[  904 ]          FtMDV LfSia KTvsD lkkKv VvGTi YtNVe DiIQQ tNelI rTlNG>
                  ^ ^^^ ^^^^  ^^^ ^ v^ ^^ ^v^^^ ^ ^^  ^^^^^ v^^^^ v^^^^
```

Fig. 2A

|  |  | 60 | 70 | 80 | 90 | 100 |
|---|---|---|---|---|---|---|
|  |  | * | * | * | * | * |
| Translatio |  | NEFQT GGIGN LPIRN WNFDF | GLLGT TLLNL | DANYV ETARN | TNDYF VDFVD |  |
| ROBMCP<br>[ 2164 ] | 165 | 180 195 210 | 225 240 | 255 270 | 285 300 |  |
|  | NEFQT GGIGN LPIRN WNFDF | GLLGT TLLNL | DANYV ETARN | TiDYF VDFVD> |  |
| RO1HVP6<br>[ 2061 ] | 165 | 180 195 210 | 225 240 | 255 270 | 285 300 |  |
|  | NEFQT GGIGN LPIRN WNFDF | GLLGT TLLNL | DANYV ETARN | TiDYF VDFVD> |  |
| RO1VVP6H2<br>[ 1997 ] | 165 | 180 195 210 | 225 240 | 255 270 | 285 300 |  |
|  | NEFQT GGIGt LPIRN WtFDF | GLLGT TLLNL | DANYV ETARt | TieYF iDFiD> |  |
| RO1VVP6FI<br>[ 1974 ] | 165 | 180 195 210 | 225 240 | 255 270 | 285 300 |  |
|  | NEFQT GGIGN LPvRN WtFDF | GLLGT TLLNL | DANYV ETARt | TieYF iDFiD> |  |
| RO1PVP6<br>[ 1949 ] | 165 | 180 195 210 | 225 240 | 255 270 | 285 300 |  |
|  | NdFQT GGIGN LPIRN WNFDF | GLLGT TLLNL | DANYV ETARN | TieYF iDFiD> |  |
| RO2SEG6<br>[ 1939 ] | 165 | 180 195 210 | 225 240 | 255 270 | 285 300 |  |
|  | NdFQT GGIGN LPvRN WtFDF | GLLGT TLLNL | DANYV EnArt | iieYF iDFiD> |  |
| PRVVP6<br>[ 904 ] | 160 | 175 190 205 | 220 235 | 250 265 | 280 295 |  |
|  | NtFhT GGIGt qPqke WNFql | pqLGT TLLNL | DdNYV qatRs | viDYl asFie> |  |

Fig. 2B

```
                        110         120         130         140         150
                          *           *           *           *           *
Translatio  NVCMD EMVRE SQRNG IAPQS DSLIK LSGIK FKRIN FDNSS EYIEN WNLPN ROBMCP        315   330   345   360   375   390   405   420   435   450
[ 2164 ]    NVCMD EMVRE SQRNG IAPQS DSLIK LSGIK FKRIN FDNSS EYIEN WNLPN>
            ^^^^^ ^^^^^ ^^^^^ ^^^^^ ^^^^^ ^^^^^ ^^^^^ ^^^^^ ^^^^^ ^^^^^

RO1HVP6       315   330   345   360   375   390   405   420   435   450
[ 2061 ]    NVCMD EMVRE SQRNG IAPQS DSLrK LSGIK FKRIN FDNSS EYIEN WNLqN>
            ^^^^^ ^^^^^ ^^^^^ ^^^^^ ^^^v^ ^^^^^ ^^^^^ ^^^^^ ^^^^^ ^^^ ^

RO1VVP6H2     315   330   345   360   375   390   405   420   435   450
[ 1997 ]    NVCMD EMVRE SQRNG IAPQS DSLrK LSGIK FKRIN FDNSS EYIEN WNLqN>
            ^^^^^ ^^^^^ ^^^^^ ^^^^^ ^^^v^ ^^^^^ ^^^^^ ^^^^^ ^^^^^ ^^^ ^

RO1VVP6FI     315   330   345   360   375   390   405   420   435   450
[ 1974 ]    NVCMD EMtRE SQRNG IAPQS DaLrK LSGIK FKRIN FDNSS EYIEN WNLqN>
            ^^^^^ ^^ ^^ ^^^^^ ^^^^^ ^ ^v^ ^^^^^ ^^^^^ ^^^^^ ^^^^^ ^^^ ^

RO1PVP6       315   330   345   360   375   390   405   420   435   450
[ 1949 ]    NVCMD EMaRE SQRNG IAPQS eafrK LaGIK FKRIN FDNSS EYIEN WNLqN>
            ^^^^^ ^^ ^^ ^^^^^ ^^^^^ ^ ^v^ ^ ^^^ ^^^^^ ^^^^^ ^^^^^ ^^^ ^

RO2SEG6       315   330   345   360   375   390   405   420   435   450
[ 1939 ]    NVCMD EMaRE SQRNG vAPQS eaLrK LaGIK FKRIN FDNSS EYIEN WNLqN>
            ^^^^^ ^^ ^^ ^^^^^ ^^^^^ ^ ^v^ ^ ^^^ ^^^^^ ^^^^^ ^^^^^ ^^^ ^

PRVVP6        310   325   340   355   370   385   400   415   430   445
[  904 ]    aVCdD EiVRE asRNG mqPQS ptLIa LassK FKtIN FnNSS qsIkN Ws-aq>
             ^^v^ ^^^^^   ^^^ ^ ^^^   ^^  ^   ^ ^^ ^^ ^^^^^ ^v^ ^ ^
```

Fig. 2C

```
ROlVVP6H2.                     135        150        165        180        195
[  40 ]                       K  Lk-l-  FKRdv  Frkrt  sklEN  rkL>
                                 ^  ^   ^^^vv  v  ^   ^ ^    ^

160        170        180        190        200
                                  *          *          *          *          *
Translatio    RRQRT  GFTFH  KPNIF  PYSAS  FTLNR  SQPSH  DNLMG  TMWLN  AGSEI  QVAGF ROBMCP         465    480    495    510    525    540    555    570    585    600
[ 2164 ]      RRQRT  GFTFH  KPNIF  PYSAS  FTLNR  SQPaH  DNLMG  TMWLN  AGSEI  QVAGF>
              ^^^^^  ^^^^^  ^^^^^  ^^^^^  ^^^^^  ^^^^^  ^^^^^  ^^^^^  ^^^^^  ^^^^^

RO1HVP6        465    480    495    510    525    540    555    570    585    600
[ 2061 ]      RRQRT  GFTFH  KPNIF  PYSAS  FTLNR  SQPaH  DNLMG  TMWLN  AGSEI  QVAGF>
              ^^^^^  ^^^^^  ^^^^^  ^^^^^  ^^^^^  ^^^^^  ^^^^^  ^^^^^  ^^^^^  ^^^^^

RO1VVP6H2      465    480    495    510    525    540    555    570    585    600
[ 1997 ]      RRQRk  GFTFH  KPNIF  PYSAS  FTLNR  SQPaH  DNLMG  TMWLN  AGSEI  QVAGF>
              ^^^^^  ^^^^^  ^^^^^  ^^^^^  ^^^^^  ^^^^^  ^^^^^  ^^^^^  ^^^^^  ^^^^^

RO1VVP6FI      465    480    495    510    525    540    555    570    585    600
[ 1974 ]      RRQRT  GFTFH  KPNIF  PYSAS  FTLNR  SQPlH  ndLMG  TMWLN  AGSEI  QVAGF>
              ^^^^^  ^^^^^  ^^^^^  ^^^^^  ^^^^^  ^^^^v  ^ ^    ^^^^^  ^^^^^  ^^^^^

RO1PVP6        465    480    495    510    525    540    555    570    585    600
[ 1949 ]      RRQRT  GFiFH  KPNIF  PYSAS  FTLNR  SQPmH  DNLMG  TMWLN  AGSEI  QVAGF>
              ^^^^^  ^^ ^   ^^^^^  ^^^^^  ^^^^^  ^^^v^  ^^^^^  ^^^^^  ^^^^^  ^^^^^

RO2SEG6        465    480    495    510    525    540    555    570    585    600
[ 1939 ]      RRQRT  GFvFH  KPNIF  PYSAS  FTLNR  SQPmH  DNLMG  TMWLN  AGSEI  QVAGF>
              ^^^^^  ^^ ^   ^^^^^  ^^^^^  ^^^^^  ^^^v^  ^^^^^  ^^^^^  ^^^^^  ^^^^^
```

Fig. 2D

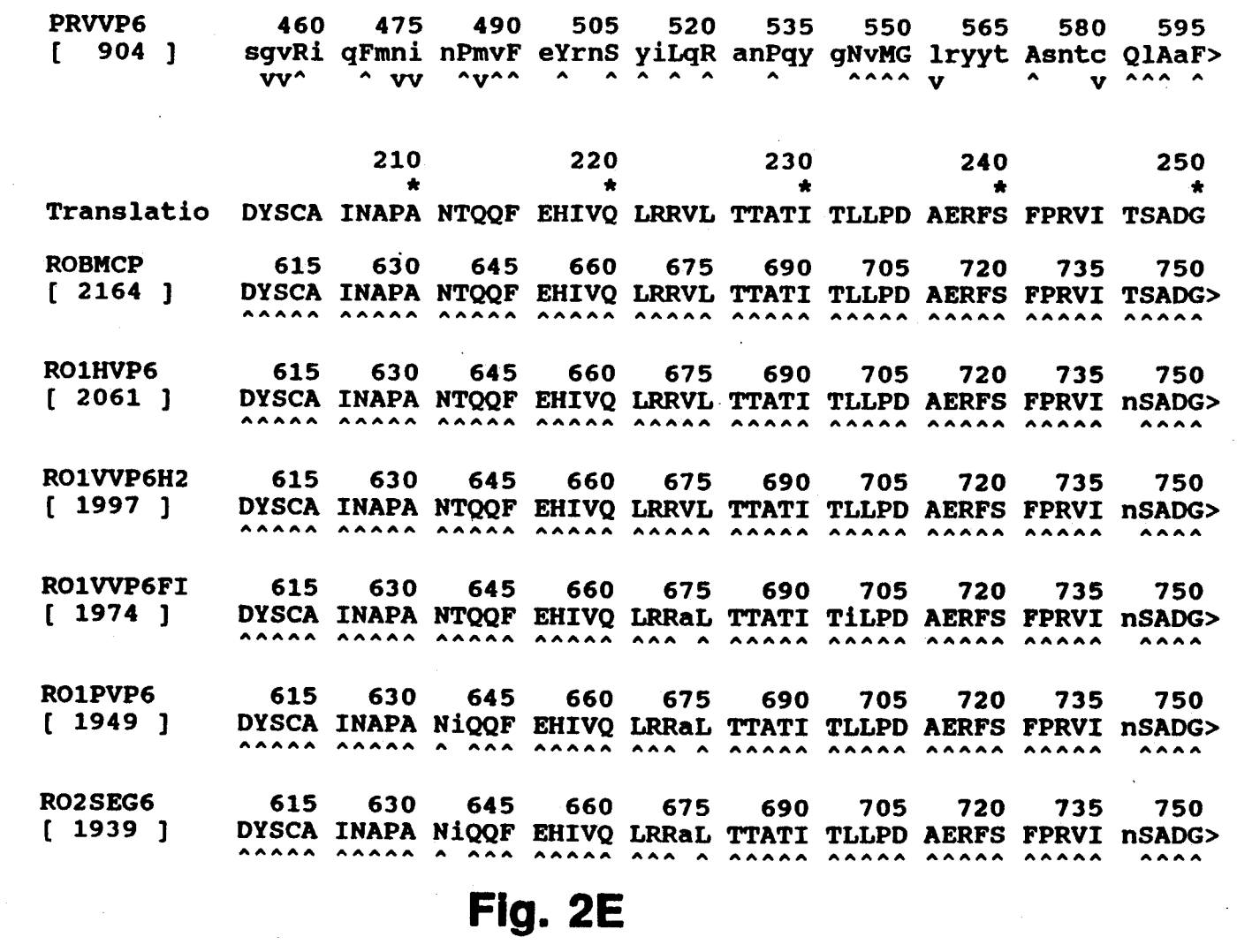

| | 460 | 475 | 490 | 505 | 520 | 535 | 550 | 565 | 580 | 595 |
|---|---|---|---|---|---|---|---|---|---|---|
| PRVVP6 [ 904 ] | sgvRi ^v^ | qFmni ^ vv | nPmvF ^v^^ | eYrnS ^ | yiLqR ^ ^ | anPqy ^ | gNvMG v | lryyt v | Asntc ^ | QlAaF> ^^^ |

| | | | | | 210 | 220 | 230 | 240 | 250 | |

```
PRVVP6         610       625       640       655       670       685       700       715       730       745
[ 904 ]        DstlA eNAPn NTQrF iyngr LkRpi snvlm kieag Apnin nltil pdptn>
               ^v v^      ^^^      ^v^         v       v^    ^v        v^    vv ^^

Translatio     260       270       280       290       300
                 *         *         *         *         *
               ATTWY FNPVI LRPNN VEIEF LLNGQ IINTY QARFG TIIAR NFDTI RLSFQ ROBMCP         765       780       795       810       825       840       855       870       885       900
[ 2164 ]       ATTWY FNPVI LRPNN VEIEF LLNGQ IINTY QARFG TIIAR NFDTI RLSFQ>
               ^^^^^ ^^^^^ ^^^^^ ^^^^^ ^^^^^ ^^^^^ ^^^^^ ^^^^^ ^^^^^ ^^^^^

RO1HVP6        765       780       795       810       825       840       855       870       885       900
[ 2061 ]       ATTWY FNPVI LRPNN VEVEF LLNGQ IINTY QARFG TIIAR NFDTI RLSFQ>
               ^^^^^ ^^^^^ ^^^^^ ^^^^^ ^^^^^ ^^^^^ ^^^^^ ^^^^^ ^^^^^ ^^^^^

RO1VVP6H2      765       780       795       810       825       840       855       870       885       900
[ 1997 ]       tTTWY FNPVI fRPNN VEIEF LLNGQ IINnY QARFG TIIAR NFDTI RLSFQ>
               ^^^^^ ^^^^^ ^^^^^ ^^^^^ ^^^^^ ^^^^^ ^^^^^ ^^^^^ ^^^^^ ^^^^^

RO1VVP6FI      765       780       795       810       825       840       855       870       885       900
[ 1974 ]       ATTWf FNPVI LRPNN VEVEF LLNGQ IINTY QARFG TIIAR NFDTI RLSFQ>
               ^^^^^ ^^^^^ ^^^^^ ^^^^^ ^^^^^ ^^^^^ ^^^^^ ^^^^^ ^^^^^ ^^^^^

RO1PVP6        765       780       795       810       825       840       855       870       885       900
[ 1949 ]       ATTWf FNPVI LRPNN VEVEF LLNGQ IINTY QARFG TIVAR NFDTI RLSFQ>
               ^^^^^ ^^^^^ ^^^^^ ^^^^^ ^^^^^ ^^^^^ ^^^^^ ^^^^^ ^^^^^ ^^^^^

RO2SEG6        765       780       795       810       825       840       855       870       885       900
[ 1939 ]       ATTWf FNPVI LRPNN VEVEF LLNGQ IINTY QARFG TIIAR NFDaI RL1FQ>
               ^^^^^ ^^^^^ ^^^^^ ^^^^^ ^^^^^ ^^^^^ ^^^^^ ^^^^^ ^^^^^ ^^v^^
```

Fig. 2F

```
PRVVP6          760   775   790   805   820   835     850   865   880
[  904 ]      qTTWl yNPdq Lmngt ftIEF ynNGQ lvdmv r-nmG vvtvR tFDsy Ritid>
               ^^^  ^^^vv ^       ^^^ v^^^  ^^^ v     ^   ^   ^  ^^    ^^  ^

310         320               330         340         350
                        *           *                 *           *           *
Translatio    LMRPP NMTPA VAALF PNAQP FEHHA TVGLT LRIES AVCES VLADA SETML ROBMCP          915   930   945   960   975   990  1005  1020  1035  1050
[ 2164 ]      LMRPP NMTPA VAALF PNAQP FEHHA TVGLT LRIES AVCES VLADA SETML>
              ^^^^^ ^^^^^ ^^^^^ ^^^^^ ^^^^^ ^^^^^ ^^^^^ ^^^^^ ^^^^^ ^^^^^

RO1HVP6         915   930   945   960   975   990  1005  1020  1035  1050
[ 2061 ]      LMRPP NMTPt VAALF PNAQP FEHHA TVGLT LRIES AVCES VLADA SETML>
              ^^^^^ ^^^^  ^^^^^ ^^^^^ ^^^^^ ^^^^^ ^^^^^ ^^^^^ ^^^^^ ^^^^^ pp
               |
RO1VVP6H2      |      930   945   960   975   990  1005  1020  1035  1050
[ 1997 ]      LMRPq NMTPA VAALF PNApP FEHHA TVGLT LRIES AiCES VLADA SETML>
              ^^^^  ^^^^^ ^^^^^ ^^^ ^ ^^^^^ ^^^^^ ^^^^^ ^^^^^ ^^^^^ ^^^^^

RO1VVP6FI       915   930   945   960   975   990  1005  1020  1035  1050
[ 1974 ]      LMRPP NMTPA VnALF PqAQP FqHHA TVGLT LRIdS AVCES VLADs nETML>
              ^^^^^ ^^^^^ ^ ^^^ ^ ^^^ ^^^^^ ^^^^^ ^^^^^ ^^^^^ ^^^^   ^^^^

RO1PVP6         915   930   945   960   975   990  1005  1020  1035  1050
[ 1949 ]      LMRPP NMTPA VdALF PqAQP FqHHA TVGLT LRIES AVCES VLADA nETlL>
              ^^^^^ ^^^^^ ^ ^^^ ^ ^^^ ^^^^^ ^^^^^ ^^^^^ ^^^^^ ^^^^^  ^^^^
```

Fig. 2G

```
RO2SEG6       915   930   945   960   975   990  1005  1020  1035  1050
[ 1939 ]     LMRPP NMTPA VnALF PqAQP FqHHA TVGLT LRIES AVCES VLADA nETlL>
             ^^^^^ ^^^^^ ^ ^^^ ^ ^^^ ^^^^^ ^^^^^ ^^^^^ ^^^^^ ^^^^^  ^^^^

PRVVP6     895   910   925   940   955   970   985  1000  1015  1030
[  904 ]     miRPa aMTqy VqrLF PqggP ypyqA aymLT LsIld AttES VLcDs hsvdy>
             ^^^^    ^^ v ^ v^^ ^    ^ ^   ^^  vv^^ ^ ^v  ^ v^^ ^^v^     v 360         370         380         390         400
                      *           *           *           *           *
Translatio   ANVTS VRQEY AIPVG PVFPP GMNWT DLITN YSPSR EDNLQ RVFTV ASIRS ROBMCP        1065  1080  1095  1110  1125  1140  1155  1170  1185  1200
[ 2164 ]     ANVTS VRQEY AIPVG PVFPP GMNWT DLITN YSPSR EDNLQ RVFTV ASIRS>
             ^^^^^ ^^^^^ ^^^^^ ^^^^^ ^^^^^ ^^^^^ ^^^^^ ^^^^^ ^^^^^ ^^^^^

RO1HVP6       1065  1080  1095  1110  1125  1140  1155  1170  1185  1200
[ 2061 ]     ANVTS VRQEY AIPVG PVFPP GMNWT DLITN YSPSR EDNLQ RVFTV ASIRS>
             ^^^^^ ^^^^^ ^^^^^ ^^^^^ ^^^^^ ^^^^^ ^^^^^ ^^^^^ ^^^^^ ^^^^^

RO1VVP6H2  1065  1080  1095  1110  1125  1140  1155  1170  1185  1200
[ 1997 ]     ANVTS VRQEY AvPVG PVFPP GMNWT DLITN YSPSR EDNLQ RVFTV ASIRS>
             ^^^^^ ^^^^^ ^^^^^ ^^^^^ ^^^^^ ^^^^^ ^^^^^ ^^^^^ ^^^^^ ^^^^^

RO1VVP6FI     1065  1080  1095  1110  1125  1140  1155  1170  1185  1200
[ 1974 ]     ANVTa VRQEY AvPVG PVFPP GMNWT eLITN YSPSR EDNLQ RVFTV ASIRS>
             ^^^^  ^^^^^ ^^^^^ ^^^^^ ^^^^^ ^^^^^ ^^^^^ ^^^^^ ^^^^^ ^^^^^

RO1PVP6       1065  1080  1095  1110  1125  1140  1155  1170  1185  1200
[ 1949 ]     ANVTa VRQEY AIPVG PVFPP GMNWT eLITN YSPSR EDNLQ RVFTV ASIRS>
             ^^^^  ^^^^^ ^^^^^ ^^^^^ ^^^^^ ^^^^^ ^^^^^ ^^^^^ ^^^^^ ^^^^^
```

Fig. 2H

```
RO2SEG6        1065 1080 1095 1110 1125 1140 1155 1170 1185 1200
[ 1939 ]       ANVTa VRQEY AIPVG PVFPP GMNWT eLITN YSPSR EDNLQ RVFTV ASIRS>
               ^^^^  ^^^^^ ^^^^^ ^^^^^ ^^^^^ ^^^^^ ^^^^^ ^^^^^ ^^^^^ ^^^^^

PRVVP6         045 1060 1075 1090 1105 1120 1135 1150 1165 1180
[ 904 ]        siVan wRrds AmPaG tVFqP GfpWe qtlsN Ytvaq EDNLe RlllV ASvkr>
               v^    ^v    ^^^   ^     ^     ^v^   ^^^^^ ^^^^v ^^^^^ ^^^^^

410   420   430   440   450
                     *     *     *     *     *
Translatio     MLVK* GPS*P LGIRL W*VCS YVKLF ELCK* GCVYV FATQS NHSDG VVRGC ROBMCP         1215 1230 1245 1260 1275 1290 1305 1320 1335 1350
[ 2164 ]       MLVK* GPS*P LGIRL W*VCS YVKLF ELCK* GCVYV FATQS NHSDG VVRGC>
               ^^^^^ ^^^^^ ^^^^^ ^^^^^ ^^^^^ ^^^^^ ^^^^^ ^^^^^ ^^^^^ ^^^^^

RO1HVP6        1215 1230 1245 1260 1275 1290 1305 1320 1335
[ 2061 ]       MLiK* GPS*l LGIRt l*aCS YVKLF ELCK* GCiYt FATQS NHfnd Vkk>
               ^^^^^ ^^^^v ^^^^v vv    ^^^^^ ^^^^^ ^^^^v ^^^^^ ^^v^^ ^v^

RO1VVP6H2      1215 1230 1245 1260 1275 1290 1305 1320 1335 1350
[ 1997 ]       MLiK* rPd*q sGIRf ylaCS YiKLy rLCK* GyiYi FtTQS NctDG ikk>
               ^^^^^ v^  v v^^^^ ^^^^^ ^v^^v ^^^^^ ^v^^v ^v^^^ ^v^v^ ^v^

RO1VVP6FI      1215 1230 1245 1260 1275 1290 1305 1320 1335
[ 1974 ]       MLiK* GPS*l LGIlv **VCS YVKLl ELCK* ehVhV FvpQS NHSDG ikk>
               ^^^^^ ^^^^v ^^^vv vv^^^ ^^^^v ^^^^^ v^  v v^  ^ ^^^^^ ^v^

RO1PVP6        1215 1230 1245 1260 1275 1290 1305 1320 1335
[ 1949 ]       MLiK* GPd*t sGIqp llaCS YiksF rLCK* Ghdfi FAT*s Nclnd Vkk>
               ^^^^^ ^^v^v v^^vv ^v^^^ ^v^vv ^^^^^ ^v^v^ ^^^ ^ ^v^^^ ^v^
```

Fig. 21

```
RO2SEG6       1215 1230 1245 1260 1275 1290 1305 1320 1335 1350
[ 1939 ]     MLiK* GPd*a sGIqs *lacS YiKsF rLfK* Ghdfm FAT*S NcInd VVRGC>
             ^^^^^  ^^ ^  ^^^   ^^ ^ ^^^^  ^^^^  ^^^^  ^^^^^ ^^^^  ^^^^^

PRVVP6        195
[  904 ]     Mvm>
             ^^^

Translatio    D

ROBMCP        D>
[ 2164 ]     ^

RO2SEG6       D>
[ 1939 ]     ^
```

Fig. 2J

Sequence Range: 1 to 776

```
                  10         20         30         40         50
                   *          *          *          *          *
C486G4p      MASLI YRQLL TNSYT VELSD EIQEI GSTKT QNVTV NPGPF AQTNY ASVNW
              5         15         25         35         45
SA11G4p      MAaLI YRQLL TNSYT VELSD EIQEI GSTKT QNVTV NPGPF AQTNY ApVNW>
[ 3506 ]      ^^         ^^^^^ ^^^^^ ^^^^^ ^^^^^ ^^^^^ ^^^^^ ^  ^
              5         15         25         35         45         50
RRVVP4p      MASLI YRQLL TNSYT VdLSD EIQEI GSTKT QNVTi NlGPF AQTgY ApVNW>
[ 3198 ]      ^^^^^ ^^^^^ ^^^^^ ^ ^^^ ^^^^^ ^^^^^ ^^^^  ^ ^^^ ^^^ Y
              5         15         25         35         45         50
DS-1p        MASLI YRQLL TNSYs VdLhD EIeqI GSeKT QsVTV NPGPF AQTrY ApVNW>
[ 2870 ]      ^^^^^ ^^^^^ ^^^^  ^ ^ ^ ^^  ^ ^^ ^^ ^ ^^^ ^^^^^ ^^^ Y  ^ ^
              5         15         25         35         45         50
M37p         MASLI YRQLL TNSYs VELSD EIntI GSeKT QNVTV NPGPF AQTNY ApVvl>
[ 2844 ]      ^^^^^ ^^^^^ ^^^^  ^^^^^ ^^  ^ ^^ ^^ ^^^^^ ^^^^^ ^^^^^ ^  ^
              5         15         25         35         45         50
KUp          MASLI YRQLL TNSYs VdLhD EIeqI GSeKT QNVTV NPGPF AQTrY ApVNW>
[ 2837 ]      ^^^^^ ^^^^^ ^^^^  ^ ^ ^ ^^  ^ ^^ ^^ ^^^^^ ^^^^^ ^^^ Y  ^ ^
              5         15         25         35         45         50
ST3p         MASLI YRQLL TNSYT VELSD EIntI GSeKs QNiTi NPGPF AQTNY ApVvl>
[ 2836 ]      ^^^^^ ^^^^^ ^^^^^ ^^^^^ ^^  ^ ^^ ^   ^^  ^^^^^ ^^^^^ ^  ^
              5         15         25         35         45         50
K8p          MASLI YRQLL sNSYv tniSD EvnEI GtkKT tNVTV NPGPF AQTgY ApVdW>
[ 2735 ]      ^^^^^ ^^^^^   ^^  ^ ^^ ^  ^^ ^  ^^  ^^^^ ^^^^^ ^^^ Y ^  ^
```

Fig. 3A

```
                       60         65         70         75         80         85         90         95        100
                        *                              *                    *                              *
C486G4p      GPGET NDSTT VEPVL DGPYQ PTTFN PPVSY WMLLA PTNAG VVDQG TNNTN
SA11G4p      GPGET NDSTT VEPVL DGPYQ PTTFN PPVSY WMLLA PTNAG VVveG TNNTN>
[ 3506 ]     ^^^^^ ^^^^^ ^^^^^ ^^^^^ ^^^^^ ^^^^^ ^^^^^ ^^^^^ ^^    ^^^^^
RRVVP4p      GPGET NDSTT VEPVL DGPYQ PTsFN PPVdY WMLLA PTaAG VVveG TNNTd>
[ 3198 ]     ^^^^^ ^^^^^ ^^^^^ ^^^^^ ^^ ^^ ^^^ ^ ^^^^^ ^^ ^^ ^^    ^^^^^
DS-1p        GhGEi NDSTT VEPVL DGPYQ PTTFk PPtdY WlLis sntnG VVyes TNNnd>
[ 2870 ]     ^^ ^^ ^^^^^ ^^^^^ ^^^^^ ^^^ ^ ^^ ^^ ^^ ^^ ^^ ^^ ^^    ^^^^^
                                                  s——
M37p         eswEv NDSTT iEPVL DGPYQ P-TFk PPtdY WiLln PTdqq VVleG TNkTd>
[ 2844 ]     ^     ^^^^^ ^^^^^ ^^^^^   ^ ^ ^^ ^^ ^^^^  ^^    ^^    ^^^^^
KUp          GhGEi NDSTT VEPiL DGPYQ PTTFk PltdY WiLin sntnG VVyes TNNsd>
[ 2837 ]     ^^ ^^ ^^^^^ ^^^^^ ^^^^^ ^^^ ^ ^ ^^^ ^^ ^^ ^^ ^^ ^^    ^^^^^
                                                  s——
ST3p         eswEv NDSTT iEPVL DGPYQ P-TFK PPtdY WiLLn PTNqq VVleG TNkTd>
[ 2836 ]     ^     ^^^^^ ^^^^^ ^^^^^   ^ ^ ^^^^^ ^^^^  ^^    ^^    ^^^^^
```

Fig. 3B

```
                55      60    65    70    75    80    85    90    95   100
K8p         GhGEl pDSTl VqPtL DGPYQ PTlnl PvtdY WMLiA PTreG kVaeG TNTTd>
[ 2735 ]         ^^         ^^                              ^^    ^^^^

110         120         130         140         150
                                         *           *           *           *           *
C486G4p     RWLAT ILIKP NVQQV ERTYT LFGQQ VQVTV SNDSQ TKWKF VDLSK QTQDG 105   110   115   120   125   130   135   140   145   150
SA11G4p     RWLAT ILieP NVQQV ERTYT LFGQQ VQVTV SNDSQ TKWKF VDLSK QTQDG>
[ 3506 ]         ^^^        ^^^                              ^^    ^^^^

105   110   115   120   125   130   135   140   145   150
RRVVP4p     RWLAT ILveP NVtse tRsYT LFGtQ eQiTi ayaSQ TqWKF iDvvK tTQnG>
[ 3198 ]         ^^^    ^^^   ^ ^^   ^ ^   ^^ ^  ^ ^    ^     ^ ^  ^ ^

105   110   115   120   125   130   135   140   145
DS-1p       fWtAv IaIeP hVsQV nRqYT LFGen kQfnV eNnSd -KWKF femfK gssqG>
[ 2870 ]    ^ ^^  ^ ^^   ^             ^   ^ ^  ^ ^         ^^ ^  ^^

105   110   115   120   125   130   135   140   145
M37p        iWiAl lLveP NVtnq sRqYT LFGet kQiTV eNntn -KWKF femfr knvsa>
[ 2844 ]    ^ ^^   ^^^   ^^   ^ ^    ^ ^   ^^   ^^          ^^^    ^

105   110   115   120   125   130   135   140   145
KUp         fWtAv vaIeP hVIQV dRqYT vFGen kQfnV rNDSd -KWKF lemfr gssqn>
[ 2837 ]    ^ ^^  ^  ^   ^      ^   ^ ^    ^^    ^          ^^^    ^^^

105   110   115   120   125   130   135   140   145
ST3p        iWiAl lLveP NVtnq sRqYT LFGet kQiTV eNntn -KWKF femfr ssvss>
[ 2836 ]    ^ ^^   ^^^   ^^   ^ ^    ^ ^   ^^   ^^          ^^^
```

Fig. 3C

```
K8p
[ 2735 ]
         105   110   115   120   125   130   135   140   145   150
         RWfAc vLveP NVQnt qRqYv LdGQn VQlhv SNDSs TsWKF ilfiK lTpyG>
         ^^^^^ ^     ^^^^^ ^^^^^ ^^^^^ ^^^^^ ^^^^^ ^^^^^ ^^^^^ ^

C486G4p
                         160         170         180         190        200
                                      *                        *          *
         NYSQH GPLLS TPKLY GVMKH GGKIY TYNGE TPNAT TGYYS TTNFD TVNMT
         ^^^^^ ^^^^^ ^^^^^ ^^^^^ ^^^^^ ^^^^^ ^^^^^ ^^^^^ ^^^^^ ^^^^^

SA11G4p
[ 3506 ]
         155   160   165   170   175   180   185   190   195   200
         NYSQH GsLLS TPKLY GVMKH GGKIY TYNGE TPNAn TGYYS TTNFD TVNMT>
         ^^^^^ ^^^^^ ^^^^^ ^^^^^ ^^^^^ ^^^^^ ^^^^^ ^^^^^ ^^^^^ ^^^^^

RRVVP4p
[ 3198 ]
         155   160   165   170   175   180   185   190   195   200
         sYSQy GPLqS TPKLY aVMKH nGKIY TYNGE TPNvT TkYYS TTNyD sVNMT>
         ^^^^^ ^^^^^ ^^^^^ ^     ^^^^^ ^^^^^ ^^^   ^^^^^ ^^^   ^^^^^

DS-1p
[ 2870 ]
         150   155   160   165   170   175   180   185   190   195
         NfSnr rtLts snrLv GmlKy GGrvw TfhGE TPrAT Tdssn Tadln nisii>
         ^     ^^^^^ ^     ^     ^^^   ^^^^^ ^^^   ^^^   ^^^   ^

M37p
[ 2844 ]
         150   155   160   165   170   175   180   185   190   195
         efqhk rtLts dtKLa GflKH ynsvw TfhGE TPhAT TdYsS TsNls eVetv>
         ^     ^^^^^ ^^^   ^^^^^ ^     ^^^^^ ^^^   ^^^^^ ^^^   ^

KUp
[ 2837 ]
         150   155   160   165   170   175   180   185   190   195
         efynr rtLts dtKLv GilKy GGrIw TfhGE TPrAT Tdssn TaNln disii>
         ^     ^^^^^ ^^^   ^^^   ^^    ^^^^^ ^^^   ^^^   ^^^^^ ^

ST3p
[ 2836 ]
         150   155   160   165   170   175   180   185   190   195
         efqhk rtLts dtKLa GflKH ynsvw sfhGE TPhAT TdYsS TsNls eVetv>
         ^     ^^^^^ ^^^   ^^^^^ ^     ^^^^^ ^^^   ^^^^^ ^^^   ^
```

Fig. 3D

```
                  155   160   165   170   175   180   185   190   195   200
K8p               tYtQy stLst phKLc aWMKr dnrvY wYgGa TPNAs esYYl TiNnD nsNvs>
[ 2735 ]                                                            ^     ^

210   215   220   225   230   235   240   245   250
                                                 *                                                 *
C486G4p                                         AYCDF YIIPL AQEAK CTEYI NNGLP PIQNT RNIVP VSIVS RNIVY TRAQP
SA11G4p           205   210   215   220   225   230   235   240   245   250
[ 3506 ]          AYCDF YIIPL AQEAK CTEYI NNGLP PIQNT RNIVP VSIVS RNIVY TRAQP>
                  ^^^^^ ^^^^^ ^^^^^ ^^^^^ ^^^^^ ^^^^^ ^^^^^ ^^^^^ ^^^^^ ^^^^^

RRVVP4p           205   210   215   220   225   230   235   240   245   250
[ 3198 ]          AfCDF YIIPr eeEst CTEYI NNGLP PIQNT RNIVP laIsa RNIis hRAQa>
                  ^ ^^^ ^^^^  ^     ^^^^^ ^^^^^ ^^^^^ ^^^^^ ^   ^ ^^ ^  ^^^ ^

DS-1p             200   205   210   215   220   225   230   235   240   245
[ 2870 ]          ihseF YIIPr sQEsK CnEYI NNGLP PIQNT RNvVP lSlsS RsIqY rRAQv>
                    ^^^ ^^^^  ^^ ^ ^ ^^^ ^^^^^ ^^^^^ ^^ ^^ ^ ^ ^ ^^ ^^  ^^^^

M37p              200   205   210   215   220   225   230   235   240   245
[ 2844 ]          ihveF YIIPr sQEsK CvEYI NtGLP PmQNT RNIVP ValsS RsvtY qRAQv>
                    ^^^ ^^^^  ^^ ^ ^ ^^^ ^ ^^^ ^ ^^^ ^^^^^ ^ ^ ^ ^^ ^^  ^^^^

KUp               200   205   210   215   220   225   230   235   240   245
[ 2837 ]          ihseF YIIPr sQEsK CnEYI NNGLP PIQNT RNvVP lSlsS RsIqY kRAQv>
                    ^^^ ^^^^  ^^ ^ ^ ^^^ ^^^^^ ^^^^^ ^^ ^^ ^ ^ ^ ^^ ^^  ^^^^

ST3p              200   205   210   215   220   225   230   235   240   245
[ 2836 ]          ihveF YIIsr sQEsK CvEYI NtGLP PmQNT RNIVP ValsS RsvtY qRAQv>
                    ^^^ ^^^   ^^ ^ ^ ^^^ ^ ^^^ ^ ^^^ ^^^^^ ^ ^ ^ ^^ ^^  ^^^^
```

Fig. 3E

```
                   205    210    215    220    225    230    235    240    245    250
K8p               sdaeF  YlIPq  s

```
              255   260   265   270   275   280   285   290   295   300
K8p         NeDIV iSKTS LWKEM QYNRD IiIRF KFANS IIKSG GLGYK WSEiS FKPmN>
[ 2735 ]    ^^^^^ ^^^^^ ^^^^^ ^^^^^ ^^^^^ ^^^^^ ^^^^^ ^^^^^ ^^^^^ ^^^^<

310         320         330                   340         350
                                       *           *           *                     *           *
C486G4p     YQYTY TRDGE EVTAH TTCSV NGIND FNYNG GSLPT DFVIS KYEVI KENSF
            ^^^^^ ^^^^^ ^^^^^ ^^^^^ ^^^^^ ^^^^^ ^^^^^ ^^^^^ ^^^^^ ^^^^<

305   310   315   320   325   330   335   340   345   350
SA11G4p     YQYTY TRDGE EVTAH TTCSV NGVND FNYNG GSLPT DFVIS KYEVI KENSF>
[ 3506 ]    ^^^^^ ^^^^^ ^^^^^ ^^^^^ ^^^^^ ^^^^^ ^^^^^ ^^^^^ ^^^^^ ^^^^<

305   310   315   320   325   330   335   340   345   350
RRVVP4p     YQYTY TRDGE dVTAH TTCSV NGmND FNfNG GSLPT DFiIS rYEVI KENSY>
[ 3198 ]    ^^^^^ ^^^^^ ^^^^^ ^^^^^ ^^^^^ ^^^^^ ^^^^^ ^^^^^ ^^^^^ ^^^^<

300   305   310   315   320   325   330   335   340   345
DS-1p       YQYsY sRDGE qVTAH TTCSV NGVNn FsYNG GSLPT DFsIS rYEVI KENSY>
[ 2870 ]    ^^^^^ ^^^^^ ^^^^^ ^^^^^ ^^^^^ ^^^^^ ^^^^^ ^^^^^ ^^^^^ ^^^^<

300   305   310   315   320   325   330   335   340   345
M37p        YQYnY lRDGE qVTAH TTCSV NGVNn FsYNG GSLPT DFsvS rYEVI KENSY>
[ 2844 ]    ^^^ ^ ^^^^^ ^^^^^ ^^^^^ ^^^^^ ^^^^^ ^^^^^ ^^^^^ ^^^^^ ^^^^<

300   305   310   315   320   325   330   335   340   345
KUp         YQYnY lRDGE qVTAH TTCSV NGVNn FsYNG GSLPT DFsvS rYEVI KENSY>
[ 2837 ]    ^^^^^ ^^^^^ ^^^^^ ^^^^^ ^^^^^ ^^^^^ ^^^^^ ^^^^^ ^^^^^ ^^^^<

300   305   310   315.  320   325   330   335   340   345
ST3p        YQYnY lRDGE qVTAH TTCSV NGVNn FsYNG GlLPT hFsvS rYEVI KENSY>
[ 2836 ]    ^^^ ^ ^^^^^ ^^^^^ ^^^^^ ^^^^^ ^^^^^ ^^^^^ ^^^^^ ^^^^^ ^^^^<
```

Fig. 3G

```
                305   310   315   320   325   330   335   340   345   350
K8p             YQYTY TRDeE EVTAH TTCSV NGvND FNYNG GtLPT DFaIS rfEVI KENSY>
[ 2735 ]              ^^^^^ ^^^^^ ^     ^^^^^ ^     ^     ^     ^^^^  ^^^^^

360                      370                      380                      390              400
C486G4p         VYIDY WDDSQ AFRNM VYVRS LAADL NSVMC TGGDY SFAIP VGNYP VMTGG
                                                    *                        *                        *                        *              *

350   355   360   365   370   375   380   385   390   395   400
SA11G4p         VYIDY WDDSQ AFRNM VYVRS LAADL NSVMC TGGDY SFAIP VGNYP VMTGG>
[ 3506 ]        ^^^^^ ^^^^^ ^^^^^ ^^^^^ ^^^^^ ^^^^^ ^^^^^ ^^^^^ ^^^^^ ^^^^^

350   355   360   365   370   375   380   385   390   395   400
RRVVP4p         VYvDY WDDSQ AFRNM VYVRS LAAnL NSViC TGGDY SFAIP VGqwP VMTGG>
[ 3198 ]        ^^^^^ ^^^^^ ^^^^^ ^^^^^ ^^^^^ ^^^^^ ^^^^^ ^^^^^ ^     ^^^^^

350   355   360   365   370   375   380   385   390   395
DS-1p           VYIDY WDDSk AFRNM VYVRS LAAnL NSVkC TGGsY nFrlP VGkwP iMnGG>
[ 2870 ]        ^^^^^ ^^^^  ^^^^^ ^^^^^ ^^^^^ ^^^^  ^^^^  ^ ^^  ^     ^ ^^^

350   355   360   365   370   375   380   385   390   395
M37p            VYvDY WDDSQ AFRNM VYVRS LAAnL NSVkC TGGnY nFqlP VGawP VMsGG>
[ 2844 ]        ^^^^^ ^^^^^ ^^^^^ ^^^^^ ^^^^^ ^^^^  ^^^^  ^ ^^  ^     ^^ ^^

350   355   360   365   370   375   380   385   390   395
KUp             VYvDY WDDSk AFRNM VYVRS LAAnL NSVkC TGGsY dFsIP VGawP VMnGG>
[ 2837 ]        ^^^^^ ^^^^  ^^^^^ ^^^^^ ^^^^^ ^^^^  ^^^^  ^ ^^  ^     ^^ ^^

350   355   360   365   370   375   380   385   390   395
ST3p            VYvnY WDDSQ AlRNM VYVRS LAAnL NSVkC TGGnY nFqlP VGawP VMsGG>
[ 2836 ]        ^^ ^  ^^^^^ ^ ^^^ ^^^^^ ^^^^^ ^^^^  ^^^^  ^ ^^  ^     ^^ ^^
```

Fig. 3H

```
               355   360   365   370   375   380   385   390   395   400
K8p            VYvDY WDDSQ AFRNM VYVRS LAAnL NdVvC TGGsY SFAlP VGNhP VMsGG>
[ 2735 ]       ^^^^^ ^^^^^ ^^^^^ ^^^^^ ^^^^^ ^^^^^ ^^^^^ ^^^^^ ^^^^^ ^^

410         420         430         440         450
                                                  *           *           *           *
C486G4p        AVSLH SAGVT LSTQF TDFVS LNSLR FRFRL SVEEP PFSIL RTRVS GLYGL
               ^^^^^ ^^^^^ ^^^^^ ^^^^^ ^^^^^ ^^^^^ ^^^^^ ^^^^^ ^^^^^ ^^^^^

405   410   415   420   425   430   435   440   445   450
SA11G4p        AVSLH SAGVT LSTQF TDFVS LNSLR FRFRL SVEEP PFSIL RTRVS GLYGL>
[ 3506 ]       ^^^^^ ^^^^^ ^^^^^ ^^^^^ ^^^^^ ^^^^^ ^^^^^ ^^^^^ ^^^^^ ^^^^^

405   410   415   420   425   430   435   440   445   450
RRVVP4p        AVSLH SAGVT LSTQF TDFVS fNSLR FRFRL tVEEP sFSIt RTRVg GLYGL>
[ 3198 ]       ^^^^^ ^^^^^ ^^^^^ ^^^^^ ^^^^  ^^^^^ ^^^^  ^^^   ^^^^  ^^^^^

400   405   410   415   420   425   430   435   440   445
DS-1p          AVSLH fAGVT LSTQF TDFVS LNSLR FRFsL tVdEP sFSIL RTRti nLYGL>
[ 2870 ]       ^^^^^ ^^^^  ^^^^^ ^^^^^ ^^^^^ ^^^   ^^    ^^^^  ^^^^  ^^^^^

400   405   410   415   420   425   430   435   440   445
M37p           AVSLH fAGVT LSTeF TDFVS LNSLR FRFsL tVEEP PFSIL RTRVS GLYGL>
[ 2844 ]       ^^^^^ ^^^^  ^^^^  ^^^^^ ^^^^^ ^^^   ^     ^^^^^ ^^^^^ ^^^^^

400   405   410   415   420   425   430   435   440   445
KUp            AVSLH fAGVT LSTQF TDFVS LNSLR FRFsL tVdEP sFSIL RTRtv nLYGL>
[ 2837 ]       ^^^^^ ^^^^  ^^^^^ ^^^^^ ^^^^^ ^^^   ^^    ^^^^  ^^^^  ^^^^^

400   405   410   415   420   425   430   435   440   445
ST3p           AVSLH fAGVT LSTkF TDFVS LNSLR FRFsL tVEEP PFSIL RTRVS GLYGL>
[ 2836 ]       ^^^^^ ^^^^  ^^^^  ^^^^^ ^^^^^ ^^^   ^     ^^^^^ ^^^^^ ^^^^^
```

Fig. 3I

```
                 405   410   415   420   425   430   435   440   445   450
K8p              AVtLt SAGVT LSTQy TDyVS LNSLq FRFRL aVsEP sFSIs RTRmS GiYGL>
[ 2735 ]               ^^^^^ ^^^^^ ^^^^^ ^^^^^ ^^^^^ ^     ^^^   ^^^^^ ^^^^^

460               470         480               490               500
C486G4p          PAAKP NNSQE YYEIA GRFSL ISLVP SNDDY QTPII NSVTV RQDLE RQLGE
                                                           *                   *                   *                   *

455   460   465   470   475   480   485   490   495   500
SA11G4p          PAAKP NNSQE YYEIA GRFSL ISLVP 1NDDY QTPIm NSVTV RQDLE RQLGE>
[ 3506 ]         ^^^^^ ^^^^^ ^^^^^ ^^^^^ ^^^^^       ^^^^^ ^^^^^ ^^^^^ ^^^^^

455   460   465   470   475   480   485   490   495   500
RRVVP4p          PAAyP NNgkE YYEVA GR1SL ISLVP SNDDY QTPIt NSVTV RQDLE RQLGE>
[ 3198 ]         ^^^   ^^    ^^ ^^ ^^ ^^ ^^^^^ ^^^^^ ^^^^  ^^^^^ ^^^^^ ^^^^^

450   455   460   465   470   475   480   485   490   495
DS-1p            PAAnP NNgnE YYEms GRFSL ISLVq tNDDY QTPIm NSVTV RQDLE RQLnd>
[ 2870 ]         ^^^   ^^    ^^    ^^^^^ ^^^   ^^^^^ ^^^^^ ^^^^^ ^^^^^ ^^^

450   455   460   465   470   475   480   485   490   495
M37p             PAfnP NsghE YYEIA GRFsf I1LVP SNDDY QTPIm NSVTV RQDLE RQLGd>
[ 2844 ]         ^^    ^     ^^^^^ ^^^   ^^^^^ ^^^^^ ^^^^^ ^^^^^ ^^^^^ ^^^

450   455   460   465   470   475   480   485   490   495
KUp              PAAnP NNgnE YYEIs GRFSL ISLVP tNDDY QTPIm NSVTV RQDLE RQLtd>
[ 2837 ]         ^^^   ^^    ^^^^  ^^^^^ ^^^^^ ^^^^^ ^^^^^ ^^^^^ ^^^^^ ^^^

450   455   460   465   470   475   480   485   490   495
ST3p             PAsnP NsghE YYEIA GRFSL ISLVP SNDDY QTPIm NSiTV RQDLE RQLGd>
[ 2836 ]         ^^    ^     ^^^^^ ^^^^^ ^^^^^ ^^^^^ ^^^^^ ^^^   ^^^^^ ^^^
```

Fig. 3J

```
              455   460   465   470   475   480   485   490   495   500
K8p           PAvnP NNSaE YYEIA GRFSL ISLVP tNDDY QTPIa NSVTV RQDLE RQLGE>
[2735]        ^^    ^     ^^^         ^^^^                           ^^^^

510         520         530         540   550
                          *           *           *           *     *
C486G4p       LRDEF NNLSQ QIAMS QLIDL ALLPL DMFSM FSGIK STIDA AKSMA TNVMK
                                                                    ^^^^

505   510   515   520   525   530   535   540   545   550
SA11G4p       LRDEF NNLSQ QIAMS QLIDL ALLPL DMFSM FSGIK STIDA AKSMA TNVMK>
[3506]                                                              ^^^^

505   510   515   520   525   530   535   540   545   550
RRVVP4p       LReEF NaLSQ eIAMS QLIyL ALLPL DMFSM FSGIK STIDA AKSMA TsVMK>
[3198]        ^^^^^                                                 ^^^

500   505   510   515   520   525   530   535   540   545
DS-1p         LReEF NsLSQ eIAMS QLIDL ALLPL DMFSM FSGIK STIDl tKSMA TsVMK>
[2870]        ^^^^                                                  ^^^

500   505   510   515   520   525   530   535   540   545
M37p          LReEF NsLSQ eIAMt QLIDL ALLPL DMFSM FSGIK STIDA AKSMA TKVMK>
[2844]        ^^^^                                                  ^^^

500   505   510   515   520   525   530   535   540   545
KUp           LReEF NsLSQ eIAMS QLIDL ALLPL DMFSM FSe1K STID1 tKSMA TsVMK>
[2837]        ^^^^                                                  ^^^

500   505   510   515   520   525   530   535   540   545
ST3p          LReEF NsLSQ eIAit QLIDL ALLPL DMFSM FSGIK STIDA AKSMA TKVMK>
[2836]        ^                                                     ^^^
```

Fig. 3K

```
                   505   510   515   520   525   530   535   540   545   550
K8p                LReEF NsLSQ eIAvs QLIDL AtLPL DMFSM FSGIK STveA vKSMt TNVMK>
[ 2735 ]           ^^^^^ ^^^ ^ ^^^^^ ^^^^^ ^^^^^ ^^^^^ ^^^^^ ^^^^^ ^^^^

560                 580            600
                                                  *                   *              *
C486G4p            RFKKS SLANS VSTLT DSLSD AASSI SRSAS VRSVS STASA WTEVS NITSD
                   ^^^^^ ^^^^^ ^^^^^ ^^^^^ ^^^^^ ^^^^^ ^^^^^ ^^^^^ ^^^^^ ^^^^^

555   560   565   570   575   580   585   590   595   600
SA11G4p            RFKKS SLANS VSTLT DSLSD AASSI SRSAS VRSVS STASA WTEVS NIaSD>
[ 3506 ]           ^^^^^ ^^^^^ ^^^^^ ^^^^^ ^^^^^ ^^^^^ ^^^^^ ^^^^^ ^^^^^ ^^^^

555   560   565   570   575   580   585   590   595   600
RRVVP4p            kFKKS gLANS VSTLT DSLSD AASSI SRgAS iRSVg SsASA WTdVS tqitD>
[ 3198 ]           ^^^^^ ^^   ^ ^^^^^ ^^^^^ ^^^^^ ^^    ^    ^^^^^ ^^^^

550   555   560   565   570   575   580   585   590   595
DS-1p              kFrKS kLAtS iSemT nSLSD AASSa SRSAS iRsni STisn WTnts ksvSn>
[ 2870 ]           ^^^^^ ^^    ^    ^ ^^^^^ ^^^^^ ^^^^^ ^^    ^ ^^^^

550   555   560   565   570   575   580   585   590   595
M37p               kFKrS gLAtS iSeLT gSLSn AASSI SRSsS iRsni SsiSv WTdVS eqiag>
[ 2844 ]           ^^^^^ ^^    ^    ^ ^^^^^ ^^^^^ ^^^^^ ^^    ^ ^^^^

550   555   560   565   570   575   580   585   590   595
KUp                kFrKS kLAtS iSemT hSLSD AASSa SRSvS iRsni STisn WTnVS NdvSn>
[ 2837 ]           ^^^^^ ^^    ^    ^ ^^^^^ ^^^^^ ^^^^^ ^^    ^ ^^^^

550   555   560   565   570   575   580   585   590   595
ST3p               kFrKS gLAtS iSeLT rSLSn AASSI SRSsS iRsni SsvSe WTdVS eqiag>
[ 2836 ]           ^^^^^ ^^    ^    ^ ^^^^^ ^^^^^ ^^^^^ ^^    ^ ^^^^
```

Fig. 3L

```
                555    560   565    570    575    580    585    590    595
K8p             RFKtS SLANa isdLT snmSe AASSv -RltS VRSVg titlp rarVS lqvgD>
[ 2735 ]         ^^^^  ^^    ^^     ^^     ^^^^^        ^     ^       ^

610           620                     630           640           650
                                                          *             *                       *             *             *
C486G4p         INVTT SSIST QTSTI SRRLR LKEMA TQTDG MNFDD ISAAV LKTKI DKSTQ
                ^^^^^ ^^^^^ ^^^^^ ^^^^^ ^^^^^ ^^^^^ ^^^^^ ^^^^^ ^^^^^ ^^^^^

605   610   615   620   625   630   635   640   645   650
SA11G4p         INVTT SSIST QTSTI SRRLR LKEMA TQTDG MNFDD ISAAV LKTKI DKSTQ>
[ 3506 ]        ^^^^^ ^^^^^ ^^^^^ ^^^^^ ^^^^^ ^^^^^ ^^^^^ ^^^^^ ^^^^^ ^^^^^

605   610   615   620   625   630   635   640   645   650
RRVVP4p         vsssv SSIST QTSTI SRRLR LKEMA TQTeG MNFDD ISAAV LKTKI DrSTQ>
[ 3198 ]         ^    ^^^^^ ^^^^^ ^^^^^ ^^^^^ ^^ ^^ ^^^^^ ^^^^^ ^^^^^ ^^ ^^

600   605   610   615   620   625   630   635   640   645
DS-1p           vtdsv ndIST QTSTI SkkLR LrEMi TQTeG lsFDD ISAAV LKTKI DmSTQ>
[ 2870 ]               ^^^^ ^^^^^ ^  ^^ ^  ^  ^^ ^  ^ ^^^ ^^^^^ ^^^^^ ^ ^^^

600   605   610   615   620   625   630   635   640   645
M37p            ssdsv SnIST QmSaI SRRLR LrEit TQTeG MNFDD ISAAV LKTKI DrSTh>
[ 2844 ]               ^^^^ ^ ^ ^ ^^^^^ ^  ^  ^^ ^  ^^^^^ ^^^^^ ^^^^^ ^^ ^

600   605   610   615   620   625   630   635   640   645
KUp             vtnsl SdIST QTSTI SknLR LKEMi TQTeG MsFDD ISAAV LKTKI DmSTQ>
[ 2837 ]         ^     ^^^^ ^^^^^ ^ ^^^ ^^^^  ^^ ^  ^ ^^^ ^^^^^ ^^^^^ ^ ^^^

600   605   610   615   620   625   630   635   640   645
ST3p            ssdsv rnIST QiSaI SRRLR LrEit TQTeG MNFiD ISAAV LKTKI DrSTh>
[ 2836 ]               ^^^^ ^ ^ ^ ^^^^^ ^  ^  ^^ ^  ^^^ ^ ^^^^^ ^^^^^ ^^ ^
```

Fig. 3M

```
K8p       600    605    610    615    620    625    630    635    640    645
[ 2735 ]  dlrsm  qdvST  QvSnv  SRnlR  LKEft  TQTDt  lsFDD  ISAAV  LKTKl  DKSTQ>
          ^^^^^  ^^^^^  ^^^^^  ^^^^^  ^^^^^  ^^^^^  ^^^^^  ^^^^^  ^^^^^  ^^^^^

660           670           680           690           700
                  *             *             *             *             *
C486G4p   LNTNT  LPEIV  TEASE  KFIPN  RAYRV  IKDDE  VLEAS  TDGKY  FAYKV  ETILK
                                                                              i
                                                                              |--
          655    660    665    670    675    680    685    690    695    700
SA11G4p   LNTNT  LPEIV  TEASE  KFIPN  RAYRV  IKDDE  VLEAS  iDGKY  FAYKV  ETfee>
[ 3506 ]  ^^^^^  ^^^^^  ^^^^^  ^^^^^  ^^^^^  ^^^^^  ^^^^^  ^^^^^  ^^^^^  ^^^^^
                                                                              i
                                                                              |--
          655    660    665    670    675    680    685    690    695    700
RRVVP4p   ispNT  LPdIV  TEASE  KFIPN  RAYRV  InnDE  VfEAg  TDGrY  FAYrV  ETfde>
[ 3198 ]  ^^^^^  ^^^^^  ^^^^^  ^^^^^  ^^^^^  ^^^^^  ^^^^^  ^^^^^  ^^^^^  ^^^^^
                                                                              i
                                                                              |--
          650    655    660    665    670    675    680    685    690    695
DS-1p     igkNT  LPdIV  TEASE  KFIPk  RsyRV  lKDDE  VmEln  TeGKf  FAYKV  dTlne>
[ 2870 ]  ^^^^^  ^^^^^  ^^^^^  ^^^^^  ^^^^^  ^^^^^  ^^^^^  ^^^^^  ^^^^^  ^^^^^
                                                                              v
                                                                              |--
          650    655    660    665    670    675    680    685    690    695
M37p      ispdT  LPdIm  TEsSk  KFIPk  RAYRV  lKDDE  VmEAd  vDGKf  FAYKV  dTfee>
[ 2844 ]  ^^^^^  ^^^^^  ^^^^^  ^^^^^  ^^^^^  ^^^^^  ^^^^^  ^^^^^  ^^^^^  ^^^^^
```

Fig. 3N

```
                                                                          v
KUp       650      655      660      665      670      675      680      685      690      695
[ 2837 ]  igkNT LPdIV TEASE KFIPk RsYRi lKDDE VmEin TeGKv FAYKi dTlne>
          ^^^^^ ^^^^^ ^^^^^ ^^^^^ ^^^^^ ^^^^^ ^^^^^ ^^^^^ ^^^^^ ^^^^^
                                                                          v
ST3p      650      655      660      665      670      675      680      685      690      695
[ 2836 ]  irpdT LPdIi TEssE KFIPk RAYRV lKDDE VmEAd vDGKf FAYKV dTfee>
          ^^^^^ ^^^^^ ^^^^^ ^^^^^ ^^^^^ ^^^^^ ^^^^^ ^^^^^ ^^^^^ ^^^^^
                                                                          i
K8p       650      655      660      665      670      675      680      685      690      695
[ 2735 ]  isqqT mPdIi aEssE KFIPk RsYRi vdeDi rfEtg iDGtf yAYKV dTfne>
          ^^^^^ ^^^^^ ^^^^^ ^^^^^ ^^^^^ ^^^^^ ^^^^^ ^^^^^ ^^^^^ ^^^^^

710      720      730      740      750
                         *        *        *        *        *
C486G4p   RFHSM YKFAD LVTDS PVISA IIDFK TLKNL NDNYG ISRQQ ALNLL RSDPR 705      710      715      720      725      730      735      740      745      750
SA11G4p   pFd-v qKFAD LVTDS PVISA IIDFK TLKNL NDNYG ISRQQ ALNLL RSDPR>
[ 3506 ]  ^ ^   ^^^^^ ^^^^^ ^^^^^ ^^^^^ ^^^^^ ^^^^^ ^^^^^ ^^^^^ ^^^^^

705      710      715      720      725      730      735      740      745      750
RRVVP4p   pFd-v qKFAD LVTDS PVISA IIDFK TLKNL NDNYG ISRQQ AfNLL RSDPR>
[ 3198 ]  ^ ^   ^^^^^ ^^^^^ ^^^^^ ^^^^^ ^^^^^ ^^^^^ ^^^^^ ^^^^^ ^^^^^

```
[ 2870 ]        pFd-i nKFAe LVTDS PVISA IIDFK TLKNL NDNYG ItRie AfNLi kSnPn>
                      ^^^^       ^^^^^ ^^^^^ ^^^^^ ^^^^^ ^^^^^ ^^ ^  ^^ ^^ ^^^^^
                      705   710   715   720   725   730   735   740   745

M37p            pFd-v dKFvD LVTDS PVISA IIDFK TLKNL NDNYG ItRsQ AldLi RSDPR>
[ 2844 ]              ^  ^  ^^^^^ ^^^^^ ^^^^^ ^^^^^ ^^^^^ ^^ ^  ^^ ^^ ^^^^^
                      705   710   715   720   725   730   735   740   745

KUp             pFd-v nKFAe LVTnS PVISA IIDFK TLKNL NDNYG ItRie ALNLi kSnPn>
[ 2837 ]              ^^^^^ ^^^ ^ ^^^^^ ^^^^^ ^^^^^ ^^^^^ ^^^^^ ^^^^^ ^^^^^
                      705   710   715   720   725   730   735   740   745

ST3p            pFd-v dKFvD LVTDS PVISA IIDFK TLKNL NDNYG ItRsQ AldLi RSDPR>
[ 2836 ]              ^  ^  ^^^^^ ^^^^^ ^^^^^ ^^^^^ ^^^^^ ^^ ^  ^^ ^^ ^^^^^
                      705   710   715   720   725   730   735   740   745

K8p             pFd-M erFnk LiTDS PVISA IIDFK TLKNL NDNYG ItkkQ AmeLL hSnPk>
[ 2735 ]              ^     ^ ^^^ ^^^^^ ^^^^^ ^^^^^ ^^^^^ ^^ ^  ^^ ^^ ^^ ^^
                      705   710   715   720   725   730   735   740   745

*             *
                                      760           770
C486G4p         VLREF INQDN PIIRN RIESL IMQCR L 755   760   765   770   775
SA11G4p         VLREF INQDN PIIRN RIESL IMQCR L>
[ 3506 ]        ^^^^^ ^^^^^ ^^^^^ ^^^^^ ^^^^^ ^

755   760   765   770   775
RRVVP4p         VLREF INQDN PIIRN RIEqL IMQCR L>
[ 3198 ]        ^^^^^ ^^^^^ ^^^^^ ^^^ ^ ^^^^^ ^
```

Fig. 3P

```
DS-1p      750   755   760   765   770   775
[ 2870 ]   VLRnF INQnN PIIRN RIEqL IlQCk L>
           ^^^^^ ^^^^^ ^^^^^ ^^^^^ ^^^^^ ^

M37p       750   755   760   765   770   775
[ 2844 ]   VLRdF INQnN PIIkN RIEqL IlQCR L>
           ^^^^^ ^^^^^ ^^^^^ ^^^^^ ^^^^^ ^

KUp        750   755   760   765   770   775
[ 2837 ]   VLRnF INQnN PIIRN RIEqL IlQCk L>
           ^^^ ^ ^^^^^ ^^^^^ ^^^^^ ^^^^^ ^

ST3p       750   755   760   765   770   775
[ 2836 ]   VLRdF INQnN PIIRN RIEqL IlQCR L>
           ^^^^^ ^^^^^ ^^^^^ ^^^^^ ^^^^^ ^

K8p        750   755   760   765   770   775
[ 2735 ]   tLkEF INnnN PIIRN RIEnL IsQCR L>
           ^^^ ^ ^^ ^^ ^^^^^ ^^^^^ ^^^^^ ^
```

Fig. 3Q

Sequence Range: 1 to 2363

```
             10              20              30              40
              *               *               *               *
GGC TAT AAA ATG GCT TCA CTC ATT TAT AGA CAG TTG CTT ACT AAT
    Met Ala Ser Leu Ile Tyr Arg Gln Leu Leu Thr Asn>

50              60              70              80              90
      *               *               *               *               *
TCA ACA GTA GAA CTT TCA GAT GAA ATC CAA GAA ATT GGA TCG
Ser Tyr Thr Val Glu Leu Ser Asp Glu Ile Gln Glu Ile Gly Ser>

100             110             120             130
             *               *               *               *
ACT AAG ACT CAA AAC GTT ACC GTT AAT CCA GGA CCG TTC GCG CAA
Thr Lys Thr Gln Asn Val Thr Val Asn Pro Gly Pro Phe Ala Gln>

140             150             160             170             180
     *               *               *               *               *
ACA AAT TAC GCT TCA GTT AAT TGG GGA CCT GGT GAA ACG AAT GAC
Thr Asn Tyr Ala Ser Val Asn Trp Gly Pro Gly Glu Thr Asn Asp>

190             200             210             220
             *               *               *               *
TCA ACT ACA GTT GAA CCA GTG CTT GAT GGA CCA TAT CAA CCA ACG
Ser Thr Thr Val Glu Pro Val Leu Asp Gly Pro Tyr Gln Pro Thr>

230             240             250             260             270
     *               *               *               *               *
ACT TTT AAT CCA CCT GTA AGT TAT TGG ATG TTG TTA GCA CCA ACG
Thr Phe Asn Pro Pro Val Ser Tyr Trp Met Leu Leu Ala Pro Thr>
```

Fig. 4A

```
          280             290             300             310
           *               *               *               *
AAC GCG GGG GTA GAT CAA GGT ACG AAC AAT ACA AAC AGA TGG
Asn Ala Gly Val Asp Gln Gly Thr Asn Asn Thr Asn Arg Trp>

320             330             340             350             360
           *               *               *               *               *
TTA GCG ACA ATA TTA ATT AAA CCA AAT GTA CAG CAA GTT GAG CGA
Leu Ala Thr Ile Leu Ile Lys Pro Asn Val Gln Gln Val Glu Arg>

370             380             390             400
           *               *               *               *
ACA TAT ACA TTA TTT GGG CAA CAA GTT CAA GTA ACA TCA AAT
Thr Tyr Thr Leu Phe Gly Gln Gln Val Gln Val Thr Ser Asn>

410             420             430             440             450
           *               *               *               *               *
GAT TCA CAG ACA AAG TGG AAG TTT GTG GAT CTA AGT AAG CAG ACA
Asp Ser Gln Thr Lys Trp Lys Phe Val Asp Leu Ser Lys Gln Thr>

460             470             480             490
           *               *               *               *
CAA GAT GGT AAT TAT TCA CAA CAC GGT CCT CTA CTG TCA ACA CCG
Gln Asp Gly Asn Tyr Ser Gln His Gly Pro Leu Leu Ser Thr Pro>

500             510             520             530             540
           *               *               *               *               *
AAA CTG TAT GGA GTG ATG AAA CAT GGA GGT AAA ATT TAC ACT TAT
Lys Leu Tyr Gly Val Met Lys His Gly Gly Lys Ile Tyr Thr Tyr>
```

Fig. 4B

```
      550              560              570              580
       *                *                *                *
AAT GGA GAG ACA CCG AAC GCA ACT ACT GGT TAC TAC TCT ACA ACT
Asn Gly Glu Thr Pro Asn Ala Thr Thr Gly Tyr Tyr Ser Thr Thr>

590              600              610              620              630
       *                *                *                *                *
AAC TTT GAC ACT GTA AAC ATG ACA GCA TAT TGT GAT TTT TAT ATA
Asn Phe Asp Thr Val Asn Met Thr Ala Tyr Cys Asp Phe Tyr Ile>

640              650              660              670
       *                *                *                *
ATT CCA TTA GCA CAA GAA GCA AAA TGC ACT GAA TAC ATA AAT AAT
Ile Pro Leu Ala Gln Glu Ala Lys Cys Thr Glu Tyr Ile Asn Asn>

680              690              700              710              720
       *                *                *                *                *
GGA TTA CCA CCA ATA CAA AAT ACG AGA AAT ATC GTA CCA GTT TCG
Gly Leu Pro Pro Ile Gln Asn Thr Arg Asn Ile Val Pro Val Ser>

730              740              750              760
       *                *                *                *
ATA GTA TCA AGG AAT ATT GTA TAT ACA AGA GCA CAA CCT AAT CAA
Ile Val Ser Arg Asn Ile Val Tyr Thr Arg Ala Gln Pro Asn Gln>

770              780              790              800              810
       *                *                *                *                *
GAC ATA GTG GTA TCA AAA ACT TCA TTA TGG AAA GAG ATG CAA TAT
Asp Ile Val Val Ser Lys Thr Ser Leu Trp Lys Glu Met Gln Tyr>
```

Fig. 4C

```
        820             830             840             850
         *               *               *               *
AAT AGA GAT ATA GTG ATA AGA TTT AAA GCT AAC TCA ATC ATA
Asn Arg Asp Ile Val Ile Arg Phe Lys Ala Asn Ser Ile Ile>

860             870             880             890             900
         *               *               *               *               *
AAA TCA GGG GGA TTG GGA TAT AAA TGG TCA GAA GTG TCA TTT AAA
Lys Ser Gly Gly Leu Gly Tyr Lys Trp Ser Glu Val Ser Phe Lys>

910             920             930             940
         *               *               *               *
CCA GCT AAT TAT CAG TAC ACA TAT ACC AGA GAT GGT GAA GAA GTT
Pro Ala Asn Tyr Gln Tyr Thr Tyr Thr Arg Asp Gly Glu Glu Val>

950             960             970             980             990
         *               *               *               *               *
ACT GCA CAT ACT ACG TGT TCA GTA AAT GGA ATA AAT GAT TTT AAT
Thr Ala His Thr Thr Cys Ser Val Asn Gly Ile Asn Asp Phe Asn>

1000            1010            1020            1030
         *               *               *               *
TAT AAT GGT GGA TCA TTA CCG ACT GAT TTC GTA ATA TCA AAA TAT
Tyr Asn Gly Gly Ser Leu Pro Thr Asp Phe Val Ile Ser Lys Tyr>

1040            1050            1060            1070            1080
         *               *               *               *               *
GAA GTG ATT AAG GAA AAT TCT TTT GTG TAT ATA GAC TAC TGG GAC
Glu Val Ile Lys Glu Asn Ser Phe Val Tyr Ile Asp Tyr Trp Asp>
```

Fig. 4D

```
                    1090           1100           1110           1120
                     *              *              *              *
GAT TCA CAA GCA TTT AGA AAC ATG GTA TAT GTA CGC TCG TTG GCA
Asp Ser Gln Ala Phe Arg Asn Met Val Tyr Val Arg Ser Leu Ala⟩

1130           1140           1150           1160           1170
      *              *              *              *              *
GCC GAT TTA AAT TCG GTA ATG TGT ACA GGA GGT GAC TAT AGT TTT
Ala Asp Leu Asn Ser Val Met Cys Thr Gly Gly Asp Tyr Ser Phe⟩

1180           1190           1200           1210
      *              *              *              *
GCG ATT CCA GTT GGT AAT TAT CCA GTT ATG ACT GGG GCT GTG
Ala Ile Pro Val Gly Asn Tyr Pro Val Met Thr Gly Gly Ala Val⟩

1220           1230           1240           1250           1260
      *              *              *              *              *
TCA TTG CAT TCA GCA GGT GTA ACT TTA TCA ACG CAG TTT ACA GAT
Ser Leu His Ser Ala Gly Val Thr Leu Ser Thr Gln Phe Thr Asp⟩

1270           1280           1290           1300
      *              *              *              *
TTC GTA TCA TTA AAT TCA CTG AGA TTT AGA TTT AGA TTA TCA GTA
Phe Val Ser Leu Asn Ser Leu Arg Phe Arg Phe Arg Leu Ser Val⟩

1310           1320           1330           1340           1350
      *              *              *              *              *
GAA GAA CCG CCG TTC TCA ATT CTA CGG ACC AGA GTT AGT GGA TTG
Glu Glu Pro Pro Phe Ser Ile Leu Arg Thr Arg Val Ser Gly Leu⟩
```

Fig. 4E

```
            1360                1370                1380                1390
              *                   *                   *                   *
TAT GGA CTT CCA GCG GCA AAA CCG AAT AAT TCA CAA GAA TAT TAT
Tyr Gly Leu Pro Ala Ala Lys Pro Asn Asn Ser Gln Glu Tyr Tyr>
            1400                1410                1420                1430                1440
              *                   *                   *                   *                   *
GAG ATA GCT GGG AGA TTT TCA ATA TCA TTA CTC GTA CCG TCA AAT
Glu Ile Ala Gly Arg Phe Ser Ile Ser Leu Leu Val Pro Ser Asn>
            1450                1460                1470                1480
              *                   *                   *                   *
GAT GAT TAT CAG ACA CCA ATA AAT TCA ACT GTA CGA CAA
Asp Asp Tyr Gln Thr Pro Ile Asn Ser Val Thr Val Arg Gln>
            1490                1500                1510                1520                1530
              *                   *                   *                   *                   *
GAT TTA GAA CGA CAA TTA GGA GAA CTA GAA AGA GAT GAA TTT AAC AAT
Asp Leu Glu Arg Gln Leu Gly Glu Leu Glu Arg Asp Glu Phe Asn Asn>
            1540                1550                1560                1570
              *                   *                   *                   *
TTA TCA CAA CAA ATC GCT ATG TCA CAA CTG ATA GAT CTT GCG TTA
Leu Ser Gln Gln Ile Ala Met Ser Gln Leu Ile Asp Leu Ala Leu>
            1580                1590                1600                1610                1620
              *                   *                   *                   *                   *
CTA CCG TTA GAC ATG TTC TCA ATG TTT TCA GGG ATT AAG AGT ACA
Leu Pro Leu Asp Met Phe Ser Met Phe Ser Gly Ile Lys Ser Thr>
```

Fig. 4F

```
                      1630           1640           1650           1660
                       *              *              *              *
ATT GAC GCA GCG AAG TCT ATG GCG ACG AAT GTA ATG AAG AGA TTT
Ile Asp Ala Ala Lys Ser Met Ala Thr Asn Val Met Lys Arg Phe>

1670           1680           1690           1700           1710
        *              *              *              *              *
AAA AAG TCA AGT CTC GCT AAC TCA GTG TCA ACG CTC ACT GAT TCA
Lys Lys Ser Ser Leu Ala Asn Ser Val Ser Thr Leu Thr Asp Ser>

1720           1730           1740           1750
        *              *              *              *
TTG TCT GAT GCA GCA TCA TCA ATT TCT AGA AGT GCA TCG GTT AGA
Leu Ser Asp Ala Ala Ser Ser Ile Ser Arg Ser Ala Ser Val Arg>

1760           1770           1780           1790           1800
        *              *              *              *              *
TCA GTT AGT TCA ACT GCA TCA GCT TGG ACG GAA GTA TCT AAC ATT
Ser Val Ser Ser Thr Ala Ser Ala Trp Thr Glu Val Ser Asn Ile>

1810           1820           1830           1840
        *              *              *              *
ACA TCA GAT ATT AAT GTG ACA ACG AGC TCG ATC TCT ACA CAG ACA
Thr Ser Asp Ile Asn Val Thr Thr Ser Ser Ile Ser Thr Gln Thr>

1850           1860           1870           1880           1890
        *              *              *              *              *
TCA ACA ATA AGC AGA AGG TTA AGA CTA AAA GAA ATG GCG ACT CAA
Ser Thr Ile Ser Arg Arg Leu Arg Leu Lys Glu Met Ala Thr Gln>
```

Fig. 4G

```
         1900            1910            1920            1930
           *               *               *               *
ACG GAC GGT ATG AAT TTT GAT GAT ATA TCA GCA GCA GTA CTC AAG
Thr Asp Gly Met Asn Phe Asp Asp Ile Ser Ala Ala Val Leu Lys>

1940            1950            1960            1970            1980
    *               *               *               *               *
ACT AAA ATT GAT AAA TCA ACC CAG TTA AAT ACA AAT ACA TTG CCG
Thr Lys Ile Asp Lys Ser Thr Gln Leu Asn Thr Asn Thr Leu Pro>

1990            2000            2010            2020
           *               *               *               *
GAA ATA GTA ACT GAG GCT TCA GAA AAG TTT ATA CCA AAT AGA GCG
Glu Ile Val Thr Glu Ala Ser Glu Lys Phe Ile Pro Asn Arg Ala>

2030            2040            2050            2060            2070
    *               *               *               *               *
TAC CGT GTA ATT AAA GAT GAT GAA GTG CTA GAG GCT AGT ACT GAT
Tyr Arg Val Ile Lys Asp Asp Glu Val Leu Glu Ala Ser Thr Asp>

2080            2090            2100            2110
           *               *               *               *
GGT AAA TAT TTC GCT TAC AAA GTT GAA ACC ATT TTG AAG AGA TTC
Gly Lys Tyr Phe Ala Tyr Lys Val Glu Thr Ile Leu Lys Arg Phe>

2120            2130            2140            2150            2160
    *               *               *               *               *
CAT TCG ATG TAC AAA TTC GCT GAC TTA GTG ACT GAC TCA CCA GTT
His Ser Met Tyr Lys Phe Ala Asp Leu Val Thr Asp Ser Pro Val>
```

Fig. 4H

```
          2170              2180              2190              2200
           *                 *                 *                 *
ATA TCG GCA ATA ATT GAC TTT AAA ACT CTT AAG AAT CTA AAT GAT
Ile Ser Ala Ile Ile Asp Phe Lys Thr Leu Lys Asn Leu Asn Asp>

2210              2220              2230              2240              2250
           *                 *                 *                 *                 *
AAT TAC GGA ATA AGC AGA CAA CAA GCA CTA CAA AAT CTT CTA AGA TCT
Asn Tyr Gly Ile Ser Arg Gln Gln Ala Leu Gln Asn Leu Leu Arg Ser>

2260              2270              2280              2290
           *                 *                 *                 *
GAT CCG CGA GTA TTA CGT GAA TTT ATT AAT CAG GAT AAT CCA ATA
Asp Pro Arg Val Leu Arg Glu Phe Ile Asn Gln Asp Asn Pro Ile>

2300              2310              2320              2330              2340
           *                 *                 *                 *                 *
ATA CGA AAT AGA ATA GAA AGT TTG ATA ATG CAA TGT CGC TTG TAA
Ile Arg Asn Arg Ile Glu Ser Leu Ile Met Gln Cys Arg Leu End>

2350              2360
           *                 *
GCA ACT GAA CAA GAG GAT GTG AC
```

Fig. 41

Sequence Range: 1 to 1062

```
              10            20            30            40
               *             *             *             *
GGC TTT AAA AGC GAG AAT TTC CGT TTG GCT AGC GGT TAG CTC CTT
CCG AAA TTT TCG CTC TTA AAG GCA AAC CGA TCG CCA ATC GAG GAA
                                                    Leu Leu>

50            60            70            80            90
               *             *             *             *             *
TTA ATG TAT GGT ATT GAA TAT ACC ACA ATT CTA ATC TTC TTG ACA
AAT TAC ATA CCA TAA CTT ATA TGG TGT TAA GAT TAG AAG AAC TGT
Leu Met Tyr Gly Ile Glu Tyr Thr Thr Ile Leu Asp Ile Phe Leu Thr>

100           110           120           130
               *             *             *             *
TCG ATT ACA TTA TTG AAT TAT ATC TTA AAA TCA ATA ACG AGA ATA
AGC TAA TGT AAT AAC TTA ATA TAG AAT TTT AGT TAT TGC TCT TAT
Ser Ile Thr Leu Leu Asn Tyr Ile Leu Lys Ser Ile Thr Arg Ile>

140           150           160           170           180
               *             *             *             *             *
ATG GAC TAT ATA ATT TAC AGA TTT AAA CTG CTT ATA GTA GTG ATC TTG
TAC CTG ATA TAT TAA ATG TCT AAA GAC GAA TAT CAT CAC TAG AAC
Met Asp Tyr Ile Ile Tyr Arg Phe Lys Leu Leu Ile Val Val Ile Leu>

190           200           210           220
               *             *             *             *
GCC ACC ATA AAT GCG CAA AAC TAT GGA GTA AAT TTG CCA ATT
CGG TGG TAT TTA CGC GTT TTG ATA CCT CAT TTA AAC GGT TAA
Ala Thr Ile Ile Asn Ala Gln Asn Tyr Gly Val Asn Leu Pro Ile>
```

```
         230             240             250             260             270
          *               *               *               *               *
ACA GGT TCA ATG GAT ACT GCG TAT GCA GAC TCT ACA CAA AGT GAG
TGT CCA AGT TAC CTA TGA CGC ATA CGT CTG AGA TGT GTT TCA CTC
Thr Gly Ser Met Asp Thr Ala Tyr Ala Asp Ser Thr Gln Ser Glu>

280             290             300             310
          *               *               *               *
CCA TTT TTG ACA TCA ACC CTT TGT TTG TAT TAT CCT GTT GAG GCA
GGT AAA AAC TGT AGT TGG GAA ACA AAC ATA ATA GGA CAA CTC CGT
Pro Phe Leu Thr Ser Thr Leu Cys Leu Tyr Tyr Pro Val Glu Ala>

320             330             340             350             360
          *               *               *               *               *
TCA AAC GAA ATA GCT GAT ACC GAA TGG CCA ACA GGA TCA GTG TAC CTT AAA
AGT TTG CTT TAT CGA CTA TGG CTT ACC CTA TGG ACC CTA AAT AGT GTT CAA
Ser Asn Glu Ile Ala Asp Thr Glu Trp Pro Thr Gly Ser Val Tyr Leu Ser Gln>

370             380             390             400
          *               *               *               *
TTG TTC ACA AAA GGA TGG CCA ACA GGA TCA GTG TAC CTT AAA
AAC AAG AAC TGT TTT CCT ACC GGT TGT CCT AGT CAC ATG GAA TTT
Leu Phe Leu Thr Lys Gly Trp Pro Thr Gly Ser Val Tyr Leu Lys>

410             420             430             440             450
          *               *               *               *               *
GAA TAT GCT GAT ATA GCG GCC TTT GTG TCA GAA CCA CAG TTA TAC
CTT ATA CGA CTA TAT CGC CGG AAA AGT CAC CTT GGT GTC AAT ATG
Glu Tyr Ala Asp Ile Ala Ala Phe Val Ser Glu Val Pro Gln Leu Tyr>
```

```
      460            470            480            490
       *              *              *              *
TGC GAT TAT AAT TTA GTT TTA ATG AAA TAT GAC TCT ACA CAA GAA
ACG CTA ATA TTA AAT CAA AAT TAC TTT ATA CTG AGA TGT GTT CTT
Cys Asp Tyr Asn Leu Val Leu Met Lys Tyr Asp Ser Thr Gln Glu>

500            510            520            530            540
       *              *              *              *              *
CTA GAT ATG TCT GAA TTG GCC GAT CTT ATA TTG AAC GAA TGG CTG
GAT CTA TAC AGA CTT AAC CGG CTA GAA TAT AAC TTG CTT ACC GAC
Leu Asp Met Ser Glu Leu Ala Asp Leu Ile Leu Asn Glu Trp Leu>

550            560            570            580
       *              *              *              *
TGC AAT CCA ATG GAC ATA ACG CTA TAT TAT CAG CAG ACT GAT
ACG TTA GGT TAC CTG TAT TGC GAT ATA ATA GTC GTC TGA CTA
Cys Asn Pro Met Asp Ile Thr Leu Tyr Tyr Gln Gln Thr Asp>

590            600            610            620            630
       *              *              *              *              *
GAA GCA AAT AAA TCG ATA TGG ACG GGC TCT TCT TGC ACG GTT AAA
CTT CGT TTA TTT AGC TAT ACC TGC CCG AGA ACG TGC CAA TTT
Glu Ala Asn Lys Ser Ile Trp Thr Gly Ser Ser Cys Thr Val Lys>

640            650            660            670
       *              *              *              *
GTG TGT CCA TTA AAT ACA CAA ACA CTT GGT ATT GGA TGT CTA ATA
CAC ACA GGT AAT TTA TGT GTT GAA CCA TAA CCT ACA GAT TAT
Val Cys Pro Leu Asn Thr Gln Thr Leu Gly Ile Gly Cys Leu Ile>
```

Fig. 5C

```
     680         690         700         710         720
      *           *           *           *           *
ACT AAT CCA GAC ACG TTT GAA ACA GTT GCG ACA ATG GAG AAG TTA
TGA TTA GGT CTG TGC AAA CTT TGT CAA CGC TGT TAC CTC TTC AAT
Thr Asn Pro Asp Thr Phe Glu Thr Val Ala Thr Met Glu Lys Leu>

730         740         750         760
      *           *           *           *
GTG ATT ACA GAT GTT GTA CAT CTA CCA CAG GTC AAT CAC AAA TTA AAC GTC
CAC TAA TGT CTA CAA CAT GTA GAT GGT GTC TTA GTG TTT AAT TTG CAG
Val Ile Thr Asp Val Val Asp Gly Val Asn His Lys Leu Asn Val>

770         780         790         800         810
      *           *           *           *           *
ACA ACG GCA ACG TGC ACC ATA CGC AAC TGT AAA TTT TTC ACA AAG TTA GGA CCA
TGT TGC CGT TGC ACG TGG TAT GCG TTG ACA TTT AAA AAG TGT TTC AAT CCT GGT
Thr Thr Ala Thr Cys Thr Ile Arg Asn Cys Lys Lys Leu Gly Pro>

820         830         840         850
      *           *           *           *
AGG GAG AAC GTA GCA GTC ATA CAG GTA CAG GGC GGC AAC ATT TTA
TCC CTC TTG CAT CGT CAG TAT GTC CAT GTC CCG CGC TTG TAA AAT
Arg Glu Asn Val Ala Val Ile Gln Val Gly Ala Asn Ile Leu>

860         870         880         890         900
      *           *           *           *           *
GAC ATC ACA GCT GAT CCA ACA ACT ACA CCA CAG ACA GAG ACA ATG
CTG TAG TGT CGA CTA GGT TGT TGA TGT GGT GTC TGT CTC TGT TAC
Asp Ile Thr Ala Asp Pro Thr Thr Thr Pro Gln Thr Glu Thr Met>
```

Fig. 5D

```
                910                 920                 930                 940
                 *                   *                   *                   *
ATG CGA ATA AAT TGG AAA AAA TGG TGG CAA GTC TTT TAC ACG GTA
TAC GCT TAT TTA ACC TTT TTT ACC ACC GTT CAG AAA ATG TGC CAT
Met Arg Ile Asn Trp Lys Lys Trp Trp Gln Val Phe Tyr Thr Val>

950                 960                 970                 980                 990
           *                   *                   *                   *                   *
GTG GAT TAC GTC AAT CAG ATA ATT CAG ACA ATG TCC AAA AGA TCT
CAC CTA ATG CAG TTA GTC TAT TAA GTC TGT TAC AGG TTT TCT AGA
Val Asp Tyr Val Asn Gln Ile Ile Gln Thr Met Ser Lys Arg Ser>

1000                1010                1020                1030
           *                   *                   *                   *
ACA TCG CTT AAT TCG TCG GCG TTC TAC TAT AGA GTG TAG GTG CAT
TGT AGC GAA TTA AGC AGC CGC AAG ATG ATA TCT CAC ATC CAC GTA
Thr Ser Leu Asn Ser Ser Ala Phe Tyr Tyr Arg Val 1040                1050                1060
           *                   *                   *
GCT AGA TTA GAG TTG TAT GAT GTG ACC
CGA TCT AAT CTC AAC ATA CTA CAC TGG
```

Fig. 5E

```
Sequence Range: 1 to 354

10         20         30         40         50
                         *          *          *          *          *
Translatio   GFKSE NFRLA SG*LL LMYGI EYTTI LIFLT SITLL NYILK SITRI MDYII
             10    25    40    55    70    85    100   115   130   145
ROTVP7       kiKrE NFRLA SG*LL LMYGI EYTTv LtFLi StiLL NYILK SITRI MDfII>
[ 1586 ]     v^    ^^^^^ ^^v^^ ^^^^^ ^^^^v ^v^^v ^v^^^ ^^^^^ ^^^^^ ^^v^^

10    25    40    55    70    85    100   115   130   145
RORVP7       GFKSE NFRLA SG*LL LMYGI EYTTv LtFLi SlilL NYILK SlTRm MDcII>
[ 1574 ]     ^^^^^ ^^^^^ ^^^^^ ^^^^^ ^^^^v ^v^^v ^v^^^ ^^^^^ ^^^^v ^^v^^

10    25    40    55    70    85    100   115   130   145
PRVOSUVP7    GFKrE NFRLA iG*LL LMYGI EYTTv LtFLi slvfv NYILK SvTRt MDfII>
[ 1558 ]     ^^^v^ ^^^^^ v^^^^ ^^^^^ ^^^^v ^v^^v vvvv  ^^^^^ ^^^^v ^^v^^

10    25    40    55    70    85    100   115   130   145
ROHVP7A      GFKrE NFRLA nG*LL LMYGI EYTTI LIFLi SIilL NYILK SvTRI MDYII>
[ 1544 ]     ^^^v^ ^^^^^ v^^^^ ^^^^^ ^^^^^ ^^^^v ^v^^^ ^^^^^ ^^^^v ^^^^^

10    25    40    55    70    85    100   115   130   145
PRVPRVP7G    GFKrE NFRLA SG*LL LMYGI EYTTv LlyLi SfvLm sYILK tITkm MDYII>
[ 1510 ]     ^^^v^ ^^^^^ ^^^^^ ^^^^^ ^^^^v ^v^v^ ^vv^v v^^^^ v^^vv ^^^^^

995   980   965   950   935   920   905
ROB7         <flfek lhps

```
                        60         70         80         90        100
                         *          *          *          *          *
Translatio  YRFLL IVVIL ATIIN AQNYG VNLPI TGSMD TAYAD STQSE PFLTS TLCLY ROTVP7       160   175   190   205   220   235   250   265   280   295
[ 1586 ]    YRFLf IiVIL spflr AQNYG iNLPI aGSMD TAYAn STQeE PFLTS TLCLY>
            ^^^^^  ^^^^       ^^^^^ ^^^^^ ^ ^^^ ^^^^  ^^^ ^ ^^^^^ ^^^^^

RORVP7       160   175   190   205   220   235   250   265   280   295
[ 1574 ]    YRFLf IVVIL spllk AQNYG iNLPI TGSMD TAYAn STQeE tFLTS TLCLY>
            ^^^^^ ^^^^^       ^^^^^ ^^^^^ ^^^^^ ^^^^  ^^^ ^  ^^^^ ^^^^^

PRVOSUVP7    160   175   190   205   220   235   250   265   280   295
[ 1558 ]    YRFLL viVvL AplIk AQNYG iNLPI TGSMD TpYmn STtSE tFLTS TLCLY>
            ^^^^^ ^ ^ ^ ^ ^^  ^^^^^ ^^^^^ ^^^^^ ^ ^   ^^ ^^  ^^^^ ^^^^^

ROHVP7A      160   175   190   205   220   235   250   265   280   295
[ 1544 ]    YRFLL ItVaL faltr AQNYG lNLPI TGSMD avYtn STQeE vFLTS TLCLY>
            ^^^^^ ^ ^ ^    ^  ^^^^^ ^^^^^ ^^^^^  ^^   ^^^ ^  ^^^ ^^^^^

PRVPRVP7G    160   175   190   205   220   235   250   265   280   295
[ 1510 ]    YRitf IiVvL svlsN AQNYG iNLPI TGSMD TAYAn STQdn nFLsS TLCLY>
            ^^ ^^ ^ ^ ^       ^^^^^ ^^^^^ ^^^^^ ^^^^  ^^^    ^^ ^ ^^^^^

ROB7         890   875
[   53 ]    <qeyyL vsl
              v ^   ^ ^

PRVPRVVP7    105
[   36 ]    l-FLL IV>
                  ^^
```

Fig. 6B

```
                       110        120        130        140        150
                        *          *          *          *          *
Translatio  YPVEA SNEIA DTEWK DTLSQ LFLTK GWPTG SVYLK EYADI AAFSV EPQLY 310   325   340   355   370   385   400   415   430   445
ROTVP7      YPtEA atEIn DnsWK DTLSQ LFLTK GWPTe SVYfK EYtnI AsFSV dPQLY>
[ 1586 ]    ^^ ^^ ^ ^^^ ^ ^^^ ^^^^^ ^^^^^ ^^^^  ^^^^^ ^ ^ ^ ^ ^^^ ^^^^^

310   325   340   355   370   385   400   415   430   445
RORVP7      YPtEA atEIn DnsWK DTLSQ LFLTK GWPTG SVYfK EYtDI AsFSV dPQLY>
[ 1574 ]    ^^ ^^ ^ ^^^ ^ ^^^ ^^^^^ ^^^^^ ^^^^^ ^^^^^ ^ ^ ^ ^ ^^^ ^^^^^

310   325   340   355   370   385   400   415   430   445
PRVOSUVP7   YPnEA atEIA DTkWt eTLSQ LFLTK GWPTG SVYfK gYADI AsFSV EPQLY>
[ 1558 ]    ^^ ^^ ^ ^^^ ^^ ^  ^^^^^ ^^^^^ ^^^^^ ^^^^^ ^ ^^^ ^ ^^^ ^^^^^

310   325   340   355   370   385   400   415   430   445
ROHVP7A     YPtEA StgIn DgdWK DsLSQ mFLTK GWPTG SVYfK EYsnI vdFSV dPQLY>
[ 1544 ]    ^^ ^^ ^^ ^  ^ ^^^ ^ ^^^ ^^^^^ ^^^^^ ^^^^^ ^^ ^  ^ ^^^ ^^^^^

310   325   340   355   370   385   400   415   430   445
PRVPRVP7G   YPsEA ptqIn DnEWK DTLSQ LFLTK GWPTG SVYfn EYsnv leFSi dPkLh>
[ 1510 ]    ^^ ^^ ^^^^^ ^^^^^ ^^^^^ ^^^^^ ^^^^^ ^^^^  ^^^^  ^     ^^ ^^

160        170        180        190        200
                        *          *          *          *          *
Translatio  CDYNL VLMKY DSTQE LDMSE LADLI LNEWL CNPMD ITLYY YQQTD EANKS
```

Fig. 6C

```
ROTVP7       460        475        490        505        520        535        550        565        580        595
[ 1586 ]     CDYNv      VLMKY      DaTlq      LDMSE      LADLI      LNEWL      CNPMD      ITLYY      YQQTD      EANKw>
             ^^^^^      ^^^^^      ^ ^v^       ^^^^^      ^^^^^      ^^^^^      ^^^^^      ^^^^^      ^^^^^      ^^^^v

RORVP7       460        475        490        505        520        535        550        565        580        595
[ 1574 ]     CDYNv      VLMKY      DaTlq      LDMSE      LADLI      LNEWL      CNPMD      IaLYY      YQQTD      EANKw>
             ^^^^^      ^^^^^      ^ ^v^       ^^^^^      ^^^^^      ^^^^^      ^^^^^      ^ ^^^      ^^^^^      ^^^^v

PRVOSUVP7    460        475        490        505        520        535        550        565        580        595
[ 1558 ]     CDYNi      VLMKY      Dgnlq      LDMSE      LAgLI      LNEWL      CNPMD      ImLYY      YQQTD      EANKw>
             ^^^^^      ^^^^^      ^   v^      ^^^^^      ^^ ^^      ^^^^^      ^^^^^      ^ ^^^      ^^^^^      ^^^^v ROHVP7A      460        475        490        505        520        535        550        565        580        595
[ 1544 ]     CDYNL      VLMKY      Dqslk      LDMSE      LADLI      LNEWL      CNPMD      vTLYY      YQQsg      EsNKw>
             ^^^^^      ^^^^^      ^    v      ^^^^^      ^^^^^      ^^^^^      ^^^^^      ^^^^^      ^^^        ^  ^v PRVPRVP7G    460        475        490        505        520        535        550        565        580        595
[ 1510 ]     CDYNi      VLirf      aSgeE      LDiSE      LADLI      LNEWL      CNPMD      ITLYY      YQQTg      EANKw>
             ^^^^^      ^^  ^      ^^         ^^ ^^      ^^^^^      ^^^^^      ^^^^^      ^^^^^      ^^^^       ^^^^v Translatio              210        220        230        240        250
                        *          *          *          *          *
             IWTGS      SCTVK      VCPLN      TQTLG      IGCLI      TNPDT      FETVA      TMEKL      VITDV      VDGVN ROTVP7       610        625        640        655        670        685        700        715        730        745
[ 1586 ]     IsmGS      SCTiK      VCPLN      TQTLG      IGCLt      TdatT      FEeVp      TaEKL      VITDV      VDGVN>
             ^v ^^      ^^ ^^      ^^^^^      ^^^^^      ^^^^       ^^  ^      ^^ ^       ^ ^^^      ^^^^^      ^^^^^

RORVP7       610        625        640        655        670        685        700        715        730        745
[ 1574 ]     IsmGS      SCTiK      VCPLN      TQTLG      IGCLt      TdtaT      FEeVA      TaEKL      VITDV      VDGVN>
             ^v ^^      ^^ ^^      ^^^^^      ^^^^^      ^^^^       ^^  ^      ^^ ^^      ^ ^^^      ^^^^^      ^^^^^
```

Fig. 6D

```
PRVOSUVP7     610   625   640   655   670    685   700   715   730   745
[ 1558 ]      IsmGt SCTiK VCPLN TQTLG IGCst  Tdins FETVA naEKL aITDV VDGVN>
              ^v ^  ^^^^^ ^^^^^ ^^^^^ ^^^v   ^^v^  ^^^^^   ^^^  ^^^^ ^^^^^

ROHVP7A       610   625   640   655   670    685   700   715   730   745
[ 1544 ]      IsmGS SCTVK VCPLN TQTLG IGCqt  TNvDs FEmiA enEKL aIvDV VDGiN>
              ^v ^^ ^^^^^ ^^^^^ ^^^^^ ^^^v   ^^ ^  ^^ ^^ v^^^   ^ ^^ ^^^^^

PRVPRVP7G     610   625   640   655   670    685   700   715   730   745
[ 1510 ]      IsmGS SCTVK VCPLN TQTLG IGCqt  TNtaT FETVA dsEKL aIvDV VDsVN>
              ^v ^^ ^^^^^ ^^^^^ ^^^^^ ^^^v   ^^  ^ ^^^^^ v^^^   ^ ^^ ^^ ^^

260         270         280         290         300
                           *           *           *           *           *
Translatio    HKLNV TTATC TIRNC KKLGP RENVA VIQVG GANIL DITAD PTTTP QTETM ROTVP7        760   775   790   805   820   835   850   865   880   895
[ 1586 ]      HKLdV TTATC TIRNC KKLGP RENVA VIQVG GsdIL DITAD PTTaP QTErM>
              ^^^^^ ^^^^^ ^^^^^ ^^^^^ ^^^^^ ^^^^^ ^ ^^^ ^^^^^ ^^^ ^ ^^^ ^

RORVP7        760   775   790   805   820   835   850   865   880   895
[ 1574 ]      HKLdV TTATC TIRNC KKLGP RENVA VIQVG GsdvL DITAD PTTaP QTErM>
              ^^^^^ ^^^^^ ^^^^^ ^^^^^ ^^^^^ ^^^^^ ^ ^^^ ^^^^^ ^^^ ^ ^^^ ^

PRVOSUVP7     760   775   790   805   820   835   850   865   880   895
[ 1558 ]      HKLdV TTsTC TIRNC KKLGP RENVA VIQVG GpNIL DITAD PTTaP QTErM>
              ^^^^^ ^^ ^^ ^^^^^ ^^^^^ ^^^^^ ^^^^^ ^ ^^^ ^^^^^ ^^^ ^ ^^^ ^

ROHVP7A       760   775   790   805   820   835   850   865   880   895
[ 1544 ]      HKiNl TTtTC TIRNC KKLGP RENVA VIQVG GsNvL DITAD PTTnP QTErM>
              ^^^^^ ^^ ^^ ^^^^^ ^^^^^ ^^^^^ ^^^^^ ^ ^^^ ^^^^^ ^^^ ^ ^^^ ^
```

Fig. 6E

```
                    760      775   790   805   820   835   850   845   880   895
PRVPRVP7G           HKLdV    TstTC TIRNC nKLGP RENVA iIQVG GsNIL DITAn PTTsP QTErM>
[ 1510 ]            ^^^^^    ^^    ^^^^^ ^^^^^ ^^^^^ ^^^^^ ^^^^^ ^^^^^ ^^^^  ^

310         320         330         340         350
                              *           *           *           *           *
Translatio          MRINW VFYTV VDYVN QIIQT MSKRS TSLNS SAFYY RV*VH ARLEL 910      925   940   955   970   985   1000  1015  1030  1045
ROTVP7              MRINW    KKWWQ VFYTV VDYVd QIIQv MSKRS rSLNS aAFYY RV*V* lRLEL>
[ 1586 ]            ^^^^^    ^^^^^ ^^^^^ ^^^^^ ^^^^  ^^^^^ ^^^^^ ^^^^  ^^^^v v^^^^

910      925   940   955   970   985   1000  1015  1030  1045
RORVP7              MRINW    KKWWQ VFYTV VDYVN QIIQa MSKRS rSLNS aAFYn Ri*V* lwiEm>
[ 1574 ]            ^^^^^    ^^^^^ ^^^^^ ^^^^^ ^^^^  ^^^^^ ^^^^^ ^^^^  ^^v^v v^^^^

910      925   940   955   970   985   1000  1015  1030  1045
PRVOSUVP7           MRINW    KrWWQ VFYTi VDYVN QIvQv MSKRS rSLdS aAFYY RV*iy lkLEL>
[ 1558 ]            ^^^^^    ^^^^^ ^^^^^ ^^^^^ ^^^^  ^^^^^ ^^^^^ ^^^^  ^^v^  v^^^^

910      925   940   955   970   985   1000  1015  1030  1045
ROHVP7A             MRvNW    KKWWQ VFYTi VDYiN QIvQv MSKRS rSLNS aAFYY RV-*y lRLEL>
[ 1544 ]            ^^^^^    ^^^^^ ^^^^^ ^^^^^ ^^^^  ^^^^^ ^^^^^ ^^^^  ^^

Translatio YDVT

ROTVP7      YDV>
[ 1586 ]    ^^^

RORVP7      1060
[ 1574 ]    YDVT>
            ^^^^

PRVOSUVP7   1060
[ 1558 ]    YDVT>
            ^^^^

ROHVP7A     fDVT>
[ 1544 ]    ^^^^

PRVPRVP7G   1060
[ 1510 ]    YDVT>
            ^^^^

Fig. 6G

ASSEMBLED VIRAL PARTICLES AND THEIR USE IN A VACCINE TO ROTAVIRAL DISEASE

TECHNICAL FIELD

The present invention relates generally to virus-like particles which are useful as vaccines and immunogens. In particular, the instant invention concerns assembled rotaviral structural proteins and the use of the assembly in preventing and ameliorating rotaviral infection.

BACKGROUND OF THE INVENTION

Rotaviruses cause gastrointestinal disorders and diarrhea in a wide variety of avian and mammalian species, including man. Several serotypes of rotavirus have been identified, four of which (serotypes 1 to 4) are found in humans and five of which (serotypes 3 to 7) are found in other animals. Recent studies indicate that cross protection among strains belonging to different serotypes may occur in animals including man. Ijaz et al., *J Virol* (1990) (In Press); Flores et al., *J Clin Microbiol* (1989) 27:512-518. The rotavirus genome is thought to consist of eleven segments of double-stranded RNA. The eleven genes encode the production of at least six structural proteins of the virus. In complete virus particles, these six proteins occur in a double-shelled arrangement. The outer shell or capsid is comprised of three proteins—virus protein 7 (VP7), virus protein 4 (VP4), and a third protein which has not yet been well characterized. There are three inner shell proteins designated virus protein 1 (VP1), virus protein 2 (VP2), and virus protein 6 (VP6).

VP7 is the major outer shell glycoprotein with an approximate molecular mass of 38 kD in its unreduced form (as determined by SDS-PAGE) and 42 kD in its reduced form (as determined by SDS-PAGE). VP7 has approximately 325 amino acids. The amino acid sequence of several rotavirus isolates has been determined and the sequences are approximately 75 to 86% homologous. Regions of conservation among human and animal species have been reviewed by Estes, M. K. et al., *Microbiol Rev* (1989) 53:410-449. This protein is known to bind to host cells (Sabara, M. et al., *J Virol* (1985) 53:58-66). Epitope mapping of VP7 using neutralizing monoclonal antibodies has localized a neutralizing-absorption domain to a component peptide with an approximate molecular mass of 14 kD (Sabara, M. et al., supra). Synthetic peptides derived from within this 14 kD fragment have also been shown to neutralize viral infectivity (Ijaz et al., supra).

A second outer capsid protein, VP4 (formerly designated VP3), is composed of 776 amino acids and has an approximate molecular mass of 82 kD in its unreduced form and 84 kD in its reduced form. The sequence of bovine VP4 has been determined (Potter, A. A. et al., *Nucl Acid Res* (1987) 15:4361) as has the partial amino acid sequence for simian VP4 (Mackow, et al., *Proc Natl Acad Sci USA* (1988) 85:645-649. VP4 possesses hemagglutinating activity, and induces the production of neutralizing antibodies which provide heterotypic passive protection in vivo (Offit, P. A. et al., *J Virol* (1986) 58:700-703). VP4 is responsible, in combination with VP7, in determining virus serotype.

Dimers of VP4 combine to form the surface spikes of rotavirus that extend distally from the rotavirus outer shell. VP4 is important in the penetration of the virus into the host cell and infectivity is increased by the cleavage of VP4 by trypsin. Trypsin enhanced infectivity is a common feature of all rotaviruses and the cleavage site for trypsin is also conserved as reviewed in Estes et al. (supra).

The inner capsid of rotavirus includes at least three proteins designated VP1, VP2 and VP6. Of interest herein is VP6 which is a 45 kD protein. Bovine VP6 appears to exist in trimeric units in both the virus particle and in infected cells, with the intersubunit linkage consisting of noncovalent interactions. These trimeric units complex further by virtue of disulfide bridges into larger units which likely represent the ring-like structures observed by several investigators using electron microscopy.

VP6 has been identified as the subgroup antigen and has also been described as the common rotavirus group antigen since some monoclonal antibodies raised against this protein react with all rotaviruses and polyclonal serum raised against a single rotavirus type can detect most other rotavirus strains. In addition to its antigenic properties, this nucleocapsid protein is extremely immunogenic and several investigators have found that the antibody raised to this protein has neutralizing ability. (See, e.g. Offit, et al., *J Virol* (1986) 58:700-703).

VP6 is an effective carrier protein (Redmond, M. J., et al. *Mol Immunol* (1990) (In Press) and VP4 is able to associate with VP6 monomeric and oligomeric protein units. (Redmond, M. J., et al. supra). The VP4-VP6 association has been shown to withstand harsh treatment such as boiling in SDS. Additionally, VP6 is capable of forming particles in vitro with VP2 and VP7 using a calcium dependent process (Ready, K. F. M., et al., *Virology* (1988) 167:269-273). The resulting assembly is immunoreactive with antibodies specific for the whole virus as well as for immunodominant sites on VP6 and VP7 and this immunoreactivity is equivalent to that of native bovine rotavirus (BRV). (Ready, K. F. M., et al., supra).

The present invention provides assembled viral particles including peptides or proteins corresponding to VP7 and/or VP4, or immunogenic regions thereof, in combination with VP6. These assembled particles are effective as vaccines and in eliciting the production of neutralizing antibodies. Such a vaccine provides an alternative to the use of a live attenuated virus vaccine.

DISCLOSURE OF THE INVENTION

The instant invention is based on the discovery that certain viral peptides, or epitopic regions thereof, when assembled into a viral particle, are able to elicit an immune response in a subject treated therewith. Vaccines including these assemblies are safer and more practical than those composed of attenuated virus.

Accordingly, in one aspect, the invention is directed to a viral particle assembly capable of eliciting an immunological response in a vertebrate subject. The viral particle assembly comprises:

(a) an inner capsid protein substantially homologous and functionally equivalent to VP6; and (b) one or more outer capsid proteins selected from the group consisting of (i) a protein substantially homologous and functionally equivalent to VP4, or a functional fragment thereof, and (ii) a protein substantially homologous and functionally equivalent to VP7.

In another embodiment, the present invention is directed to a viral particle assembly capable of eliciting an immunological response in a vertebrate subject wherein the viral particle assembly comprises VP6 assembled with VP4 and VP7.

In yet further embodiments, the invention is directed to vaccine compositions including a pharmaceutically acceptable vehicle and the viral particle assemblies described above.

In other embodiments, the instant invention is directed to methods of treating and preventing rotaviral disease in a vertebrate subject using the above vaccine compositions.

These and other embodiments of the present invention will readily occur to those of ordinary skill in the art in view of the disclosure herein.

BRIEF DESCRIPTION OF THE FIGURES

FIGS. 1A-D show the nucleotide sequence and the predicted amino acid sequence of the VP6 protein of strain C486 (bovine).

FIGS. 2A-F compare the amino acid sequence of rotavirus VP6 derived from several strains: Bovine RF rotavirus (ROBMCP), human 1076 rotavirus (RO1HVP6), rotavirus segment 6 inner shell protein VP6 RNA (RO1S2VP6), equine H2 rotavirus (RO1VVP6H2), equine FI14 rotavirus (RO1VVP6F1), human Wa rotavirus (RO2SEG6), porcine Gottfried rotavirus (RO1PVP6), porcine group C rotavirus (PRVVP6), and simian SA11 rotavirus (ROTG6A).

FIG. 3 compares the amino acid sequence of rotavirus VP4 derived from several strains: K8, KU, DS1, M37, ST3, SA11, and RRV.

FIGS. 4A-F show the nucleotide sequence and corresponding amino acid sequence of the VP4 protein from strain C486 (bovine).

FIGS. 5A-C depict the nucleotide sequence and corresponding amino acid sequence of the VP7 protein from strain C486 (bovine)

FIGS. 6A-D compare the amino acid sequence of rotavirus VP7 derived from several strains: simian 11 rotavirus (ROTVP7), rhesus rotavirus (RORVP7), porcine OSU rotavirus (PRVOSUVP7), human rotavirus (ROHVP7A), porcine Gottfried rotavirus (PRVPRVP7G), bovine uk rotavirus (ROB7), and porcine major C rotavirus (PRVPRVVP7).

DETAILED DESCRIPTION

Figure 7:
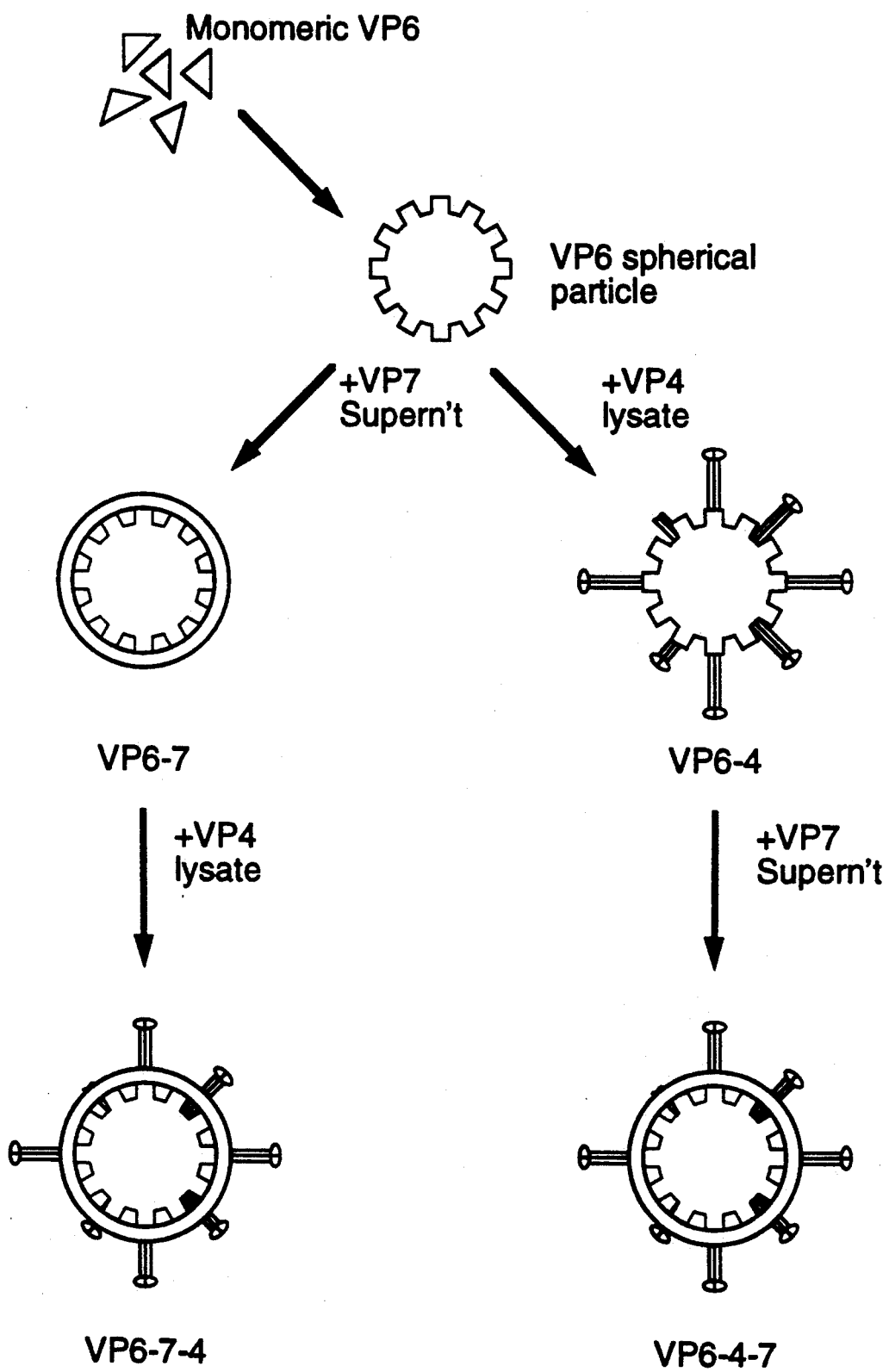
FIG. 7 is a graphic representation of the production of in vitro assembled rotavirus particles.

The practice of the present invention will employ, unless otherwise indicated, conventional techniques of immunology, protein chemistry, molecular biology, microbiology and recombinant DNA technology, which are within the skill of the art. Such techniques are explained fully in the literature. See, e.g., *Handbook of Experimental Immunology*, Vols. I-IV (D. M. Weir and C. C. Blackwell eds., 1986, Blackwell Scientific Publications); *Methods in Enzymology* (S. Colowick and N. Kaplan eds., Academic Press, Inc.); Sambrook, Fritsch & Maniatis, *Molecular Cloning: A Laboratory Manual* 2d Edition (Cold Spring Harbor Laboratory Press, 1989); *Oligonucleotide Synthesis* (M. J. Gait ed., 1984); and *DNA Cloning*, Volumes I and II (D. N. Glover, ed., 1985).

All patents, patent applications, and publications mentioned herein, whether supra or infra, are hereby incorporated by reference.

A. Definitions

In describing the present invention, the following terms will be employed, and are intended to be defined as indicated below.

By "VP6" is meant the art-recognized major viral protein of the inner capsid from any species or strain within the family Reoviridae. See, e.g., Kapikian, et al., in *Virology* (B. N. Fields et al., eds., 1988). Examples of rotavirus strains from which the VP6 protein can be isolated and employed in the present invention include, but are not limited to, Simian SA11, human D rotavirus, bovine UK rotavirus, human Wa or W rotavirus, human DS1 rotavirus, rhesus rotavirus, the "O" agent, bovine NCDV rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU1 rotavirus, feline Taka rotavirus, equine H2 rotavirus, human St. Thomas No. 3 and No. 4 rotaviruses, human Hosokawa rotavirus, human Hochi rotavirus, porcine SB2 rotavirus, porcine Gottfried rotavirus, porcine SB1A rotavirus, porcine OSU rotavirus, equine H1 rotavirus, chicken Ch.2 rotavirus, turkey Ty.1 rotavirus, bovine C486 rotavirus, and strains derived therefrom. Thus VP6 for use in the present invention includes VP6 from any rotavirus strain, whether from subgroup I, subgroup II, or any as yet unidentified subgroup, as well as from any of the serotypes 1-7, as well as any as yet unidentified serotypes.

The VP6 protein comprises an amino acid sequence of rotavirus which is unique to the class, or any member of the class, of VP6 polypeptides. A representative nucleotide sequence and the deduced amino acid sequence of bovine recombinant (BR) VP6 strain C486 is shown in FIG. 1. FIG. 2 shows the amino acid sequence of several different strains of rotavirus. As can be seen, extensive homology is present between the depicted rotavirus strains. Other VP6 nucleotide and amino acid sequences will find use in the instant invention, the depicted sequences only being representative of already known VP6 sequences.

By "VP4" is meant an art-recognized viral protein of the outer capsid from any species or strain within the family Reoviridae. Examples of rotavirus strains from which the VP4 protein can be isolated and employed in the present invention include, but are not limited to, those described above with reference to VP6.

VP4 (formerly designated VP3), is composed of 776 amino acids. The amino acid sequence of VP4 derived from strains K8, KU, DS1, M37, ST3, SA11, and RRV is shown in FIG. 3. The nucleotide sequence and deduced amino acid sequence of VP4 from strain C486 (bovine) is shown in FIG. 4. Again, other sequences will find use herein.

By "VP7" is meant the art-recognized major viral protein of the outer capsid from any species or strain within the family Reoviridae. Examples of rotavirus strains from which the VP7 protein can be isolated and employed in the present invention include, but are not limited to, those described above with reference to VP6.

VP7 is composed of approximately 325 amino acids and the nucleotide sequence and deduced amino acid sequence of VP7 from strain C486 (bovine) is shown in FIG. 5. Arias et al., *J Virol* (1984) 50:657-661 describes the nucleotide sequence of VP7 from simian SA11. FIG. 6 depicts the amino acid sequences of several rotavirus strains. VP7 shows serotype restricted homology. The above sequences are meant to be representative and nonlimiting. Therefore, other functional sequences may also be employed with the present invention.

Two DNA or protein sequences are "substantially homologous" when at least about 85% (preferably at least about 90%, and most preferably at least about 95%) of the nucleotides or amino acids match over a defined length of the molecule. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra.

The term "functionally equivalent" refers to sequences of an analog of an outer or inner capsid rotavirus protein which define a chain that will produce a protein that elicits an immunological response equivalent to that elicited by the native sequence. Thus, the rotavirus proteins utilized herein need have the identical amino acid sequence of the native proteins.

A "functional fragment" of a rotavirus protein is a fragment with the capability of raising an immunological response equivalent to that elicited by the full sequence. It has been demonstrated that the distal end of VP4 is involved in the initial attachment of the virion to the cell, since infection may be blocked by monoclonal antibodies to this region. Furthermore, the enzyme trypsin enhances virus infectivity. This enhancement appears to act after adsorption, since trypsin does not affect the efficiency or rate of virus attachment to cells but does increase the levels of uncoated particles found in cells. The molecular mechanism for trypsin enhanced infectivity occurs via the cleavage of the VP4 protein into two fragments with approximate molecular weights of 28 kDa and 60 kDa, respectively. Therefore, the trypsin cleavage site of VP4 is important in rotavirus replication. Thus, fragments consisting of an amino acid sequence substantially homologous to at least the first 255 N-terminal amino acids, as depicted in FIG. 4, and which include the trypsin cleavage site, will also find use in the instant invention so long as these fragments are capable of raising an immunological response as defined above.

"A viral particle assembly" refers to an association between outer and inner capsid proteins of rotavirus, or proteins substantially homologous and functionally equivalent thereto, or functional fragments thereof. The particles can be assembled in vitro, as described more fully below, to resemble double shelled rotavirus.

The term "epitope" refers to the site on an antigen or hapten to which a specific antibody molecule binds. The term is also used interchangeably with "antigenic determinant" or "antigenic determinant site."

An "immunological response" to a composition or vaccine is the development in a vertebrate subject of a cellular and/or antibody mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

An "immunogenic protein" is a protein which elicits an immunological response in a subject to which it is administered.

The terms "polypeptide" and "protein" are used interchangeably herein and are used in their broadest sense, i.e., to denote any polymer of amino acids (dipeptide or greater) linked through peptide bonds. Thus, the terms encompass oligopeptides, protein fragments, analogs, mutants, fusion proteins and the like.

"Native" proteins or polypeptides refer to proteins or polypeptides recovered from rotavirus or from rotavirus infected cells. Thus the term includes naturally occurring rotavirus proteins and fragments thereof. "Non-native" polypeptides refer to polypeptides that have been produced by recombinant DNA methods or by direct synthesis. "Recombinant" polypeptides refer to polypeptides produced by recombinant DNA techniques; i.e., produced from cells transformed by an exogenous DNA construct encoding the desired polypeptide.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about the replication and/or expression of the attached segment. An "expression vector" refers to a vector capable of autonomous replication or integration and contains control sequences which direct the transcription and translation of the desired DNA sequence in an appropriate host.

A "coding sequence" is a polynucleotide sequence which is transcribed and/or translated into a polypeptide.

A "promoter sequence" is a DNA regulatory region capable of binding RNA polymerase and initiating transcription of a downstream (i.e., in the 3' direction) coding sequence.

A coding sequence is "under the control" of the promoter sequence in a cell when transcription of the coding sequence results from the binding of RNA polymerase to the promoter sequence; translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence.

"Control sequences" refers to those sequences which control the transcription and/or translation of the coding sequence(s); these may include, but are not limited to, promoter sequences, transcriptional initiation and termination sequences, and translational initiation and termination sequences. In addition, "control sequences" refers to sequences which control the processing of the polypeptide encoded within the coding sequence; these may include, but are not limited to sequences controlling secretion, protease cleavage, and glycosylation of the polypeptide.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell.

A "host cell" is a cell which has been transformed, or is capable of transformation, by an exogenous DNA sequence.

A cell has been "transformed" by exogenous DNA when such exogenuus DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

A "vaccine composition," according to the present invention, is an otherwise conventional vaccine formulation employing either the viral particle assemblies alone or in combination with one or more unassembled purified viral proteins or with cell lysates having one or more of the individual outer and/or inner capsid proteins. Particularly useful is the addition of a crude cell lysate containing VP4 to the instant vaccine compositions. The preparation of vaccines containing the above active ingredients is well understood in the art. Typically, vaccines are prepared as injectables, either as liquid solutions or suspensions; solid forms suitable for solution in, or suspension in, liquid prior to injection may also be prepared. The preparation may also be emulsified or the active ingredient encapsulated in liposomes. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Injectable vaccine formulations will contain an effective amount of the active ingredient, the exact amount being readily determined by one skilled in the art. The active ingredient can range from about 0.01% to about 95% (w/w) of the injectable composition, or even higher or lower if appropriate.

Additional vaccine formulations which are suitable for other modes of administration include suppositories and, in some cases, oral formulation. For suppositories, the vaccine composition will include traditional binders and carriers, such as polyalkaline glycols, or triglycerides. Such suppositories may be formed from mixtures containing the active ingredient in the range of about 0.5% to about 10% (w/w), preferably about 1% to about 2%. Oral formulations include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Furthermore, the viral particles may be formulated into vaccine compositions in either neutral or salt forms. If salts are used, the final preparation will typically contain less than 0.15M salt. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, or ferric hydroxides, and such organic bases as isopropylamine, trimethylamine, 2-ethylaminoethanol, histidine, procaine, and the like.

By "treating" is meant curing or ameliorating a subject that has contracted a rotaviral infection. "Preventing" rotaviral disease means preventing the occurrence of the infection, or tempering the severity of the infection if it is contracted subsequent to the administration of the instant compositions.

The vaccine composition of the present invention may be administered in a manner compatible with the dosage formulation, and in such amounts as will be therapeutically effective and immunogenic. A "therapeutically effective amount" of a vaccine composition is a dose sufficient to either prevent or treat rotaviral infection in a subject to which the composition is administered. The dosages of the viral particle assemblies which can treat or prevent rotaviral infection can be determined in view of this disclosure by one of ordinary skill in the art by running routine trials with appropriate controls. Comparison of the appropriate treatment groups to the controls will indicate whether a particular dosage is effective in preventing or treating a disease used in a controlled challenge. In general, effective dosage will vary depending on the mode of administration. For example, in the case of an intramuscular injection, generally from 0.001 µg/kg to 10 µg/kg will find use in the instant invention.

B. General Methods

Central to the instant invention is the discovery that assembled viral particles comprising rotavirus inner and outer capsid proteins, are able to elicit an immune response in a subject to which they are administered. The viral particles are assemblies of inner and outer capsid proteins of rotavirus. Particularly useful is a viral particle assembly including the inner capsid protein, VP6, with either or both of the outer capsid proteins, VP4 and VP7. VP6 appears to act as a "carrier" for the two outer capsid proteins, as described more fully below. These assemblies can be used alone, or in combination with unassembled, outer capsid proteins, provided as purified or partially purified proteins, or crude cell lysates, in a vaccine composition for the treatment and/or prevention of rotaviral infection.

The inner and outer capsid proteins for use in the viral particles of the instant invention can be prepared by any of several methods. First, the individual proteins can be isolated by successive degradation of purified virus with EDTA and either calcium chloride (CaCl$_2$) or lithium chloride (LiCl) treatment by standard techniques. See, e.g., Almeida et al., *J Med Virol* (1979) 4:269-277; Bican et al., *J Virol* (1982) 43:1113-1117; Gorziglia et al., *J Gen Virol* (1985) 66:1889-1900; Ready et al., *Virology* (1987) 157:189-198. Alternatively, the viral proteins can be produced by recombinant DNA techniques, which are fully explained in the literature. See, e.g., Sambrook et al., supra; and *DNA Cloning*, supra.

DNA coding sequences encoding the viral polypeptides can be derived from the particular mRNA. See, e.g., Estes et al., supra; Both et al., *J Virol* (1984) 51:97-101; Cohen et al., *Virology* (1984) 138:178-182. Alternatively, a DNA sequence encoding the particular viral protein can be prepared synthetically rather than cloned. The DNA sequence can be designed with the appropriate codons for the viral protein amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J Biol Chem* (1984) 259:6311.

Once a coding sequence for the viral protein has been prepared or isolated, it can be cloned into any suitable vector or replicon. Numerous cloning vectors are known to those of skill in the art, and the selection of an appropriate cloning vector is a matter of choice. Examples of recombinant DNA vectors for cloning and host cells which they can transform (in parenthesis) include the bacteriophage lambda (*E. coli*), pBR322 (*E.coli*), pACYC177 (*E. coli*), pKT230 (gram-negative bacteria), pGV1 106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), YCp19 (Saccharomyces) and bovine papilloma virus (mammalian cells). See generally, *DNA Cloning: Vols. I & II.* supra; and Sambrook et al., supra.

The coding sequence for the viral protein can be placed under the control of a promoter, ribosome binding site (for bacterial expression) and, optionally, an operator (collectively referred to herein as "control" elements), so that the DNA sequence encoding the viral protein is transcribed into RNA in the host cell transformed by a vector containing this expression construction. The coding sequence may or may not contain a signal peptide or leader sequence. In bacteria, for example, the viral protein is preferably made by the expression of a coding sequence containing a leader sequence which is removed by the bacterial host in post-translational processing. See, e.g., U.S. Pat. Nos. 4,431,739; 4,425,437; 4,338,397.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). The control sequences may be ligated to the coding sequence prior to insertion into a vector, such as the cloning vectors described above. Alternatively, the coding sequence can be cloned directly into an expression vector which already contains the control sequences and an appropriate restriction site.

A number of procaryotic expression vectors are known in the art. See, e.g., U.S. Pat. Nos. 4,440,859; 4,436,815; 4,431,740; 4,431,739; 4,428,941; 4,425,437; 4,418,149; 4,411,994; 4,366,246; 4,342,832; see also UK Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; and 96,491.

Particularly useful for expression of the rotaviral genes of the instant invention are insect cells and vectors suitable for use in these cells. Such systems are known in the art, and include, for example, insect expression transfer vectors constructed from the baculovirus *Autographa californica* nuclear polyhedrosis virus (AcNPV). Such expression vectors typically use the strong viral polyhedrin gene promoter to control expression of heterologous genes. Methods for the introduction of heterologous DNA into the desired site in the baculovirus are known in the art. (See, e.g. Smith, et al., *Mol and Cell Biol* (1983) 3:2156-2165; and Luckow and Sumners *Virology* (1989) 17:31. Insertion can be, for example, into a gene such as the polyhedrin gene, by homologous recombination. Insertion can also be into a restriction enzyme site engineered into the desired baculovirus gene. Sequences encoding signal peptides can also be used in these expression systems since these peptides are recognized by insect cells and will cause the secretion of the expressed product into the expression medium.

Depending on the expression system and host selected, the viral protein is produced by growing host cells transformed by an expression vector described above under conditions whereby the protein is expressed. The protein is then isolated from the host cells and purified. If the expression system secretes the protein into growth media, the protein can be purified directly from cell-free media. If the protein is not secreted, it is isolated from cell lysates. The selection of the appropriate growth conditions and recovery methods are within the skill of the art.

Purified VP6 protein exhibits structural polymorphism. Specifically, hexamers and small hexagonal lattices are present in many of the samples. Tubular particles form between about pH 5.0 and about pH 9.0, and are moderately stable to changes in temperature and ionic strength. The formation of these particles is fully reversible. Spherical particles reassembling single-shelled virus can be formed at about pH 4.0. A novel structure, in the form of sheets, composed of small-hole lattice, is formed in samples shifted from about pH 6.0 to about pH 4.0. These results demonstrate the importance of VP6 and of protein-protein interactions for rotavirus assembly.

Such protein-protein interactions are likely involved in the observed phenomenon that certain peptides can bind to VP6 in its monomeric form or to various oligomeric structures formed from VP6 monomers, such as in vitro assembled tubes and spheres. The attachment is mediated by a specific binding site(s) within VP6.

After the individual outer and inner capsid proteins have been either isolated, synthesized, or recombinantly produced, these proteins are assembled into viral particles using a calcium dependent process described in the examples and in Ready, K. F. M., et al., Virology (1988) 167:269-273. FIG. 7 depicts a representative scheme for the production of in vitro assembled rotavirus particles.

As explained above, the viral particles can be administered in vaccine compositions in combination with purified, unassembled outer capsid proteins, or with cell extracts including one or more of the individual outer capsid proteins. These cell extracts are prepared by techniques well known in the art. For example, cell extracts can be prepared by cultivating rotavirus in African Green Monkey MA104 cells, harvesting the cells and media together and removing the cells by centrifugation. The resulting supernatant includes rotavirus proteins. The proteins can be further purified using density gradient ultracentrifugation. The virus pellet is then subjected to treatment with $CaCl_2$ and $LiCl_2$, as described in Ready, K. F. M. and Sabara, M. *Virology* (1987) 157:189–198, to obtain the individual viral particles. VP4 is present in very small amounts in such preparations. Furthermore, small amounts of VP4 are often present in the VP7 fractions.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR §1.14 and 35 USC §122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
|---|---|---|
| pAC373BRV6 (in *E. coli*) | 31 August 1987 | 40362 |
| BVLVP4 (in *A. californica*) | 24 October 1990 | |
| BYVP7 (in *A. californica*) | 24 October 1990 | |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See, Sambrook et al., supra. Restriction enzymes, $T_4$ DNA ligase, *E. coli,* DNA polymerase I, Klenow fragment, and other biological reagents were purchased from commercial suppliers and used according to the manufacturers' directions. Double-stranded DNA fragments were separated on agarose gels.

Animals

Rotavirus-free mice (CD1) were purchased from Harlan Sprague Dawley Inc., (Indianapolis, Ind.). The age of the mice at the time of purchase was approximately 6 weeks. The mice weighed between 25 and 30 grams. All mice were found to be seronegative for antibodies to rotavirus using an ELISA assay (Ijaz, M. K. et al. *Exp Mol Path* (1989) 51:186–204). The animals were housed in isolation units throughout the experiment.

Cells and Virus

MA104 cells (African green monkey) were cultured in Eagle's minimal essential media (MEM) supplemented with 10% fetal bovine serum (FBS) (Gibco Laboratories, Grand Island, N.Y.). Bovine rotavirus isolate C486 was cultured from the feces of diarrheic calves by a method described previously (Babiuk, L. A. et al., *J Clin Microbiol* (1977) 6:610–617). Rotavirus C486 is publicly available from the ATCC, Rockville, Md. (accession no. VR-917). Simian rotavirus strain SA11 (serotype 3) was obtained from Dr. H. Malherbe (San Antonio, Tex.) and human rotavirus strain DS1 (serotype 2) and human rotavirus strain Wa (serotype 1) were obtained from Dr. H. Greenberg (Stanford University, Calif.).

These viruses were propagated in confluent MA104 cells in the presence of 1 μg of trypsin (Difco Laboratories, Detroit, Mich.) per ml in the absence of FBS. Cells and supernatant were harvested together and cells were removed by centrifugation at 500g for 20 min. Virus was concentrated from the clarified supernatant fluids by pelleting through a 40% sucrose-cushion at 100,000 g for 2½ hr at 15° C. The virus pellet was resuspended in double distilled water and the amount of virus protein was estimated spectrophotometrically as described previously (Ijaz, M. K. et al., *Antiviral Res* (1987) 8:283–298). The resuspended virus was stored at −70° C. Individual inner and outer capsid proteins were isolated from the preparation as described in the examples below.

Plaque Assay

A plaque assay for the quantitation of infectious rotavirus was performed according to the method described previously (Aha, P. M. and Sabara, M. I. *J Virol* (1990) 28:25–32). Briefly, 12 well tissue culture plates (NUNC) containing confluent monolayers of MA104 cells, were washed twice with MEM (without FBS). Serial tenfold dilutions of each rotavirus isolate were prepared in MEM containing trypsin (Difco Laboratories, Detroit, Mich.) to a final concentration of 10 μg/ml. Following adsorption of the virus at 37° C. for 1 hr, the inoculum was aspirated, cells were washed with MEM and overlaid with Dulbecco's Modified Eagle Medium (DMEM), containing 4% Sephadex G-75 beads (Pharmacia). The plates were incubated for 2 days at 37° C., the overlay was aspirated and plates were stained with 0.5% crystal violet/80% methanol/PBS, washed and plaques enumerated.

ELISA Procedure

The ELISA was a modification of a previously described procedure (Sabara, M. et al., *J Virol* (1985) 53:58-66). All incubations were performed at room temperature (20° C.) for 1 hr unless stated otherwise. Polystyrene, 96-well Immunolon 2 plates (Dynatech Labs Inc., Alexandria, Va.) were sensitized for each of the assay systems and used as follows.

For the detection of protein specific antibody, plates were coated overnight with the respective protein (5 picomoles/well) diluted in 0.05M carbonate bicarbonate buffer at pH 9.6. Unabsorbed protein was removed by extensive washing with distilled water. The uncoated sites on the plate were blocked by overnight treatment with 3% horse serum in 0.01M PAS and then washed with double distilled $H_2O$. The plated antigen was overlaid with 75 μl of mouse antiserum/well in 0.01M PAS containing 1% horse serum and 0.05% Tween 20. Incubation was carried out for 2 hr at room temperature after which time the unbound antibody was removed by washing with 0.01M PAS containing 0.05% Tween 20 (PBST). A 1/5000 dilution (in PBST plus 1% horse serum) of biotinylated-goat anti-mouse serum (Zymed Laboratories Inc., San Francisco, Calif.) was then added per well and incubated for one hr at room temperature. After washing in PBST, plates were incubated for one hr with 75 μl of streptavidin horseradish peroxidase conjugate diluted in PBST and 1% horse serum. After washing with PBST, the substrate (2.2'-Azino-di-[3 ethyl-benzthiazoline sulfonate], ABTS, Boehringer-Mannheim) was added. The color development was stopped after 10 min by the addition of 10% SDS. The optical density of the wells was determined at 405 nm by an ELISA reader (BioRad Laboratories, Richmond, Calif.). Titers were expressed as a reciprocal of the highest dilution with an OD of >2 SD over mean background levels.

Sodium Dodecyl Sulphate Polyacrylamide Gel Electrophoresis (SDS-PAGE):

Viral proteins were separated by SDS-PAGE under both reducing and non-reducing conditions according to the procedure described by Laemmli (Laemmli, U.K. *Nature* (1970) 227:680-685). Virus samples were resuspended in electrophoresis sample buffer (0.337M Tris pH 6.8, 6% SDS, 30% glycerol, 0.03% bromophenol blue) for running under nonreducing conditions and included 3.75% mercaptoethanol (BME) for reducing conditions. The samples were boiled for 5 to 10 min and analyzed following electrophoresis on a 10% polyacrylamide resolving gel with a 3% stacking gel.

Western Blotting of Rotavirus Proteins

Protein-specific antibodies were detected by the Western blotting technique described by Towbin et al. (Towbin, H. et al., *Proc Natl Acad Sci USA* (1979) 76:4350-4354). Viral proteins separated on a 10% polyacrylamide gel, were transferred to nitrocellulose paper (0.45 μm) (BioRad Laboratories) by electroblotting at 100 volts for one hr in a buffer containing 20 mM Tris-190 mM glycine-20% methanol. Replica nitrocellulose strips were stained with amido black to determine the efficiency of protein transfer.

After transfer, reaction of viral protein with serum samples was determined as described previously (Braun, D. K. et al., *J Virol* (1983) 46:103-112). Nonspecific reactions were blocked with 3% bovine serum albumin (BSA) in 0.01M TBS. After washing with TBST, the reaction was developed with protein A gold (BioRad Laboratories) for one hr. Following development, the protein bands were intensified by silver enhancement (Janssen Biotech, N.V., Belgium).

EXAMPLE 1

Isolation of Viral Proteins

A. Isolation of Native VP6

The VP6 viral protein was isolated from the purified virus suspension (described above) by successive degradation of purified virus with EDTA and either $CaCl_2$ or LiCl, as follows. Outer capsid proteins were removed by incubating virus (3 mg/ml) in 50 mM EDTA, 0.01M Tris-HCl, pH 7.4 at 4° C. for 30 min. Subviral particles were recovered by ultracentrifugation (100,000×g, 2-3 hr, 4° C.) and resuspended in 0.01M Tris-HCl, pH 7.4 or 0.01M sodium borate, pH 9.0. They were then treated with either 1.5M $CaCl_2$ with 0.01M Tris-HCl, pH 7.4 at 20° C. for 20-30 min, or were frozen in 2M LiCl, 0.01M sodium borate, pH 9.0 at −70° C. for 4 days. Cores and undegraded particles were separated from solubilized protein by ultracentrifugation. EDTA and salts were removed by extensive dialysis at 4° C. against 0.01M Tris-HCl, pH 7.4, unless otherwise indicated. The purity of the samples was examined by polyacrylamide gel electrophoresis (PAGE) as described above.

B. Isolation of Native VP4

The limited number of copies of VP4 protein per virus particle makes the purification of large amounts of this protein difficult. However, VP4 is found in the supernatant obtained after ultracentrifugation following treatment of the subviral particles with 1.5M $CaCl_2$ or 2M LiCl treatment of intact virus particles, as described in the isolation of native VP6. VP4 can also be purified from this pellet by e.g. HPLC, affinity chromatography, ion-exchange chromatography, etc.

C. Isolation of Native VP7

As with VP4, VP7 is also found in the supernatants described above but in larger amounts. See, Ready, K. F. M., et al. *Virology* (1988) 167:269-273. VP7 can be further purified using HPLC, affinity chromatography, ion-exchange chromatography, etc.

EXAMPLE 2

Production of Recombinant Viral Protein

A. Production of Recombinant VP6

The construction of recombinant Autographa californica nuclear polyhedrosis virus (AcNPV) containing gene 6 from bovine rotavirus (BRV) and assembly of VP6 particles following infection of *Spodoptera frugiperda* (SF9) cells has been described previously (Redmond, M. J. et al., *Mol Immunol*, In Press. Briefly, genomic RNA extracted from purified bovine rotavirus strain C486 was used to produce cDNA. The cDNA was ligated into the Pst I site of pBR322 and used to transform *E. coli* strain DH1. The resulting colonies were probed with radiolabeled cDNA prepared from purified genomic RNA segment 6 as template.

Clone pR6-42 which contained a complete copy of the gene 6 RNA, was partially digested with Aha III which removed seven 5' noncoding nucleotides as well as the oligo-dC tails added during cDNA cloning. A Bam HI linker was then added.

The 3' oligo-dC tail and noncoding region were removed by digestion with Acc I which removes 56 noncoding nucleotides from the VP6 gene. A Bam HI linker was then added. The gene 6 cDNA was then ligated into the Bam HI site of the baculovirus transfer vector pAc373. This vector was designated pAC373BRV6 (ATCC no. 40362). Integration of the rotavirus gene into the genome of *A. californica* was then carried out by homologous recombination in *S. frugidperda* (SF9) cells as outlined by Summers, M. D. and Smith, G. E., *Texas Agricultural Station Bulletin* 1555:26-27. Recombinants were identified by plaque hybridization, as described above, using radiolabeled cDNA prepared from purified genomic RNA segment 6. Recombinants were plaque purified and analyzed for expression of recombinant gene 6 produced proteins by SDS-PAGE analysis and Western blotting using the methods described above.

The recombinant virus containing gene 6 was used to infect SF9 cells. Following incubation for 72 hr at 27C, the cells were lysed in a 2 ml $NaHCO^3$ buffer (pH 7.5) containing 0.05% triton X-100 and 0.2 trypsin inhibitor units per ml. Cellular debris was removed by centrifugation at 1500 g. The supernatant was dialyzed against 0.1M glycine buffer (pH 3.0) for 24 hr. This dissociates VP6 aggregates into monomers. The dialysis solution was exchanged for 0.01M citrate buffer (pH 4.0) and dialysis continued for 24 hr, during which time spheres of VP6 formed. This dialysis buffer was exchanged for 0.01M Tris-HCl (pH 7.4)+1 mM sodium azide. Dialysis was then continued overnight at 4° C. Nonaggregated material was removed by ultracentrifugation using 300,000 dalton molecular weight cutoff filters. The quality of the VP6 spheres produced by this method was determined by electromicroscopy and purity confirmed by SDS-PAGE.

B. Production of Recombinant VP4

VP4 was produced recombinantly as described for VP6 except that site directed mutagenesis was used to insert a Bam HI restriction site immediately upstream of the translational initiation codon of the cDNA including gene 4 (the gene encoding VP4), resulting in the deletion of nine nucleotides normally present preceding the VP4 initiation codon. The 3' end of the gene was left unmodified.

The modified gene 4 was ligated into transfer vector pVL941. Integration of gene 4 into the *A. californica* genome was carried out as above to render the expression vector BVLVP4.

Crude detergent lysates of the VP4-baculovirus infected SF9 cells were used as starting material in the production of viral particles as described below. The interaction between VP4 and VP6 is analogous to an affinity purification step. Thus, the VP6-VP4 complex can be separated from unbound VP4 and other cellular proteins by ultracentrifugation over sucrose gradients.

C. Production of Recombinant VP7 cDNA including a full length copy of the gene for VP7 (gene 8) was cloned and identified as described above. A clone (clone pr8-G) which contained the full length cDNA copy of the VP7 gene was digested with Aha III and Sph I which removed 7 and 27 nucleotides, respectively, from the 5' and 3' ends of the gene. Bam HI linkers were then added to both ends of the DNA.

Gene 8 was ligated into the Bam HI site of pACYM1 and integration of gene B into the genome of *A. californica* proceeded as described for VP6 to yield expression vector BYVP7. Recombinants were identified, plaque purified and assayed for expression as described above.

VP7-baculovirus infected SF9 cells secrete VP7 directly into the growth medium. VP7 is essentially affinity purified therefrom by the formation of double shelled (VP6-VP7) particles, in the presence of 50 mM $CaCl_2$. This separates the VP7 from the other components present in the growth medium. The final purification step is ultracentrifugation over sucrose gradients.

EXAMPLE 3

Assembly of Viral Particles

VP7 and VP4 protein concentrations in growth media and infected cell lysates were estimated on SDS-PGE gels stained with Coomassie Blue, and western blots probed with VP7 and VP4 specific antisera. A standard of native BRV was used at a predetermined concentration. The concentrations of proteins used give the following ratios to VP6.

VP6-VP4. 1:10 w/w

VP6-VP7. 1:10 w/w

The starting material for all particle preparations was 10 μg of VP6. To prepare VP6-VP4 particles, 100 μg of VP4 protein in a detergent lysate of SF9 cells (described in Example 2B) dialyzed in 10 mM Tris+50 mM $CaCl_2$ pH 8 overnight at 4° C. was mixed for 2 hr. at 37° with VP6. If used as a vaccine, the preparation was centrifuged at 100,000 g. for 2 hr. through a 40% sucrose gradient.

To prepare VP6-4-7 particles, the Vp6-4 particles prepared above were added to 100 μg of VP7. The VP7 preparation consisted of media from cell culture that had been dialyzed overnight into 0.1M Tris-HCl pH 8.0 containing 50 mM $CaCl_2$.

The VP6-4+7 mixture was then dialyzed for 3-4 days against 0.1M Tris-HCl pH 8.0 containing 50 mM $CaCl_2$ The particles were purified over sucrose as described previously.

To prepare VP6-VP7, 10 μg of VP6 spheres were mixed with 100 μg of VP7 contained in a preparation obtained by dialyzing tissue culture growth medium, from VP7-baculovirus infected SF9 cells, against 0.1m Tris-HCl pH 8.0 containing 50 mM $CaCl_2$. Dialysis was continued for 3-4 days against the same buffer after the addition of VP6. VP6-7 particles, when required, were purified by ultracentrifugation. In order to produce VP6-7-4 particles, cell lysates containing VP4 equivalent to 100 μg of purified virus were mixed for 2 hrs. at 37° C., with VP6-7, then ultracentrifuged through 40% Sucrose for 2 hrs. at 100,000 G. After this time, particles were purified by centrifugation as described above.

EXAMPLE 4

Protective Capacity of the Assembled Viral Proteins

Vaccine compositions used in this example were as follows: For the primary immunizing dose, each immunogen (Table 1) was emulsified with Freund's complete adjuvant. For the second and third immunizations, each immunogen was emulsified with Freund's incomplete adjuvant. Equal volumes of the immunogen and the adjuvant were used.

Thirteen groups of mice were immunized intramuscularly with the preparations outlined in Table 1. Each mouse was immunized three times before and after breeding. The first immunization was given when the mice were seven weeks old and was followed by the second and third vaccinations at two week intervals. Litters were born when the mice were 12 to 14 weeks old.

Following birth, the mouse pups were allowed to suckle their dams and were challenged at 7 days of age with one of four rotavirus isolates. These isolates were bovine rotavirus strain C486 (serotype 6), simian rotavirus strain SA11 (serotype 3), human rotavirus strain DS1 (serotype 1) and Wa (serotype 2). The SA11 isolate was obtained from Dr. H. Malherbe (San Antonio, Tex.) and the strain Wa and DS1 isolates were obtained from Dr. H. Greenberg (Stanford University, Calif.). The strain C486 which was a local isolate adapted to grow in MA104 cells (Babiuk, L. A. et al., *J Clin Microbiol* (1977) 6:610–617). These viruses were grown in MA104 cells, harvested and concentrated for challenge by the method described previously (Ijaz et al., *Antiviral Res* (1987) 8:283–298. The challenge dose for each isolate was approximately $10^4$ PFU/mouse suspended in MEM in 100 µl volume. For challenge, the virus preparations were administered by intubation of the stomach with a soft flexible plastic feeding tube. Trypan blue dye (GIBCO) was used as a marker to assess the accuracy of intubation.

The appearance of diarrhea was scored clinically up to 72 hr post-challenge using clinical scores as follows:

(−) no sign of diarrhea in live mice, or on necropsy;

(+) no external signs of diarrhea but semi-liquid colon contents at autopsy;

(++) fluid was apparent on palpation of the abdomen and the colon was filled with liquid feces and gas;

(+++) the external anal region was soiled with feces and intestinal fluid was present on palpation and;

(++++) liquid feces present around the anal region and on palpation of the abdomen intestinal fluid was present and oozed from the anus, severe dehydration, internal liquid content in colon and caecum and distention due to accumulation of gas.

TABLE 1

HOMOLOGOUS PROTECTION OF NEONATAL MICE SUCKLING ON DAMS IMMUNIZED WITH RECOMBINANT ROTAVIRUS PROTEINS

| Group | Antigen | Serum Titre | Clinical Score | | | | PRN |
| | | | Wa | DS-1 | SA-11 | BRV | |
|---|---|---|---|---|---|---|---|
| 1 | Sentinel | — | ++++ | ++++ | ++++ | ++++ | |
| 2 | Placebo | — | ++++ | ++++ | ++++ | ++++ | <40 |
| 3 | BRV | 1,540,830 | 0 | 0 | 0 | 0 | >1,280 |
| 4 | VP6 | 5,235 | ++ | ++ | ++ | ++ | <40 |
| 5 | VP7 | 6,105 | ND | ND | ND | + | <40 |
| 6 | VP4 | 53,850 | 0 | 0 | + | 0 | 780 |
| 7 | VP6-VP4 | 31,150 | 0 | 0 | + | 0 | 1,000 |
| 8 | VP6-VP7 | 252,520 | 0 | 0 | ++ | 0 | <40 |
| 9 | VP6-VP4 plus VP6-VP7 (mixture) | 64,805 | 0 | 0 | + | 0 | 740 |
| 10 | VP6-VP4-VP7 | 35,235 | ND | ND | ND | 0 | 225 |
| 11 | VP6-VP7-VP4 | 69,685 | 0 | 0 | + | 0 | 230 |
| 12 | VP6 (100) | 53,625 | ND | ND | ND | ++ | <40 |
| 13 | VP6 (10) | 29,960 | ND | ND | ND | ++ | <40 |
| 14 | VP7 (100) | 4,110 | ND | ND | ND | + | <40 |
| 15 | VP7 (10) | 27,610 | ND | ND | ND | ++ | <40 |
| 16 | VP4 (100) | 22,550 | ND | ND | ND | 0 | 600 |
| 17 | VP4 (10) | 35,150 | 0 | 0 | + | 0 | 540 |
| 18 | VP6 + VP4 | 59,080 | ND | ND | ND | 0 | >1280 |
| 19 | VP6 + VP7 | 145,820 | ND | ND | ND | + | <40 |
| 20 | VP6 + VP7 + VP4 | 44,620 | ND | ND | ND | 0 | 460 |
| 21 | VP5-VP7 plus insect cell proteins | 544,447 | ND | ND | ND | + | <40 |

Group 3 is bovine rotavirus antigen and was given at a dose of 50 µg/mouse.
Groups 4–6 are partially purified viral proteins. 10 µg/mouse of these proteins were administered.
Groups 7–11 and 21 are assembled particles. Approximately 10 µg of VP6 and VP7 were administered per mouse and approximately 3.2 µg of VP4 administered per mouse.
Groups 12–17 are partially purified viral proteins and the µg/mouse administered is in parentheses.
Groups 18–20 are mixed, crude lysates. Approximately 10 µg/mouse of the mixed lysate was administered and 90 µg/mouse of the insect cell protein (Group 21).
ND = Not Done
PRN = 50% plaque reduction nutralization titers.

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
      ( A ) LENGTH: 1356 base pairs
      ( B ) TYPE: nucleic acid
      ( C ) STRANDEDNESS: double
      ( D ) TOPOLOGY: linear ( i i ) MOLECULE TYPE: cDNA ( i x ) FEATURE:
  ( A ) NAME/KEY: CDS
  ( B ) LOCATION: 24..1214

( x i ) SEQUENCE DESCRIPTION: SEQ ID NO:1:

```
GGCTTTTAAA CGAAGTCTTC AAC ATG GAT GTC CTG TAC TCC TTG TCA AAA           50
                         Met Asp Val Leu Tyr Ser Leu Ser Lys
                          1               5

ACT CTT AAA GAT GCT AGA GAC AAA ATT GTC GAA GGC ACA TTA TAC TCC          98
Thr Leu Lys Asp Ala Arg Asp Lys Ile Val Glu Gly Thr Leu Tyr Ser
 10              15                  20                  25

AAT GTA AGT GAT CTA ATT CAA CAA TTT AAT CAA ATG ATA ATT ACT ATG         146
Asn Val Ser Asp Leu Ile Gln Gln Phe Asn Gln Met Ile Ile Thr Met
             30                  35                  40

AAT GGA AAT GAG TTC CAA ACT GGA GGA ATT GGT AAT CTA CCG ATT AGA         194
Asn Gly Asn Glu Phe Gln Thr Gly Gly Ile Gly Asn Leu Pro Ile Arg
                 45                  50                  55

AAT TGG AAT TTT GAT TTT GGA TTA CTT GGA ACA ACT CTA CTA AAT TTA         242
Asn Trp Asn Phe Asp Phe Gly Leu Leu Gly Thr Thr Leu Leu Asn Leu
         60                  65                  70

GAT GCT AAC TAC GTC GAA ACG GCC CGC AAT ACA AAT GAT TAT TTT GTA         290
Asp Ala Asn Tyr Val Glu Thr Ala Arg Asn Thr Asn Asp Tyr Phe Val
     75                  80                  85

GAT TTT GTA GAT AAT GTA TGT ATG GAC GAA ATG GTT AGA GAA TCA CAA         338
Asp Phe Val Asp Asn Val Cys Met Asp Glu Met Val Arg Glu Ser Gln
 90                  95                 100                 105

AGA AAT GGA ATT GCA CCA CAA TCA GAT TCA CTT ATA AAG TTA TCA GGC         386
Arg Asn Gly Ile Ala Pro Gln Ser Asp Ser Leu Ile Lys Leu Ser Gly
             110                 115                 120

ATT AAA TTT AAA AGA ATA AAT TTT GAC AAT TCA TCA GAA TAC ATA GAG         434
Ile Lys Phe Lys Arg Ile Asn Phe Asp Asn Ser Ser Glu Tyr Ile Glu
                 125                 130                 135

AAC TGG AAT TTG CCA AAT AGA AGA CAA AGA ACG GGT TTT ACA TTT CAT         482
Asn Trp Asn Leu Pro Asn Arg Arg Gln Arg Thr Gly Phe Thr Phe His
         140                 145                 150

AAA CCA AAC ATT TTC CCT TAT TCA GCT TCA TTC ACG TTG AAC AGA TCA         530
Lys Pro Asn Ile Phe Pro Tyr Ser Ala Ser Phe Thr Leu Asn Arg Ser
 155                 160                 165

CAA CCT TCT CAT GAT AAC TTG ATG GGT ACG ATG TGG CTC AAT GCG GGA         578
Gln Pro Ser His Asp Asn Leu Met Gly Thr Met Trp Leu Asn Ala Gly
170                 175                 180                 185

TCA GAA ATT CAG GTC GCT GGA TTC GAC TAC TCA TGT GCA ATA AAC GCG         626
Ser Glu Ile Gln Val Ala Gly Phe Asp Tyr Ser Cys Ala Ile Asn Ala
             190                 195                 200

CCA GCT AAT ACG CAA CAA TTT GAG CAT ATT GTA CAG CTT CGA AGG GTG         674
Pro Ala Asn Thr Gln Gln Phe Glu His Ile Val Gln Leu Arg Arg Val
                 205                 210                 215

TTG ACT ACA GCT ACA ATA ACT CTT TTA CCA GAT GCA GAA AGA TTT AGT         722
Leu Thr Thr Ala Thr Ile Thr Leu Leu Pro Asp Ala Glu Arg Phe Ser
         220                 225                 230

TTT CCA AGA GTG ATT ACT TCA GCT GAC GGA GCG ACT ACA TGG TAC TTC         770
Phe Pro Arg Val Ile Thr Ser Ala Asp Gly Ala Thr Thr Trp Tyr Phe
 235                 240                 245

AAT CCA GTG ATT CTT AGA CCA AAT AAC GTT GAA ATA GAG TTT CTA CTA         818
Asn Pro Val Ile Leu Arg Pro Asn Asn Val Glu Ile Glu Phe Leu Leu
250                 255                 260                 265

AAC GGG CAG ATA ATA AAT ACT TAC CAA GCA AGA TTT GGA ACC ATC ATA         866
Asn Gly Gln Ile Ile Asn Thr Tyr Gln Ala Arg Phe Gly Thr Ile Ile
             270                 275                 280

GCT AGA AAT TTT GAT ACA ATT AGA TTG TCA TTT CAG TTG ATG AGA CCA         914
Ala Arg Asn Phe Asp Thr Ile Arg Leu Ser Phe Gln Leu Met Arg Pro
```

-continued

```
                          285                           290                             295
CCA AAT ATG ACA CCA GCG GTA GCG GCG TTA TTT CCA AAT GCG CAG CCA        962
Pro Asn Met Thr Pro Ala Val Ala Ala Leu Phe Pro Asn Ala Gln Pro
        300                     305                     310

TTT GAA CAT CAC GCA ACA GTA GGA CTC ACG CTT AGA ATT GAA TCT GCA       1010
Phe Glu His His Ala Thr Val Gly Leu Thr Leu Arg Ile Glu Ser Ala
    315                     320                     325

GTT TGT GAA TCA GTA CTT GCC GAC GCA AGC GAA ACA ATG CTA GCA AAT       1058
Val Cys Glu Ser Val Leu Ala Asp Ala Ser Glu Thr Met Leu Ala Asn
330                     335                     340                 345

GTG ACA TCT GTT AGA CAA GAA TAC GCG ATA CCA GTT GGA CCA GTT TTT       1106
Val Thr Ser Val Arg Gln Glu Tyr Ala Ile Pro Val Gly Pro Val Phe
            350                     355                     360

CCA CCA GGT ATG AAT TGG ACT GAT TTG ATC ACT AAC TAT TCA CCA TCT       1154
Pro Pro Gly Met Asn Trp Thr Asp Leu Ile Thr Asn Tyr Ser Pro Ser
                365                     370                     375

AGA GAG GAT AAC TTG CAG CGT GTA TTT ACA GTG GCT TCC ATT AGA AGC       1202
Arg Glu Asp Asn Leu Gln Arg Val Phe Thr Val Ala Ser Ile Arg Ser
            380                     385                     390

ATG CTT GTC AAA TGAGGACCAA GCTAACCACT TGGTATCCGA CTTTGGTGAG           1254
Met Leu Val Lys
        395

TATGTAGCTA CGTCAAGCTG TTTGAACTCT GTAAGTAAGG ATGCGTCTAC GTATTCGCTA     1314

CACAGAGTAA TCACTCAGAT GGCGTAGTGA GAGGATGTGA CC                        1356
```

( 2 ) INFORMATION FOR SEQ ID NO:2:

( i ) SEQUENCE CHARACTERISTICS:
        ( A ) LENGTH: 397 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Val Leu Tyr Ser Leu Ser Lys Thr Leu Lys Asp Ala Arg Asp
 1               5                  10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
        35                  40                  45

Gly Gly Ile Gly Asn Leu Pro Ile Arg Asn Trp Asn Phe Asp Phe Gly
    50                  55                  60

Leu Leu Gly Thr Thr Leu Leu Asn Leu Asp Ala Asn Tyr Val Glu Thr
65                  70                  75                  80

Ala Arg Asn Thr Asn Asp Tyr Phe Val Asp Phe Val Asp Asn Val Cys
                85                  90                  95

Met Asp Glu Met Val Arg Glu Ser Gln Arg Asn Gly Ile Ala Pro Gln
            100                 105                 110

Ser Asp Ser Leu Ile Lys Leu Ser Gly Ile Lys Phe Lys Arg Ile Asn
        115                 120                 125

Phe Asp Asn Ser Ser Glu Tyr Ile Glu Asn Trp Asn Leu Pro Asn Arg
    130                 135                 140

Arg Gln Arg Thr Gly Phe Thr Phe His Lys Pro Asn Ile Phe Pro Tyr
145                 150                 155                 160

Ser Ala Ser Phe Thr Leu Asn Arg Ser Gln Pro Ser His Asp Asn Leu
                165                 170                 175

Met Gly Thr Met Trp Leu Asn Ala Gly Ser Glu Ile Gln Val Ala Gly
            180                 185                 190
```

```
Phe  Asp  Tyr  Ser  Cys  Ala  Ile  Asn  Ala  Pro  Ala  Asn  Thr  Gln  Gln  Phe
          195                 200                      205

Glu  His  Ile  Val  Gln  Leu  Arg  Arg  Val  Leu  Thr  Thr  Ala  Thr  Ile  Thr
     210                      215                 220

Leu  Leu  Pro  Asp  Ala  Glu  Arg  Phe  Ser  Phe  Pro  Arg  Val  Ile  Thr  Ser
225                      230                 235                           240

Ala  Asp  Gly  Ala  Thr  Thr  Trp  Tyr  Phe  Asn  Pro  Val  Ile  Leu  Arg  Pro
               245                      250                      255

Asn  Asn  Val  Glu  Ile  Glu  Phe  Leu  Leu  Asn  Gly  Gln  Ile  Ile  Asn  Thr
               260                 265                           270

Tyr  Gln  Ala  Arg  Phe  Gly  Thr  Ile  Ile  Ala  Arg  Asn  Phe  Asp  Thr  Ile
          275                      280                      285

Arg  Leu  Ser  Phe  Gln  Leu  Met  Arg  Pro  Pro  Asn  Met  Thr  Pro  Ala  Val
     290                      295                 300

Ala  Ala  Leu  Phe  Pro  Asn  Ala  Gln  Pro  Phe  Glu  His  His  Ala  Thr  Val
305                      310                 315                           320

Gly  Leu  Thr  Leu  Arg  Ile  Glu  Ser  Ala  Val  Cys  Glu  Ser  Val  Leu  Ala
               325                      330                      335

Asp  Ala  Ser  Glu  Thr  Met  Leu  Ala  Asn  Val  Thr  Ser  Val  Arg  Gln  Glu
               340                      345                      350

Tyr  Ala  Ile  Pro  Val  Gly  Pro  Val  Phe  Pro  Pro  Gly  Met  Asn  Trp  Thr
          355                      360                      365

Asp  Leu  Ile  Thr  Asn  Tyr  Ser  Pro  Ser  Arg  Glu  Asp  Asn  Leu  Gln  Arg
     370                      375                 380

Val  Phe  Thr  Val  Ala  Ser  Ile  Arg  Ser  Met  Leu  Val  Lys
385                      390                 395
```

( 2 ) INFORMATION FOR SEQ ID NO:3:

( i ) SEQUENCE CHARACTERISTICS:
        ( A ) LENGTH: 397 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

```
Met  Asp  Val  Leu  Tyr  Ser  Leu  Ser  Lys  Thr  Leu  Lys  Asp  Ala  Arg  Asp
1                   5                   10                      15

Lys  Ile  Val  Glu  Gly  Thr  Leu  Tyr  Ser  Asn  Val  Ser  Asp  Leu  Ile  Gln
               20                  25                      30

Gln  Phe  Asn  Gln  Met  Ile  Ile  Thr  Met  Asn  Gly  Asn  Glu  Phe  Gln  Thr
          35                      40                      45

Gly  Gly  Ile  Gly  Asn  Leu  Pro  Ile  Arg  Asn  Trp  Asn  Phe  Asp  Phe  Gly
     50                  55                      60

Leu  Leu  Gly  Thr  Thr  Leu  Leu  Asn  Leu  Asp  Ala  Asn  Tyr  Val  Glu  Thr
65                       70                      75                       80

Ala  Arg  Asn  Thr  Asn  Asp  Tyr  Phe  Val  Asp  Phe  Val  Asp  Asn  Val  Cys
               85                      90                      95

Met  Asp  Glu  Met  Val  Arg  Glu  Ser  Gln  Arg  Asn  Gly  Ile  Ala  Pro  Gln
               100                     105                     110

Ser  Asp  Ser  Leu  Ile  Lys  Leu  Ser  Gly  Ile  Lys  Phe  Lys  Arg  Ile  Asn
          115                     120                     125

Phe  Asp  Asn  Ser  Ser  Glu  Tyr  Ile  Glu  Asn  Trp  Asn  Leu  Pro  Asn  Arg
     130                     135                     140

Arg  Gln  Arg  Thr  Gly  Phe  Thr  Phe  His  Lys  Pro  Asn  Ile  Phe  Pro  Tyr
145                     150                     155                      160
```

```
Ser Ala Ser Phe Thr Leu Asn Arg Ser Gln Pro Ser His Asp Asn Leu
            165                 170                 175

Met Gly Thr Met Trp Leu Asn Ala Gly Ser Glu Ile Gln Val Ala Gly
            180                 185                 190

Phe Asp Tyr Ser Cys Ala Ile Asn Ala Pro Ala Asn Thr Gln Gln Phe
            195                 200                 205

Glu His Ile Val Gln Leu Arg Arg Val Leu Thr Thr Ala Thr Ile Thr
            210                 215                 220

Leu Leu Pro Asp Ala Glu Arg Phe Ser Phe Pro Arg Val Ile Thr Ser
225                 230                 235                 240

Ala Asp Gly Ala Thr Thr Trp Tyr Phe Asn Pro Val Ile Leu Arg Pro
            245                 250                 255

Asn Asn Val Glu Ile Glu Phe Leu Leu Asn Gly Gln Ile Ile Asn Thr
            260                 265                 270

Tyr Gln Ala Arg Phe Gly Thr Ile Ile Ala Arg Asn Phe Asp Thr Ile
            275                 280                 285

Arg Leu Ser Phe Gln Leu Met Arg Pro Pro Asn Met Thr Pro Ala Val
            290                 295                 300

Ala Ala Leu Phe Pro Asn Ala Gln Pro Phe Glu His His Ala Thr Val
305                 310                 315                 320

Gly Leu Thr Leu Arg Ile Glu Ser Ala Val Cys Glu Ser Val Leu Ala
            325                 330                 335

Asp Ala Ser Glu Thr Met Leu Ala Asn Val Thr Ser Val Arg Gln Glu
            340                 345                 350

Tyr Ala Ile Pro Val Gly Pro Val Phe Pro Pro Gly Met Asn Trp Thr
            355                 360                 365

Asp Leu Ile Thr Asn Tyr Ser Pro Ser Arg Glu Asp Asn Leu Gln Arg
            370                 375                 380

Val Phe Thr Val Ala Ser Ile Arg Ser Met Leu Val Lys
385                 390                 395
```

( 2 ) INFORMATION FOR SEQ ID NO:4:

( i ) SEQUENCE CHARACTERISTICS:
        ( A ) LENGTH: 397 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:4:

```
Met Asp Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
            20                  25                  30

Gln Phe Asn Gln Met Ile Ile Thr Met Asn Gly Asn Glu Phe Gln Thr
            35                  40                  45

Gly Gly Ile Gly Asn Leu Pro Ile Arg Asn Trp Asn Phe Asp Phe Gly
            50                  55                  60

Leu Leu Gly Thr Thr Leu Leu Asn Leu Asp Ala Asn Tyr Val Glu Thr
65                  70                  75                  80

Ala Arg Asn Thr Ile Asp Tyr Phe Val Asp Phe Val Asp Asn Val Cys
            85                  90                  95

Met Asp Glu Met Val Arg Glu Ser Gln Arg Asn Gly Ile Ala Pro Gln
            100                 105                 110

Ser Asp Ser Leu Ile Lys Leu Ser Gly Ile Lys Phe Lys Arg Ile Asn
            115                 120                 125
```

```
Phe  Asp  Asn  Ser  Ser  Glu  Tyr  Ile  Glu  Asn  Trp  Asn  Leu  Pro  Asn  Arg
     130                 135                      140

Arg  Gln  Arg  Thr  Gly  Phe  Thr  Phe  His  Lys  Pro  Asn  Ile  Phe  Pro  Tyr
145                      150                      155                           160

Ser  Ala  Ser  Phe  Thr  Leu  Asn  Arg  Ser  Gln  Pro  Ala  His  Asp  Asn  Leu
                    165                      170                          175

Met  Gly  Thr  Met  Trp  Leu  Asn  Ala  Gly  Ser  Glu  Ile  Gln  Val  Ala  Gly
               180                      185                          190

Phe  Asp  Tyr  Ser  Cys  Ala  Ile  Asn  Ala  Pro  Ala  Asn  Thr  Gln  Gln  Phe
               195                 200                      205

Glu  His  Ile  Val  Gln  Leu  Arg  Arg  Val  Leu  Thr  Thr  Ala  Thr  Ile  Thr
     210                      215                      220

Leu  Leu  Pro  Asp  Ala  Glu  Arg  Phe  Ser  Phe  Pro  Arg  Val  Ile  Thr  Ser
225                      230                      235                           240

Ala  Asp  Gly  Ala  Thr  Thr  Trp  Tyr  Phe  Asn  Pro  Val  Ile  Leu  Arg  Pro
                    245                      250                          255

Asn  Asn  Val  Glu  Ile  Glu  Phe  Leu  Leu  Asn  Gly  Gln  Ile  Ile  Asn  Thr
               260                      265                          270

Tyr  Gln  Ala  Arg  Phe  Gly  Thr  Ile  Ile  Ala  Arg  Asn  Phe  Asp  Thr  Ile
          275                      280                      285

Arg  Leu  Ser  Phe  Gln  Leu  Met  Arg  Pro  Pro  Asn  Met  Thr  Pro  Ala  Val
     290                      295                      300

Ala  Ala  Leu  Phe  Pro  Asn  Ala  Gln  Pro  Phe  Glu  His  His  Ala  Thr  Val
305                      310                      315                           320

Gly  Leu  Thr  Leu  Arg  Ile  Glu  Ser  Ala  Val  Cys  Glu  Ser  Val  Leu  Ala
                    325                      330                          335

Asp  Ala  Ser  Glu  Thr  Met  Leu  Ala  Asn  Val  Thr  Ser  Val  Arg  Gln  Glu
               340                      345                          350

Tyr  Ala  Ile  Pro  Val  Gly  Pro  Val  Phe  Pro  Pro  Gly  Met  Asn  Trp  Thr
          355                      360                      365

Asp  Leu  Ile  Thr  Asn  Tyr  Ser  Pro  Ser  Arg  Glu  Asp  Asn  Leu  Gln  Arg
     370                      375                      380

Val  Phe  Thr  Val  Ala  Ser  Ile  Arg  Ser  Met  Leu  Val  Lys
385                      390                      395
```

( 2 ) INFORMATION FOR SEQ ID NO:5:

( i ) SEQUENCE CHARACTERISTICS:
( A ) LENGTH: 397 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:5:

```
Met  Asp  Val  Leu  Tyr  Ser  Leu  Ser  Lys  Thr  Leu  Lys  Asp  Ala  Arg  Asp
1                   5                   10                           15

Lys  Ile  Val  Glu  Gly  Thr  Leu  Tyr  Ser  Asn  Val  Ser  Asp  Leu  Ile  Gln
               20                      25                           30

Gln  Phe  Asn  Gln  Met  Ile  Ile  Thr  Met  Asn  Gly  Asn  Glu  Phe  Gln  Thr
          35                      40                           45

Gly  Gly  Ile  Gly  Asn  Leu  Pro  Ile  Arg  Asn  Trp  Asn  Phe  Asp  Phe  Gly
     50                      55                      60

Leu  Leu  Gly  Thr  Thr  Leu  Leu  Asn  Leu  Asp  Ala  Asn  Tyr  Val  Glu  Thr
65                       70                      75                           80

Ala  Arg  Asn  Thr  Ile  Asp  Tyr  Phe  Val  Asp  Phe  Val  Asp  Asn  Val  Cys
                    85                      90                           95
```

```
Met  Asp  Glu  Met  Val  Arg  Glu  Ser  Gln  Arg  Asn  Gly  Ile  Ala  Pro  Gln
               100                 105                      110

Ser  Asp  Ser  Leu  Arg  Lys  Leu  Ser  Gly  Ile  Lys  Phe  Lys  Arg  Ile  Asn
          115                      120                      125

Phe  Asp  Asn  Ser  Ser  Glu  Tyr  Ile  Glu  Asn  Trp  Asn  Leu  Gln  Asn  Arg
     130                      135                 140

Arg  Gln  Arg  Thr  Gly  Phe  Thr  Phe  His  Lys  Pro  Asn  Ile  Phe  Pro  Tyr
145                           150                 155                      160

Ser  Ala  Ser  Phe  Thr  Leu  Asn  Arg  Ser  Gln  Pro  Ala  His  Asp  Asn  Leu
                    165                      170                      175

Met  Gly  Thr  Met  Trp  Leu  Asn  Ala  Gly  Ser  Glu  Ile  Gln  Val  Ala  Gly
               180                      185                      190

Phe  Asp  Tyr  Ser  Cys  Ala  Ile  Asn  Ala  Pro  Ala  Asn  Thr  Gln  Gln  Phe
          195                      200                      205

Glu  His  Ile  Val  Gln  Leu  Arg  Arg  Val  Leu  Thr  Thr  Ala  Thr  Ile  Thr
     210                      215                      220

Leu  Leu  Pro  Asp  Ala  Glu  Arg  Phe  Ser  Phe  Pro  Arg  Val  Ile  Asn  Ser
225                           230                 235                      240

Ala  Asp  Gly  Ala  Thr  Thr  Trp  Tyr  Phe  Asn  Pro  Val  Ile  Leu  Arg  Pro
                    245                      250                      255

Asn  Asn  Val  Glu  Val  Glu  Phe  Leu  Leu  Asn  Gly  Gln  Ile  Ile  Asn  Thr
               260                      265                      270

Tyr  Gln  Ala  Arg  Phe  Gly  Thr  Ile  Ile  Ala  Arg  Asn  Phe  Asp  Thr  Ile
          275                      280                      285

Arg  Leu  Ser  Phe  Gln  Leu  Met  Arg  Pro  Pro  Asn  Met  Thr  Pro  Thr  Val
     290                      295                      300

Ala  Ala  Leu  Phe  Pro  Asn  Ala  Gln  Pro  Phe  Glu  His  His  Ala  Thr  Val
305                           310                 315                      320

Gly  Leu  Thr  Leu  Arg  Ile  Glu  Ser  Ala  Val  Cys  Glu  Ser  Val  Leu  Ala
                    325                      330                      335

Asp  Ala  Ser  Glu  Thr  Met  Leu  Ala  Asn  Val  Thr  Ser  Val  Arg  Gln  Glu
               340                      345                      350

Tyr  Ala  Ile  Pro  Val  Gly  Pro  Val  Phe  Pro  Pro  Gly  Met  Asn  Trp  Thr
          355                      360                      365

Asp  Leu  Ile  Thr  Asn  Tyr  Ser  Pro  Ser  Arg  Glu  Asp  Asn  Leu  Gln  Arg
     370                      375                      380

Val  Phe  Thr  Val  Ala  Ser  Ile  Arg  Ser  Met  Leu  Ile  Lys
385                      390                      395
```

( 2 ) INFORMATION FOR SEQ ID NO:6:

( i ) SEQUENCE CHARACTERISTICS:
        ( A ) LENGTH: 397 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

```
Met  Asp  Val  Leu  Tyr  Ser  Leu  Ser  Lys  Thr  Leu  Lys  Asp  Ala  Arg  Asp
1                   5                   10                      15

Lys  Ile  Val  Glu  Gly  Thr  Leu  Tyr  Ser  Asn  Val  Ser  Asp  Leu  Ile  Gln
               20                      25                      30

Gln  Phe  Asn  Gln  Met  Ile  Ile  Thr  Met  Asn  Gly  Asn  Glu  Phe  Gln  Thr
          35                      40                      45

Gly  Gly  Ile  Gly  Asn  Leu  Pro  Thr  Arg  Asn  Trp  Ser  Phe  Asp  Phe  Gly
     50                      55                      60
```

| | | | | | | | | | | | | | | | |
|---|---|---|---|---|---|---|---|---|---|---|---|---|---|---|---|
| Leu | Leu | Gly | Thr | Thr | Leu | Leu | Asn | Leu | Asp | Ala | Asn | Tyr | Val | Glu | Thr |
| 65 | | | | 70 | | | | | 75 | | | | | | 80 |
| Ala | Arg | Asn | Thr | Ile | Asp | Tyr | Phe | Val | Asp | Phe | Val | Asp | Asn | Val | Cys |
| | | | | 85 | | | | 90 | | | | | | 95 | |
| Met | Asp | Glu | Met | Val | Arg | Glu | Ser | Gln | Arg | Asn | Gly | Ile | Ala | Pro | Gln |
| | | | 100 | | | | | 105 | | | | | 110 | | |
| Ser | Glu | Ser | Leu | Arg | Lys | Leu | Ser | Gly | Ile | Lys | Phe | Lys | Arg | Ile | Asn |
| | | 115 | | | | | 120 | | | | | 125 | | | |
| Phe | Asp | Asn | Ser | Ser | Glu | Tyr | Ile | Glu | Asn | Trp | Asn | Leu | Gln | Asn | Arg |
| | 130 | | | | | 135 | | | | | 140 | | | | |
| Arg | Gln | Arg | Thr | Gly | Phe | Thr | Phe | His | Lys | Pro | Asn | Ile | Phe | Pro | Tyr |
| 145 | | | | | 150 | | | | | 155 | | | | | 160 |
| Ser | Ala | Ser | Phe | Thr | Leu | Asn | Arg | Ser | Gln | Pro | Ala | His | Asp | Asn | Leu |
| | | | | 165 | | | | | 170 | | | | | 175 | |
| Met | Gly | Thr | Met | Trp | Leu | Asn | Ala | Gly | Ser | Glu | Ile | His | Val | Ala | Gly |
| | | | 180 | | | | | 185 | | | | | 190 | | |
| Phe | Asp | Tyr | Ser | Cys | Ala | Ile | Asn | Ala | Pro | Ala | Asn | Ile | Gln | Gln | Phe |
| | | | 195 | | | | 200 | | | | | 205 | | | |
| Glu | His | Ile | Val | Gln | Leu | Arg | Arg | Val | Leu | Thr | Thr | Ala | Thr | Ile | Thr |
| | 210 | | | | | 215 | | | | | 220 | | | | |
| Leu | Leu | Pro | Asp | Ala | Glu | Arg | Phe | Ser | Phe | Pro | Arg | Val | Ile | Asn | Ser |
| 225 | | | | | 230 | | | | | 235 | | | | | 240 |
| Ala | Asp | Gly | Ala | Thr | Thr | Trp | Tyr | Phe | Asn | Pro | Val | Ile | Leu | Arg | Pro |
| | | | | 245 | | | | | 250 | | | | | 255 | |
| Asn | Asn | Val | Glu | Val | Glu | Phe | Leu | Leu | Asn | Gly | Gln | Ile | Ile | Asn | Thr |
| | | | 260 | | | | | 265 | | | | | 270 | | |
| Tyr | Gln | Ala | Arg | Phe | Gly | Thr | Ile | Val | Ala | Arg | Asn | Phe | Asp | Thr | Ile |
| | | 275 | | | | | 280 | | | | | 285 | | | |
| Arg | Leu | Ser | Phe | Gln | Leu | Met | Arg | Pro | Pro | Asn | Met | Thr | Pro | Ser | Val |
| 290 | | | | | 295 | | | | | 300 | | | | | |
| Ala | Ala | Leu | Phe | Pro | Asn | Ala | Gln | Pro | Phe | Glu | His | His | Ala | Thr | Val |
| 305 | | | | | 310 | | | | | 315 | | | | | 320 |
| Gly | Leu | Thr | Leu | Arg | Ile | Glu | Ser | Ala | Ile | Cys | Glu | Ser | Val | Leu | Ala |
| | | | | 325 | | | | | 330 | | | | | 335 | |
| Asp | Ala | Ser | Glu | Thr | Met | Leu | Ala | Asn | Val | Thr | Ser | Val | Arg | Gln | Glu |
| | | | 340 | | | | | 345 | | | | | 350 | | |
| Tyr | Ala | Ile | Pro | Val | Gly | Pro | Val | Phe | Pro | Pro | Gly | Met | Asn | Trp | Thr |
| | | 355 | | | | | 360 | | | | | 365 | | | |
| Asp | Leu | Ile | Thr | Asn | Tyr | Ser | Pro | Ser | Arg | Glu | Asp | Asn | Leu | His | Arg |
| | 370 | | | | | 375 | | | | | 380 | | | | |
| Val | Phe | Thr | Val | Ala | Ser | Ile | Arg | Ser | Met | Leu | Val | Lys | | | |
| 385 | | | | | 390 | | | | | 395 | | | | | |

( 2 ) INFORMATION FOR SEQ ID NO:7:

( i ) SEQUENCE CHARACTERISTICS:
        ( A ) LENGTH: 399 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
| Met | Asp | Val | Leu | Tyr | Ser | Leu | Ser | Lys | Thr | Leu | Lys | Asp | Ala | Arg | Asp |
| 1 | | | | 5 | | | | | 10 | | | | | 15 | |
| Lys | Ile | Val | Glu | Gly | Thr | Leu | Tyr | Ser | Asn | Val | Ser | Asp | Leu | Ile | Gln |
| | | | 20 | | | | | 25 | | | | | 30 | | |

|  |  |  |  |  |  |  |  |  |  |  |  |  |  |  |
|---|---|---|---|---|---|---|---|---|---|---|---|---|---|---|
| Gln | Phe | Asn 35 | Gln | Met | Val | Ile | Thr 40 | Met | Asn | Gly | Asn 45 | Glu | Phe | Gln | Thr |
| Gly | Gly 50 | Ile | Gly | Asn | Leu | Pro 55 | Ile | Arg | Asn | Trp | Asn 60 | Phe | Asp | Phe | Gly |
| Leu 65 | Leu | Gly | Thr | Thr | Leu 70 | Leu | Asn | Leu | Asp | Ala 75 | Asn | Tyr | Val | Glu | Thr 80 |
| Ala | Arg | Asn | Thr | Ile 85 | Asp | Tyr | Phe | Val | Phe 90 | Val | Asp | Asn | Val 95 | Cys |
| Met | Asp | Glu | Met 100 | Val | Arg | Glu | Ser | Gln 105 | Arg | Asn | Gly | Ile | Ala 110 | Pro | Gln |
| Ser | Asp | Ser 115 | Leu | Arg | Lys | Leu | Ser 120 | Gly | Ile | Lys | Phe | Lys 125 | Arg | Ile | Asn |
| Phe | Asp 130 | Asn | Ser | Ser | Glu | Tyr 135 | Ile | Glu | Asn | Trp | Asn 140 | Leu | Gln | Asn | Arg |
| Arg 145 | Gln | Arg | Lys | Gly | Phe 150 | Thr | Phe | His | Lys | Pro 155 | Asn | Ile | Phe | Pro | Tyr 160 |
| Ser | Ala | Ser | Phe | Thr 165 | Leu | Asn | Arg | Ser | Gln 170 | Pro | Ala | His | Asp | Asn 175 | Leu |
| Met | Gly | Thr | Met 180 | Trp | Leu | Asn | Ala | Gly 185 | Ser | Glu | Ile | Gln | Val 190 | Ala | Gly |
| Phe | Asp | Tyr 195 | Ser | Cys | Ala | Ile | Asn 200 | Ala | Pro | Ala | Asn | Thr 205 | Gln | Gln | Phe |
| Glu | His 210 | Ile | Val | Gln | Leu | Arg 215 | Arg | Val | Leu | Thr | Thr 220 | Ala | Thr | Ile | Thr |
| Leu 225 | Leu | Pro | Asp | Ala | Glu 230 | Arg | Phe | Ser | Phe | Pro 235 | Arg | Val | Ile | Asn | Ser 240 |
| Ala | Asp | Gly | Thr | Thr 245 | Thr | Trp | Tyr | Phe | Asn 250 | Pro | Val | Ile | Phe | Arg 255 | Pro |
| Asn | Asn | Val | Glu 260 | Ile | Glu | Phe | Leu | Leu 265 | Asn | Gly | Gln | Ile | Ile 270 | Asn | Asn |
| Tyr | Gln | Ala 275 | Arg | Phe | Gly | Thr | Ile 280 | Ile | Ala | Arg | Asn | Phe 285 | Asp | Thr | Ile |
| Arg | Leu 290 | Ser | Phe | Gln | Leu | Met 295 | Arg | Pro | Pro | Gln | Asn 300 | Met | Thr | Pro |
| Ala 305 | Val | Ala | Ala | Leu | Phe 310 | Pro | Asn | Ala | Pro | Pro 315 | Phe | Glu | His | His | Ala 320 |
| Thr | Val | Gly | Leu | Thr 325 | Leu | Arg | Ile | Glu | Ser 330 | Ala | Ile | Cys | Glu | Ser 335 | Val |
| Leu | Ala | Asp | Ala 340 | Ser | Glu | Thr | Met | Leu 345 | Ala | Asn | Val | Thr | Ser 350 | Val | Arg |
| Gln | Glu | Tyr 355 | Ala | Val | Pro | Val | Gly 360 | Pro | Val | Phe | Pro | Pro 365 | Gly | Met | Asn |
| Trp | Thr 370 | Asp | Leu | Ile | Thr | Asn 375 | Tyr | Ser | Pro | Ser | Arg 380 | Glu | Asp | Asn | Leu |
| Gln 385 | Arg | Val | Phe | Thr | Val 390 | Ala | Ser | Ile | Arg | Ser 395 | Met | Leu | Ile | Lys |

( 2 ) INFORMATION FOR SEQ ID NO:8:

( i ) SEQUENCE CHARACTERISTICS:
        ( A ) LENGTH: 397 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

-continued

| | | | | | | | | | | | | | | |
|---|---|---|---|---|---|---|---|---|---|---|---|---|---|---|
| Met 1 | Glu | Val | Leu | Tyr 5 | Ser | Ile | Ser | Lys | Thr 10 | Leu | Lys | Asp | Ala | Arg 15 | Asp |
| Lys | Ile | Val | Glu 20 | Gly | Thr | Leu | Tyr | Ser 25 | Asn | Val | Ser | Asp 30 | Ile | Ile | Gln |
| Gln | Phe | Asn 35 | Gln | Ile | Ile | Val | Thr 40 | Met | Asn | Gly | Asn | Glu 45 | Phe | Gln | Thr |
| Gly | Gly 50 | Ile | Gly | Thr | Leu | Pro 55 | Ile | Arg | Asn | Trp | Thr 60 | Phe | Asp | Phe | Gly |
| Leu 65 | Leu | Gly | Thr | Thr | Leu 70 | Leu | Asn | Leu | Asp | Ala 75 | Asn | Tyr | Val | Glu | Thr 80 |
| Ala | Arg | Thr | Thr | Ile 85 | Glu | Tyr | Phe | Ile | Asp 90 | Phe | Ile | Asp | Asn | Val 95 | Cys |
| Met | Asp | Glu | Met 100 | Thr | Arg | Glu | Ser | Gln 105 | Arg | Asn | Gly | Ile | Ala 110 | Pro | Gln |
| Ser | Asp | Ala 115 | Leu | Arg | Lys | Leu | Ser 120 | Gly | Ile | Lys | Phe | Lys 125 | Arg | Ile | Asn |
| Phe | Asp 130 | Asn | Ser | Ser | Glu | Tyr 135 | Ile | Glu | Asn | Trp | Asn 140 | Leu | Gln | Asn | Arg |
| Arg 145 | Gln | Arg | Thr | Gly | Phe 150 | Val | Phe | His | Lys | Pro 155 | Asn | Ile | Phe | Pro | Tyr 160 |
| Ser | Ala | Ser | Phe | Thr 165 | Leu | Asn | Arg | Ser | Gln 170 | Pro | Leu | His | Asn | Asp 175 | Leu |
| Met | Gly | Thr | Met 180 | Trp | Leu | Asn | Ala | Gly 185 | Ser | Glu | Ile | Gln | Val 190 | Ala | Gly |
| Phe | Asp | Tyr 195 | Ser | Cys | Ala | Ile | Asn 200 | Ala | Pro | Ala | Asn | Thr 205 | Gln | Gln | Phe |
| Glu | His 210 | Ile | Val | Gln | Leu | Arg 215 | Arg | Ala | Leu | Thr | Thr 220 | Ala | Thr | Ile | Thr |
| Ile 225 | Leu | Pro | Asp | Ala | Glu 230 | Arg | Phe | Ser | Phe | Pro 235 | Arg | Val | Ile | Asn | Ser 240 |
| Ala | Asp | Gly | Ala | Thr 245 | Thr | Trp | Phe | Phe | Asn 250 | Pro | Val | Ile | Leu | Arg 255 | Pro |
| Asn | Asn | Val | Glu 260 | Val | Glu | Phe | Leu | Leu 265 | Asn | Gly | Gln | Ile | Ile 270 | Asn | Thr |
| Tyr | Gln | Ala 275 | Arg | Phe | Gly | Thr | Ile 280 | Ile | Ala | Arg | Asn | Phe 285 | Asp | Thr | Ile |
| Arg | Leu 290 | Ser | Phe | Gln | Leu | Met 295 | Arg | Pro | Pro | Asn | Met 300 | Thr | Pro | Ala | Val |
| Asn 305 | Ala | Leu | Phe | Pro | Gln 310 | Ala | Gln | Pro | Phe | Gln 315 | His | His | Ala | Thr | Val 320 |
| Gly | Leu | Thr | Leu | Arg 325 | Ile | Asp | Ser | Ala | Val 330 | Cys | Glu | Ser | Val | Leu 335 | Ala |
| Asp | Ser | Asn | Glu 340 | Thr | Met | Leu | Ala | Asn 345 | Val | Thr | Ala | Val | Arg 350 | Gln | Glu |
| Tyr | Ala | Val 355 | Pro | Val | Gly | Pro | Val 360 | Phe | Pro | Pro | Gly | Met 365 | Asn | Trp | Thr |
| Glu | Leu 370 | Ile | Thr | Asn | Tyr | Ser 375 | Pro | Ser | Arg | Glu | Asp 380 | Asn | Leu | Gln | Arg |
| Val 385 | Phe | Thr | Val | Ala | Ser 390 | Ile | Arg | Ser | Met | Leu 395 | Ile | Lys | | | |

( 2 ) INFORMATION FOR SEQ ID NO:9:

( i ) SEQUENCE CHARACTERISTICS:
        ( A ) LENGTH: 397 amino acids
        ( B ) TYPE: amino acid
        ( C ) STRANDEDNESS: unknown ( D ) TOPOLOGY: unknown ( i i ) MOLECULE TYPE: protein ( x i ) SEQUENCE DESCRIPTION: SEQ ID NO:9:

```
Met Glu Val Leu Tyr Ser Leu Ser Lys Thr Leu Lys Asp Ala Arg Asp
1               5                   10                  15

Lys Ile Val Glu Gly Thr Leu Tyr Ser Asn Val Ser Asp Leu Ile Gln
                20                  25                  30

Gln Phe Asn Gln Met Ile Val Thr Met Asn Gly Asn Asp Phe Gln Thr
            35                  40                  45

Gly Gly Ile Gly Asn Leu Pro Val Arg Asn Trp Thr Phe Asp Phe Gly
        50              55                  60

Leu Leu Gly Thr Thr Leu Leu Asn Leu Asp Ala Asn Tyr Val Glu Thr
65                  70                  75                  80

Ala Arg Thr Thr Ile Glu Tyr Phe Ile Asp Phe Ile Asp Asn Val Cys
                85                  90                  95

Met Asp Glu Met Ala Arg Glu Ser Gln Arg Asn Gly Ile Ala Pro Gln
                100                 105                 110

Ser Glu Ala Phe Arg Lys Leu Ala Gly Ile Lys Phe Lys Arg Ile Asn
            115                 120                 125

Phe Asp Asn Ser Ser Glu Tyr Ile Glu Asn Trp Asn Leu Gln Asn Arg
    130                 135                 140

Arg Gln Arg Thr Gly Phe Ile Phe His Lys Pro Asn Ile Phe Pro Tyr
145                 150                 155                 160

Ser Ala Ser Phe Thr Leu Asn Arg Ser Gln Pro Met His Asp Asn Leu
                165                 170                 175

Met Gly Thr Met Trp Leu Asn Ala Gly Ser Glu Ile Gln Val Ala Gly
                180                 185                 190

Phe Asp Tyr Ser Cys Ala Ile Asn Ala Pro Ala Asn Ile Gln Gln Phe
        195                 200                 205

Glu His Ile Val Gln Leu Arg Arg Ala Leu Thr Thr Ala Thr Ile Thr
    210                 215                 220

Leu Leu Pro Asp Ala Glu Arg Phe Ser Phe Pro Arg Val Ile Asn Ser
225                 230                 235                 240

Ala Asp Gly Ala Thr Thr Trp Phe Phe Asn Pro Val Ile Leu Arg Pro
                245                 250                 255

Asn Asn Val Glu Val Glu Phe Leu Leu Asn Gly Gln Ile Ile Asn Thr
                260                 265                 270

Tyr Gln Ala Arg Phe Gly Thr Ile Val Ala Arg Asn Phe Asp Thr Ile
            275                 280                 285

Arg Leu Ser Phe Gln Leu Met Arg Pro Pro Asn Met Thr Pro Ala Val
    290                 295                 300

Asp Ala Leu Phe Pro Gln Ala Gln Pro Phe Gln His His Ala Thr Val
305                 310                 315                 320

Gly Leu Thr Leu Arg Ile Glu Ser Ala Val Cys Glu Ser Val Leu Ala
                325                 330                 335

Asp Ala Asn Glu Thr Leu Leu Ala Asn Val Thr Ala Val Arg Gln Glu
            340                 345                 350

Tyr Ala Ile Pro Val Gly Pro Val Phe Pro Pro Gly Met Asn Trp Thr
        355                 360                 365

Glu Leu Ile Thr Asn Tyr Ser Pro Ser Arg Glu Asp Asn Leu Gln Arg
    370                 375                 380

Val Phe Thr Val Ala Ser Ile Arg Ser Met Leu Ile Lys
385                 390                 395
```

(2) INFORMATION FOR SEQ ID NO:10:

(i) SEQUENCE CHARACTERISTICS:
       (A) LENGTH: 397 amino acids
       (B) TYPE: amino acid
       (C) STRANDEDNESS: unknown
       (D) TOPOLOGY: unknown (ii) MOLECULE TYPE: protein (xi) SEQUENCE DESCRIPTION: SEQ ID NO:10:

```
Met Glu Val Leu Tyr Ser Leu Ser Lys Thr Leu Lys Asp Ala Arg Asp
 1               5                  10                  15
Lys Ile Val Glu Gly Thr Leu Tyr Ser Asn Val Ser Asp Leu Ile Gln
                20                  25                  30
Gln Phe Asn Gln Met Ile Val Thr Met Asn Gly Asn Asp Phe Gln Thr
            35                  40                  45
Gly Gly Ile Gly Asn Leu Pro Val Arg Asn Trp Thr Phe Asp Phe Gly
        50                  55                  60
Leu Leu Gly Thr Thr Leu Leu Asn Leu Asp Ala Asn Tyr Val Glu Asn
65                  70                  75                  80
Ala Arg Thr Ile Ile Glu Tyr Phe Ile Asp Phe Ile Asp Asn Val Cys
                85                  90                  95
Met Asp Glu Met Ala Arg Glu Ser Gln Arg Asn Gly Val Ala Pro Gln
            100                 105                 110
Ser Glu Ala Leu Arg Lys Leu Ala Gly Ile Lys Phe Lys Arg Ile Asn
        115                 120                 125
Phe Asp Asn Ser Ser Glu Tyr Ile Glu Asn Trp Asn Leu Gln Asn Arg
    130                 135                 140
Arg Gln Arg Thr Gly Phe Val Phe His Lys Pro Asn Ile Phe Pro Tyr
145                 150                 155                 160
Ser Ala Ser Phe Thr Leu Asn Arg Ser Gln Pro Met His Asp Asn Leu
                165                 170                 175
Met Gly Thr Met Trp Leu Asn Ala Gly Ser Glu Ile Gln Val Ala Gly
            180                 185                 190
Phe Asp Tyr Ser Cys Ala Ile Asn Ala Pro Ala Asn Ile Gln Gln Phe
        195                 200                 205
Glu His Ile Val Gln Leu Arg Arg Ala Leu Thr Thr Ala Thr Ile Thr
    210                 215                 220
Leu Leu Pro Asp Ala Glu Arg Phe Ser Phe Pro Arg Val Ile Asn Ser
225                 230                 235                 240
Ala Asp Gly Ala Thr Thr Trp Phe Phe Asn Pro Val Ile Leu Arg Pro
                245                 250                 255
Asn Asn Val Glu Val Glu Phe Leu Leu Asn Gly Gln Ile Ile Asn Thr
            260                 265                 270
Tyr Gln Ala Arg Phe Gly Thr Ile Ile Ala Arg Asn Phe Asp Ala Ile
        275                 280                 285
Arg Leu Leu Phe Gln Leu Met Arg Pro Pro Asn Met Thr Pro Ala Val
    290                 295                 300
Asn Ala Leu Phe Pro Gln Ala Gln Pro Phe Gln His His Ala Thr Val
305                 310                 315                 320
Gly Leu Thr Leu Arg Ile Glu Ser Ala Val Cys Glu Ser Val Leu Ala
                325                 330                 335
Asp Ala Asn Glu Thr Leu Leu Ala Asn Val Thr Ala Val Arg Gln Glu
            340                 345                 350
Tyr Ala Ile Pro Val Gly Pro Val Phe Pro Pro Gly Met Asn Trp Thr
        355                 360                 365
Glu Leu Ile Thr Asn Tyr Ser Pro Ser Arg Glu Asp Asn Leu Gln Arg
```

```
                    370                      375                      380
     Val  Phe  Thr  Val  Ala  Ser  Ile  Arg  Ser  Met  Leu  Ile  Lys
     385                 390                      395
```

( 2 ) INFORMATION FOR SEQ ID NO:11:

( i ) SEQUENCE CHARACTERISTICS:
      ( A ) LENGTH: 394 amino acids
      ( B ) TYPE: amino acid
      ( C ) STRANDEDNESS: unknown
      ( D ) TOPOLOGY: unknown ( i i ) MOLECULE TYPE: protein ( x i ) SEQUENCE DESCRIPTION: SEQ ID NO:11:

```
Met  Asp  Val  Leu  Phe  Ser  Ile  Ala  Lys  Thr  Val  Ser  Asp  Leu  Lys  Lys
1                   5                        10                       15

Lys  Val  Val  Val  Gly  Thr  Ile  Tyr  Thr  Asn  Val  Glu  Asp  Ile  Ile  Gln
               20                       25                       30

Gln  Thr  Asn  Glu  Leu  Ile  Arg  Thr  Leu  Asn  Gly  Asn  Thr  Phe  His  Thr
          35                       40                       45

Gly  Gly  Ile  Gly  Thr  Gln  Pro  Gln  Lys  Glu  Trp  Asn  Phe  Gln  Leu  Pro
     50                       55                       60

Gln  Leu  Gly  Thr  Thr  Leu  Leu  Asn  Leu  Asp  Asp  Asn  Tyr  Val  Gln  Ala
65                       70                       75                       80

Thr  Arg  Ser  Val  Ile  Asp  Tyr  Leu  Ala  Ser  Phe  Ile  Glu  Ala  Val  Cys
                    85                       90                       95

Asp  Asp  Glu  Ile  Val  Arg  Glu  Ala  Ser  Arg  Asn  Gly  Met  Gln  Pro  Gln
               100                      105                      110

Ser  Pro  Thr  Leu  Ile  Ala  Leu  Ala  Ser  Ser  Lys  Phe  Lys  Thr  Ile  Asn
          115                      120                      125

Phe  Asn  Asn  Ser  Ser  Gln  Ser  Ile  Lys  Asn  Trp  Ser  Ala  Gln  Ser  Gly
     130                      135                      140

Val  Arg  Ile  Gln  Phe  Met  Asn  Ile  Asn  Pro  Met  Val  Phe  Glu  Tyr  Arg
145                      150                      155                      160

Asn  Ser  Tyr  Ile  Leu  Gln  Arg  Ala  Asn  Pro  Gln  Tyr  Gly  Asn  Val  Met
                    165                      170                      175

Gly  Leu  Arg  Tyr  Tyr  Thr  Ala  Ser  Asn  Thr  Cys  Gln  Leu  Ala  Ala  Phe
               180                      185                      190

Asp  Ser  Thr  Leu  Ala  Glu  Asn  Ala  Pro  Asn  Asn  Thr  Gln  Arg  Phe  Ile
          195                      200                      205

Tyr  Asn  Gly  Arg  Leu  Lys  Arg  Pro  Ile  Ser  Asn  Val  Leu  Met  Lys  Ile
     210                      215                      220

Glu  Ala  Gly  Ala  Pro  Asn  Ile  Asn  Asn  Leu  Thr  Ile  Leu  Pro  Asp  Pro
225                      230                      235                      240

Thr  Asn  Gln  Thr  Thr  Trp  Leu  Tyr  Asn  Pro  Asp  Gln  Leu  Met  Asn  Gly
                    245                      250                      255

Thr  Phe  Thr  Ile  Glu  Phe  Tyr  Asn  Asn  Gly  Gln  Leu  Val  Asp  Met  Val
               260                      265                      270

Arg  Asn  Met  Gly  Val  Val  Thr  Val  Arg  Thr  Phe  Asp  Ser  Tyr  Arg  Ile
          275                      280                      285

Thr  Ile  Asp  Met  Ile  Arg  Pro  Ala  Ala  Met  Thr  Gln  Tyr  Val  Gln  Arg
     290                      295                      300

Leu  Phe  Pro  Gln  Gly  Gly  Pro  Tyr  Pro  Tyr  Gln  Ala  Ala  Tyr  Met  Leu
305                      310                      315                      320

Thr  Leu  Ser  Ile  Leu  Asp  Ala  Thr  Thr  Glu  Ser  Val  Leu  Cys  Asp  Ser
                    325                      330                      335

His  Ser  Val  Asp  Tyr  Ser  Ile  Val  Ala  Asn  Trp  Arg  Arg  Asp  Ser  Ala
```

-continued

```
                  340                         345                         350
        Met Pro Ala Gly Thr Val Phe Gln Pro Gly Phe Pro Trp Glu Gln Thr
                355                         360                 365

Leu Ser Asn Tyr Thr Val Ala Gln Glu Asp Asn Leu Glu Arg Leu Leu
                370                         375                 380

Leu Val Ala Ser Val Lys Arg Met Val Met
        385                 390
```

( 2 ) INFORMATION FOR SEQ ID NO:12:

( i ) SEQUENCE CHARACTERISTICS:
( A ) LENGTH: 775 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:12:

```
        Met Ala Ser Leu Ile Tyr Arg Gln Leu Leu Ser Asn Ser Tyr Val Thr
        1               5                   10                  15

Asn Ile Ser Asp Glu Val Asn Glu Ile Gly Thr Lys Lys Thr Thr Asn
                        20                  25                  30

Val Thr Val Asn Pro Gly Pro Phe Ala Gln Thr Gly Tyr Ala Pro Val
                        35                  40                  45

Asp Trp Gly His Gly Glu Leu Pro Asp Ser Thr Leu Val Gln Pro Thr
                50                  55                  60

Leu Asp Gly Pro Tyr Gln Pro Thr Leu Asn Leu Pro Val Thr Asp Tyr
        65                  70                  75                  80

Trp Met Leu Ile Ala Pro Thr Arg Glu Gly Lys Val Ala Glu Gly Thr
                        85                  90                  95

Asn Thr Thr Asp Arg Trp Phe Ala Cys Val Leu Val Glu Pro Asn Val
                        100                 105                 110

Gln Asn Thr Gln Arg Gln Tyr Val Leu Asp Gly Gln Asn Val Gln Leu
                        115                 120                 125

His Val Ser Asn Asp Ser Ser Thr Ser Trp Lys Phe Ile Leu Phe Ile
                130                 135                 140

Lys Leu Thr Pro Tyr Gly Thr Tyr Thr Gln Tyr Ser Thr Leu Ser Thr
        145                 150                 155                 160

Pro His Lys Leu Cys Ala Trp Met Lys Arg Asp Asn Arg Val Tyr Trp
                        165                 170                 175

Tyr Gln Gly Ala Thr Pro Asn Ala Ser Glu Ser Tyr Tyr Leu Thr Ile
                        180                 185                 190

Asn Asn Asp Asn Ser Asn Val Ser Ser Asp Ala Glu Phe Tyr Leu Ile
                        195                 200                 205

Pro Gln Ser Gln Thr Ala Met Cys Thr Gln Tyr Ile Asn Asn Gly Leu
                210                 215                 220

Pro Pro Ile Gln Asn Thr Arg Asn Ile Val Pro Val Asn Ile Thr Ser
        225                 230                 235                 240

Arg Gln Ile Lys Asp Val Arg Ala Gln Met Asn Glu Asp Ile Val Ile
                        245                 250                 255

Ser Lys Thr Ser Leu Trp Lys Glu Met Gln Tyr Asn Arg Asp Ile Ile
                        260                 265                 270

Ile Arg Phe Lys Phe Ala Asn Ser Ile Ile Lys Ser Gly Gly Leu Gly
                        275                 280                 285

Tyr Lys Trp Ser Glu Ile Ser Phe Lys Pro Met Asn Tyr Gln Tyr Thr
                290                 295                 300

Tyr Thr Arg Asp Glu Glu Glu Val Thr Ala His Thr Thr Cys Ser Val
```

-continued

| | | | | | | | | | | | | | | |
|---|---|---|---|---|---|---|---|---|---|---|---|---|---|---|
| 305 | | | | 310 | | | | 315 | | | | 320 | | |
| Asn | Gly | Val | Asn 325 | Asp | Phe | Asn | Tyr | Asn 330 | Gly | Gly | Thr | Leu | Pro 335 | Thr | Asp |
| Phe | Ala | Ile | Ser 340 | Arg | Phe | Glu | Val | Ile 345 | Lys | Glu | Asn | Ser | Tyr 350 | Val | Tyr |
| Val | Asp | Tyr 355 | Trp | Asp | Asp | Ser | Gln 360 | Ala | Phe | Arg | Asn | Met 365 | Val | Tyr | Val |
| Arg | Ser 370 | Leu | Ala | Ala | Asn | Leu 375 | Asn | Asp | Val | Val | Cys 380 | Thr | Gly | Gly | Ser |
| Tyr 385 | Ser | Phe | Ala | Leu | Pro 390 | Val | Gly | Asn | His | Pro 395 | Val | Met | Ser | Gly | Gly 400 |
| Ala | Val | Thr | Leu | Thr 405 | Ser | Ala | Gly | Val | Thr 410 | Leu | Ser | Thr | Gln | Tyr 415 | Thr |
| Asp | Tyr | Val | Ser 420 | Leu | Asn | Ser | Leu | Gln 425 | Phe | Arg | Phe | Arg | Leu 430 | Ala | Val |
| Ser | Glu | Pro 435 | Ser | Phe | Ser | Ile | Ser 440 | Arg | Thr | Arg | Met | Ser 445 | Gly | Ile | Tyr |
| Gly | Leu 450 | Pro | Ala | Val | Asn | Pro 455 | Asn | Asn | Ser | Ala | Glu 460 | Tyr | Tyr | Glu | Ile |
| Ala 465 | Gly | Arg | Phe | Ser | Leu 470 | Ile | Ser | Leu | Val | Pro 475 | Thr | Asn | Asp | Asp | Tyr 480 |
| Gln | Thr | Pro | Ile | Ala 485 | Asn | Ser | Val | Thr | Val 490 | Arg | Gln | Asp | Leu | Glu 495 | Arg |
| Gln | Leu | Gly | Glu 500 | Leu | Arg | Glu | Glu | Phe 505 | Asn | Ser | Leu | Ser | Gln 510 | Glu | Ile |
| Ala | Val | Ser 515 | Gln | Leu | Ile | Asp | Leu 520 | Ala | Thr | Leu | Pro | Leu 525 | Asp | Met | Phe |
| Ser | Met 530 | Phe | Ser | Gly | Ile | Lys 535 | Ser | Thr | Val | Glu | Ala 540 | Val | Lys | Ser | Met |
| Thr 545 | Thr | Asn | Val | Met | Lys 550 | Arg | Phe | Lys | Thr | Ser 555 | Ser | Leu | Ala | Asn | Ala 560 |
| Ile | Ser | Asp | Leu | Thr 565 | Ser | Asn | Met | Ser | Glu 570 | Ala | Ala | Ser | Ser | Val 575 | Arg |
| Leu | Thr | Ser | Val 580 | Arg | Ser | Val | Gly | Thr 585 | Ile | Thr | Leu | Pro | Arg 590 | Ala | Arg |
| Val | Ser | Leu 595 | Gln | Val | Gly | Asp | Asp 600 | Leu | Arg | Ser | Met | Gln 605 | Asp | Val | Ser |
| Thr | Gln 610 | Val | Ser | Asn | Val | Ser 615 | Arg | Asn | Leu | Arg | Leu 620 | Lys | Glu | Phe | Thr |
| Thr 625 | Gln | Thr | Asp | Thr | Leu 630 | Ser | Phe | Asp | Asp | Ile 635 | Ser | Ala | Ala | Val | Leu 640 |
| Lys | Thr | Lys | Leu | Asp 645 | Lys | Ser | Thr | Gln | Ile 650 | Ser | Gln | Gln | Thr | Met 655 | Pro |
| Asp | Ile | Ile | Ala 660 | Glu | Ser | Ser | Glu | Lys 665 | Phe | Ile | Pro | Lys | Arg 670 | Ser | Tyr |
| Arg | Ile | Val 675 | Asp | Glu | Asp | Ile | Arg 680 | Phe | Glu | Thr | Gly | Ile 685 | Asp | Gly | Thr |
| Phe | Tyr 690 | Ala | Tyr | Lys | Val | Asp 695 | Thr | Phe | Asn | Glu | Ile 700 | Pro | Phe | Asp | Met |
| Glu 705 | Arg | Phe | Asn | Lys | Leu 710 | Ile | Thr | Asp | Ser | Pro 715 | Val | Leu | Ser | Ala | Ile 720 |
| Ile | Asp | Phe | Lys | Thr 725 | Leu | Lys | Asn | Leu | Asn 730 | Asp | Asn | Tyr | Gly | Ile 735 | Thr |
| Lys | Lys | Gln | Ala 740 | Met | Glu | Leu | Leu | His 745 | Ser | Asn | Pro | Lys 750 | Thr | Leu | Lys |

Glu Phe Ile Asn Asn Asn Asn Pro Ile Ile Arg Asn Arg Ile Glu Asn
    755                 760                 765

Leu Ile Ser Gln Cys Arg Leu
    770             775

( 2 ) INFORMATION FOR SEQ ID NO:13:

( i ) SEQUENCE CHARACTERISTICS:
    ( A ) LENGTH: 775 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:13:

Met Ala Ser Leu Ile Tyr Arg Gln Leu Leu Thr Asn Ser Tyr Ser Val
1               5                   10                  15

Asp Leu His Asp Glu Ile Glu Gln Ile Gly Ser Glu Lys Thr Gln Asn
            20                  25                  30

Val Thr Val Asn Pro Gly Pro Phe Ala Gln Thr Arg Tyr Ala Pro Val
        35                  40                  45

Asn Trp Gly His Gly Glu Ile Asn Asp Ser Thr Thr Val Glu Pro Ile
    50                  55                  60

Leu Asp Gly Pro Tyr Gln Pro Thr Thr Phe Lys Pro Leu Thr Asp Tyr
65                  70                  75                  80

Trp Ile Leu Ile Asn Ser Asn Thr Asn Gly Val Val Tyr Glu Ser Thr
            85                  90                  95

Asn Asn Ser Asp Phe Trp Thr Ala Val Val Ala Ile Glu Pro His Val
            100                 105                 110

Ile Gln Val Asp Arg Gln Tyr Thr Val Phe Gly Glu Asn Lys Gln Phe
        115                 120                 125

Asn Val Arg Asn Asp Ser Asp Lys Trp Lys Phe Leu Glu Met Phe Arg
    130                 135                 140

Gly Ser Ser Gln Asn Glu Phe Tyr Asn Arg Arg Thr Leu Thr Ser Asp
145                 150                 155                 160

Thr Lys Leu Val Gly Ile Leu Lys Tyr Gly Gly Arg Ile Trp Thr Phe
                165                 170                 175

His Gly Glu Thr Pro Arg Ala Thr Thr Asp Ser Ser Asn Thr Ala Asn
            180                 185                 190

Leu Asn Asp Ile Ser Ile Ile His Ser Glu Phe Tyr Ile Ile Pro
        195                 200                 205

Arg Ser Gln Glu Ser Lys Cys Asn Glu Tyr Ile Asn Asn Gly Leu Pro
    210                 215                 220

Pro Ile Gln Asn Thr Arg Asn Val Val Pro Leu Ser Leu Ser Ser Arg
225                 230                 235                 240

Ser Ile Gln Tyr Lys Arg Ala Gln Val Asn Glu Asp Ile Thr Ile Ser
                245                 250                 255

Lys Thr Ser Leu Trp Lys Glu Met Gln Cys Asn Arg Asp Ile Ile Ile
            260                 265                 270

Arg Phe Lys Phe Gly Asn Ser Ile Val Lys Leu Gly Gly Leu Gly Tyr
        275                 280                 285

Lys Trp Ser Glu Ile Ser Tyr Lys Ala Ala Asn Tyr Gln Tyr Asn Tyr
    290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

| | | | | | | | | | | | | | | |
|---|---|---|---|---|---|---|---|---|---|---|---|---|---|---|
|Ser|Val|Ser|Arg<br>340|Tyr|Glu|Val|Ile|Lys<br>345|Glu|Asn|Ser|Tyr<br>350|Val|Tyr|Val|
|Asp|Tyr|Trp|Asp<br>355|Asp|Ser|Lys|Ala|Phe<br>360|Arg|Asn|Met|Val<br>365|Tyr|Val|Arg|
|Ser|Leu|Ala|Ala<br>370|Asn|Leu|Asn|Ser|Val<br>375|Lys|Cys|Thr|Gly<br>380|Gly|Ser|Tyr|
|Asp<br>385|Phe|Ser|Ile|Pro|Val<br>390|Gly|Ala|Trp|Pro|Val<br>395|Met|Asn|Gly|Gly|Ala<br>400|
|Val|Ser|Leu|His|Phe<br>405|Ala|Gly|Val|Thr|Leu<br>410|Ser|Thr|Gln|Phe|Thr<br>415|Asp|
|Phe|Val|Ser|Leu<br>420|Asn|Ser|Leu|Arg|Phe<br>425|Arg|Phe|Ser|Leu<br>430|Thr|Val|Asp|
|Glu|Pro|Ser<br>435|Phe|Ser|Ile|Leu|Arg<br>440|Thr|Arg|Thr|Val|Asn<br>445|Leu|Tyr|Gly|
|Leu|Pro|Ala<br>450|Ala|Asn|Pro|Asn|Asn<br>455|Gly|Asn|Glu|Tyr|Tyr<br>460|Glu|Ile|Ser|
|Gly<br>465|Arg|Phe|Ser|Leu|Ile<br>470|Ser|Leu|Val|Pro|Thr<br>475|Asn|Asp|Asp|Tyr|Gln<br>480|
|Thr|Pro|Ile|Met|Asn<br>485|Ser|Val|Thr|Val|Arg<br>490|Gln|Asp|Leu|Glu|Arg<br>495|Gln|
|Leu|Thr|Asp|Leu<br>500|Arg|Glu|Glu|Phe|Asn<br>505|Ser|Leu|Ser|Gln|Glu<br>510|Ile|Ala|
|Met|Ser|Gln<br>515|Leu|Ile|Asp|Leu|Ala<br>520|Leu|Leu|Pro|Leu|Asp<br>525|Met|Phe|Ser|
|Met|Phe|Ser<br>530|Glu|Leu|Lys|Ser|Thr<br>535|Ile|Asp|Leu|Thr|Lys<br>540|Ser|Met|Ala|
|Thr<br>545|Ser|Val|Met|Lys|Lys<br>550|Phe|Arg|Lys|Ser|Lys<br>555|Leu|Ala|Thr|Ser|Ile<br>560|
|Ser|Glu|Met|Thr|His<br>565|Ser|Leu|Ser|Asp|Ala<br>570|Ala|Ser|Ser|Ala|Ser<br>575|Arg|
|Ser|Val|Ser|Ile<br>580|Arg|Ser|Asn|Ile|Ser<br>585|Thr|Ile|Ser|Asn|Trp<br>590|Thr|Asn|
|Val|Ser|Asn<br>595|Asp|Val|Ser|Asn|Val<br>600|Thr|Asn|Ser|Leu|Ser<br>605|Asp|Ile|Ser|
|Thr|Gln|Thr<br>610|Ser|Thr|Ile|Ser|Lys<br>615|Asn|Leu|Arg|Leu|Lys<br>620|Glu|Met|Ile|
|Thr|Gln<br>625|Thr|Glu|Gly|Met|Ser<br>630|Phe|Asp|Asp|Ile|Ser<br>635|Ala|Ala|Val|Leu<br>640|
|Lys|Thr|Lys|Ile|Asp<br>645|Met|Ser|Thr|Gln|Ile<br>650|Gly|Lys|Asn|Thr|Leu<br>655|Pro|
|Asp|Ile|Val|Thr<br>660|Glu|Ala|Ser|Glu|Lys<br>665|Phe|Ile|Pro|Lys|Arg<br>670|Ser|Tyr|
|Arg|Ile|Leu|Lys<br>675|Asp|Asp|Glu|Val|Met<br>680|Glu|Ile|Asn|Thr<br>685|Glu|Gly|Lys|
|Val|Phe|Ala<br>690|Tyr|Lys|Ile|Asp|Thr<br>695|Leu|Asn|Glu|Val|Pro<br>700|Phe|Asp|Val|
|Asn<br>705|Lys|Phe|Ala|Glu|Leu<br>710|Val|Thr|Asn|Ser|Pro<br>715|Val|Ile|Ser|Ala|Ile<br>720|
|Ile|Asp|Phe|Lys|Thr<br>725|Leu|Lys|Asn|Leu|Asn<br>730|Asp|Asn|Tyr|Gly|Ile<br>735|Thr|
|Arg|Ile|Glu|Ala|Leu<br>740|Asn|Leu|Ile|Lys|Ser<br>745|Asn|Pro|Asn|Val|Leu<br>750|Arg|
|Asn|Phe|Ile|Asn|Gln<br>755|Asn|Asn|Pro|Ile|Ile<br>760|Arg|Asn|Arg|Ile|Glu<br>765|Gln|

(2) INFORMATION FOR SEQ ID NO:14:

(i) SEQUENCE CHARACTERISTICS:
      (A) LENGTH: 775 amino acids
      (B) TYPE: amino acid
      (C) STRANDEDNESS: unknown
      (D) TOPOLOGY: unknown (ii) MOLECULE TYPE: protein (xi) SEQUENCE DESCRIPTION: SEQ ID NO:14:

```
Leu Ile Leu Gln Cys Lys Leu
    770             775

Met Ala Ser Leu Ile Tyr Arg Gln Leu Leu Thr Asn Ser Tyr Ser Val
  1           5                  10                  15

Asp Leu His Asp Glu Ile Glu Gln Ile Gly Ser Glu Lys Thr Gln Ser
             20                  25                  30

Val Thr Val Asn Pro Gly Pro Phe Ala Gln Thr Arg Tyr Ala Pro Val
         35                  40                  45

Asn Trp Gly His Gly Glu Ile Asn Asp Ser Thr Thr Val Glu Pro Val
     50                  55                  60

Leu Asp Gly Pro Tyr Gln Pro Thr Thr Phe Lys Pro Pro Thr Asp Tyr
 65                  70                  75                  80

Trp Leu Leu Ile Ser Ser Asn Thr Asn Gly Val Val Tyr Glu Ser Thr
                 85                  90                  95

Asn Asn Asn Asp Phe Trp Thr Ala Val Ile Ala Ile Glu Pro His Val
            100                 105                 110

Ser Gln Val Asn Arg Gln Tyr Thr Leu Phe Gly Glu Asn Lys Gln Phe
            115                 120                 125

Asn Val Glu Asn Asn Ser Asp Lys Trp Lys Phe Phe Glu Met Phe Lys
    130                 135                 140

Gly Ser Ser Gln Gly Asn Phe Ser Asn Arg Arg Thr Leu Thr Ser Ser
145                 150                 155                 160

Asn Arg Leu Val Gly Met Leu Lys Tyr Gly Gly Arg Val Trp Thr Phe
                165                 170                 175

His Gly Glu Thr Pro Arg Ala Thr Thr Asp Ser Ser Asn Thr Ala Asp
            180                 185                 190

Leu Asn Asn Ile Ser Ile Ile His Ser Glu Phe Tyr Ile Ile Pro
    195                 200                 205

Arg Ser Gln Glu Ser Lys Cys Asn Glu Tyr Ile Asn Asn Gly Leu Pro
210                 215                 220

Pro Ile Gln Asn Thr Arg Asn Val Val Pro Leu Ser Leu Ser Ser Arg
225                 230                 235                 240

Ser Ile Gln Tyr Arg Arg Ala Gln Val Asn Glu Asp Ile Thr Ile Ser
            245                 250                 255

Lys Thr Ser Leu Trp Lys Glu Met Gln Tyr Asn Arg Asp Ile Ile Ile
            260                 265                 270

Arg Phe Lys Phe Gly Asn Ser Val Ile Lys Leu Gly Gly Leu Gly Tyr
            275                 280                 285

Lys Trp Ser Glu Ile Ser Tyr Lys Ala Ala Asn Tyr Gln Tyr Ser Tyr
    290                 295                 300

Ser Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Ile Ser Arg Tyr Glu Val Ile Lys Glu Asn Ser Tyr Val Tyr Ile
            340                 345                 350
```

|     |     |     |     |     |     |     |     |     |     |     |     |     |     |     |
|-----|-----|-----|-----|-----|-----|-----|-----|-----|-----|-----|-----|-----|-----|-----|
| Asp | Tyr | Trp<br>355 | Asp | Asp | Ser | Lys<br>360 | Ala | Phe | Arg | Asn | Met<br>365 | Val | Tyr | Val | Arg |
| Ser | Leu<br>370 | Ala | Ala | Asn | Leu<br>375 | Asn | Ser | Val | Lys | Cys<br>380 | Thr | Gly | Gly | Ser | Tyr |
| Asn<br>385 | Phe | Arg | Leu | Pro | Val<br>390 | Gly | Lys | Trp | Pro | Ile<br>395 | Met | Asn | Gly | Gly | Ala<br>400 |
| Val | Ser | Leu | His | Phe<br>405 | Ala | Gly | Val | Thr | Leu<br>410 | Ser | Thr | Gln | Phe | Thr<br>415 | Asp |
| Phe | Val | Ser | Leu<br>420 | Asn | Ser | Leu | Arg | Phe<br>425 | Arg | Phe | Ser | Leu | Thr<br>430 | Val | Asp |
| Glu | Pro | Ser<br>435 | Phe | Ser | Ile | Leu | Arg<br>440 | Thr | Arg | Thr | Ile | Asn<br>445 | Leu | Tyr | Gly |
| Leu | Pro<br>450 | Ala | Ala | Asn | Pro | Asn<br>455 | Asn | Gly | Asn | Glu | Tyr<br>460 | Tyr | Glu | Met | Ser |
| Gly<br>465 | Arg | Phe | Ser | Leu | Ile<br>470 | Ser | Leu | Val | Gln | Thr<br>475 | Asn | Asp | Asp | Tyr | Gln<br>480 |
| Thr | Pro | Ile | Met | Asn<br>485 | Ser | Val | Thr | Val | Arg<br>490 | Gln | Asp | Leu | Glu | Arg<br>495 | Gln |
| Leu | Asn | Asp | Leu<br>500 | Arg | Glu | Glu | Phe | Asn<br>505 | Ser | Leu | Ser | Gln | Glu<br>510 | Ile | Ala |
| Met | Ser | Gln<br>515 | Leu | Ile | Asp | Leu | Ala<br>520 | Leu | Leu | Pro | Leu | Asp<br>525 | Met | Phe | Ser |
| Met | Phe<br>530 | Ser | Gly | Ile | Lys | Ser<br>535 | Thr | Ile | Asp | Leu | Thr<br>540 | Lys | Ser | Met | Ala |
| Thr<br>545 | Ser | Val | Met | Lys | Lys<br>550 | Phe | Arg | Lys | Ser | Lys<br>555 | Leu | Ala | Thr | Ser | Ile<br>560 |
| Ser | Glu | Met | Thr | Asn<br>565 | Ser | Leu | Ser | Asp | Ala<br>570 | Ala | Ser | Ser | Ala | Ser<br>575 | Arg |
| Ser | Ala | Ser | Ile<br>580 | Arg | Ser | Asn | Ile | Ser<br>585 | Thr | Ile | Ser | Asn | Trp<br>590 | Thr | Asn |
| Thr | Ser | Lys<br>595 | Ser | Val | Ser | Asn | Val<br>600 | Thr | Asp | Ser | Val | Asn<br>605 | Asp | Ile | Ser |
| Thr | Gln<br>610 | Thr | Ser | Thr | Ile | Ser<br>615 | Lys | Lys | Leu | Arg | Leu<br>620 | Arg | Glu | Met | Ile |
| Thr<br>625 | Gln | Thr | Glu | Gly | Leu<br>630 | Ser | Phe | Asp | Asp | Ile<br>635 | Ser | Ala | Ala | Val | Leu<br>640 |
| Lys | Thr | Lys | Ile | Asp<br>645 | Met | Ser | Thr | Gln | Ile<br>650 | Gly | Lys | Asn | Thr | Leu<br>655 | Pro |
| Asp | Ile | Val | Thr<br>660 | Glu | Ala | Ser | Glu | Lys<br>665 | Phe | Ile | Pro | Lys | Arg<br>670 | Ser | Tyr |
| Arg | Val | Leu<br>675 | Lys | Asp | Asp | Glu | Val<br>680 | Met | Glu | Ile | Asn | Thr<br>685 | Glu | Gly | Lys |
| Phe | Phe<br>690 | Ala | Tyr | Lys | Val | Asp<br>695 | Thr | Leu | Asn | Glu | Ile<br>700 | Pro | Phe | Asp | Ile |
| Asn<br>705 | Lys | Phe | Ala | Glu | Leu<br>710 | Val | Thr | Asp | Ser | Pro<br>715 | Val | Ile | Ser | Ala | Ile<br>720 |
| Ile | Asp | Phe | Lys | Thr<br>725 | Leu | Lys | Asn | Leu | Asn<br>730 | Asp | Asn | Tyr | Gly | Ile<br>735 | Thr |
| Arg | Ile | Glu | Ala | Phe<br>740 | Asn | Leu | Ile | Lys<br>745 | Ser | Asn | Pro | Asn | Val<br>750 | Leu | Arg |
| Asn | Phe | Ile<br>755 | Asn | Gln | Asn | Asn | Pro<br>760 | Ile | Ile | Arg | Asn | Arg<br>765 | Ile | Glu | Gln |
| Leu | Ile<br>770 | Leu | Gln | Cys | Lys<br>775 | Leu |     |     |     |     |     |     |     |     |     |

( 2 ) INFORMATION FOR SEQ ID NO:15:

( i ) SEQUENCE CHARACTERISTICS:
        ( A ) LENGTH: 775 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:15:

```
Met Ala Ser Leu Ile Tyr Arg Gln Leu Leu Thr Asn Ser Tyr Ser Val
 1               5                  10                  15

Glu Leu Ser Asp Glu Ile Asn Thr Ile Gly Ser Glu Lys Thr Gln Asn
            20                  25                  30

Val Thr Ile Asn Pro Gly Pro Phe Ala Gln Thr Asn Tyr Ala Pro Val
         35                  40                  45

Val Leu Glu Ser Trp Glu Val Asn Asp Ser Thr Thr Ile Glu Pro Val
 50                  55                  60

Leu Asp Gly Pro Tyr Gln Pro Thr Phe Lys Pro Pro Ser Thr Asp Tyr
 65                  70                  75                  80

Trp Ile Leu Leu Asn Pro Thr Asp Gln Gln Val Val Leu Glu Gly Thr
                 85                  90                  95

Asn Lys Thr Asp Ile Trp Ile Ala Leu Leu Leu Val Glu Pro Asn Val
            100                 105                 110

Thr Asn Gln Ser Arg Gln Tyr Thr Leu Phe Gly Glu Thr Lys Gln Ile
         115                 120                 125

Thr Val Glu Asn Asn Thr Asn Lys Trp Lys Phe Phe Glu Met Phe Arg
130                 135                 140

Lys Asn Val Ser Ala Glu Phe Gln His Lys Arg Thr Leu Thr Ser Asp
145                 150                 155                 160

Thr Lys Leu Ala Gly Phe Leu Lys His Tyr Asn Ser Val Trp Thr Phe
                165                 170                 175

His Gly Glu Thr Pro His Ala Thr Thr Asp Tyr Ser Ser Thr Ser Asn
            180                 185                 190

Leu Ser Glu Val Glu Thr Val Ile His Val Glu Phe Tyr Ile Ile Pro
         195                 200                 205

Arg Ser Gln Glu Ser Lys Cys Val Glu Tyr Ile Asn Thr Gly Leu Pro
210                 215                 220

Pro Met Gln Asn Thr Arg Asn Ile Val Pro Val Ala Leu Ser Ser Arg
225                 230                 235                 240

Ser Val Thr Tyr Gln Arg Ala Gln Val Asn Glu Asp Ile Ile Ile Ser
                245                 250                 255

Lys Thr Ser Leu Trp Lys Glu Met Gln Cys Asn Arg Asp Ile Ile Ile
            260                 265                 270

Arg Phe Lys Phe Asn Asn Ser Ile Val Lys Leu Gly Gly Leu Gly Tyr
         275                 280                 285

Lys Trp Ser Glu Ile Ser Phe Lys Ala Ala Asn Tyr Gln Tyr Asn Tyr
290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Ser Leu Pro Thr Asp Phe
                325                 330                 335

Ser Val Ser Arg Tyr Glu Val Ile Lys Glu Asn Ser Tyr Val Tyr Val
            340                 345                 350

Asp Tyr Trp Asp Asp Ser Gln Ala Phe Arg Asn Met Val Tyr Val Arg
         355                 360                 365

Ser Leu Ala Ala Asn Leu Asn Ser Val Lys Cys Thr Gly Gly Asn Tyr
```

-continued

|     |     |     | 370 |     |     |     | 375 |     |     |     | 380 |     |     |     |
|---|---|---|---|---|---|---|---|---|---|---|---|---|---|---|
| Asn | Phe | Gln | Leu | Pro | Val | Gly | Ala | Trp | Pro | Val | Met | Ser | Gly | Gly | Ala |
| 385 |     |     |     |     | 390 |     |     |     | 395 |     |     |     |     | 400 |
| Val | Ser | Leu | His | Phe | Ala | Gly | Val | Thr | Leu | Ser | Thr | Glu | Phe | Thr | Asp |
|     |     |     |     | 405 |     |     |     |     | 410 |     |     |     |     | 415 |
| Phe | Val | Ser | Leu | Asn | Ser | Leu | Arg | Phe | Arg | Phe | Ser | Leu | Thr | Val | Glu |
|     |     |     | 420 |     |     |     |     | 425 |     |     |     |     | 430 |     |
| Glu | Pro | Pro | Phe | Ser | Ile | Leu | Arg | Thr | Arg | Val | Ser | Gly | Leu | Tyr | Gly |
|     |     | 435 |     |     |     |     |     | 440 |     |     |     |     | 445 |     |
| Leu | Pro | Ala | Phe | Asn | Pro | Asn | Ser | Gly | His | Glu | Tyr | Tyr | Glu | Ile | Ala |
|     | 450 |     |     |     |     | 455 |     |     |     |     | 460 |     |     |     |
| Gly | Arg | Phe | Ser | Phe | Ile | Leu | Leu | Val | Pro | Ser | Asn | Asp | Asp | Tyr | Gln |
| 465 |     |     |     |     | 470 |     |     |     |     | 475 |     |     |     |     | 480 |
| Thr | Pro | Ile | Met | Asn | Ser | Val | Thr | Val | Arg | Gln | Asp | Leu | Glu | Arg | Gln |
|     |     |     |     | 485 |     |     |     |     | 490 |     |     |     |     | 495 |     |
| Leu | Gly | Asp | Leu | Arg | Glu | Glu | Phe | Asn | Ser | Leu | Ser | Gln | Glu | Ile | Ala |
|     |     |     | 500 |     |     |     |     | 505 |     |     |     |     | 510 |     |
| Met | Thr | Gln | Leu | Ile | Asp | Leu | Ala | Leu | Leu | Pro | Leu | Asp | Met | Phe | Ser |
|     |     | 515 |     |     |     |     | 520 |     |     |     |     | 525 |     |     |
| Met | Phe | Ser | Gly | Ile | Lys | Ser | Thr | Ile | Asp | Ala | Ala | Lys | Ser | Met | Ala |
|     | 530 |     |     |     |     | 535 |     |     |     |     | 540 |     |     |     |
| Thr | Lys | Val | Met | Lys | Lys | Phe | Lys | Arg | Ser | Gly | Leu | Ala | Thr | Ser | Ile |
| 545 |     |     |     |     | 550 |     |     |     |     | 555 |     |     |     |     | 560 |
| Ser | Glu | Leu | Thr | Gly | Ser | Leu | Ser | Asn | Ala | Ala | Ser | Ser | Ile | Ser | Arg |
|     |     |     |     | 565 |     |     |     |     | 570 |     |     |     |     | 575 |     |
| Ser | Ser | Ser | Ile | Arg | Ser | Asn | Ile | Ser | Ser | Ile | Ser | Val | Trp | Thr | Asp |
|     |     |     | 580 |     |     |     |     | 585 |     |     |     |     | 590 |     |
| Val | Ser | Glu | Gln | Ile | Ala | Gly | Ser | Ser | Asp | Ser | Val | Ser | Asn | Ile | Ser |
|     |     | 595 |     |     |     |     | 600 |     |     |     |     | 605 |     |     |
| Thr | Gln | Met | Ser | Ala | Ile | Ser | Arg | Arg | Leu | Arg | Leu | Arg | Glu | Ile | Thr |
|     | 610 |     |     |     |     | 615 |     |     |     |     | 620 |     |     |     |
| Thr | Gln | Thr | Glu | Gly | Met | Asn | Phe | Asp | Asp | Ile | Ser | Ala | Ala | Val | Leu |
| 625 |     |     |     |     | 630 |     |     |     |     | 635 |     |     |     |     | 640 |
| Lys | Thr | Lys | Ile | Asp | Arg | Ser | Thr | His | Ile | Ser | Pro | Asp | Thr | Leu | Pro |
|     |     |     |     | 645 |     |     |     |     | 650 |     |     |     |     | 655 |     |
| Asp | Ile | Met | Thr | Glu | Ser | Ser | Lys | Lys | Phe | Ile | Pro | Lys | Arg | Ala | Tyr |
|     |     |     | 660 |     |     |     |     | 665 |     |     |     |     | 670 |     |
| Arg | Val | Leu | Lys | Asp | Asp | Glu | Val | Met | Glu | Ala | Asp | Val | Asp | Gly | Lys |
|     |     | 675 |     |     |     |     | 680 |     |     |     |     | 685 |     |     |
| Phe | Phe | Ala | Tyr | Lys | Val | Asp | Thr | Phe | Glu | Glu | Val | Pro | Phe | Asp | Val |
|     | 690 |     |     |     |     | 695 |     |     |     |     | 700 |     |     |     |
| Asp | Lys | Phe | Val | Asp | Leu | Val | Thr | Asp | Ser | Pro | Val | Ile | Ser | Ala | Ile |
| 705 |     |     |     |     | 710 |     |     |     |     | 715 |     |     |     |     | 720 |
| Ile | Asp | Phe | Lys | Thr | Leu | Lys | Asn | Leu | Asn | Asp | Asn | Tyr | Gly | Ile | Thr |
|     |     |     |     | 725 |     |     |     |     | 730 |     |     |     |     | 735 |     |
| Arg | Ser | Gln | Ala | Leu | Asp | Leu | Ile | Arg | Ser | Asp | Pro | Arg | Val | Leu | Arg |
|     |     |     | 740 |     |     |     |     | 745 |     |     |     |     | 750 |     |
| Asp | Phe | Ile | Asn | Gln | Asn | Asn | Pro | Ile | Ile | Lys | Asn | Arg | Ile | Glu | Gln |
|     |     | 755 |     |     |     |     | 760 |     |     |     |     | 765 |     |     |
| Leu | Ile | Leu | Gln | Cys | Arg | Leu |
|     | 770 |     |     |     |     | 775 |

( 2 ) INFORMATION FOR SEQ ID NO:16:

( i ) SEQUENCE CHARACTERISTICS:
        ( A ) LENGTH: 775 amino acids (B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:16:

```
Met Ala Ser Leu Ile Tyr Arg Gln Leu Leu Thr Asn Ser Tyr Thr Val
 1               5                  10                  15

Glu Leu Ser Asp Glu Ile Asn Thr Ile Gly Ser Glu Lys Ser Gln Asn
            20                  25                  30

Ile Thr Ile Asn Pro Gly Pro Phe Ala Gln Thr Asn Tyr Ala Pro Val
        35                  40                  45

Val Leu Glu Ser Trp Glu Val Asn Asp Ser Thr Thr Ile Glu Pro Val
50                  55                  60

Leu Asp Gly Pro Tyr Gln Pro Thr Phe Lys Pro Pro Ser Thr Asp Tyr
65                  70                  75                  80

Trp Ile Leu Leu Asn Pro Thr Asn Gln Gln Val Val Leu Glu Gly Thr
                85                  90                  95

Asn Lys Thr Asp Ile Trp Ile Ala Leu Leu Leu Val Glu Pro Asn Val
            100                 105                 110

Thr Asn Gln Ser Arg Gln Tyr Thr Leu Phe Gly Glu Thr Lys Gln Ile
        115                 120                 125

Thr Val Glu Asn Asn Thr Asn Lys Trp Lys Phe Phe Glu Met Phe Arg
130                 135                 140

Ser Ser Val Ser Ser Glu Phe Gln His Lys Arg Thr Leu Thr Ser Asp
145                 150                 155                 160

Thr Lys Leu Ala Gly Phe Leu Lys His Tyr Asn Ser Val Trp Ser Phe
                165                 170                 175

His Gly Glu Thr Pro His Ala Thr Thr Asp Tyr Ser Ser Thr Ser Asn
            180                 185                 190

Leu Ser Glu Val Glu Thr Val Ile His Val Glu Phe Tyr Ile Ile Ser
        195                 200                 205

Arg Ser Gln Glu Ser Lys Cys Val Glu Tyr Ile Asn Thr Gly Leu Pro
210                 215                 220

Pro Met Gln Asn Thr Arg Asn Ile Val Pro Val Ala Leu Ser Ser Arg
225                 230                 235                 240

Ser Val Thr Tyr Gln Arg Ala Gln Val Asn Glu Asp Ile Ile Ile Ser
                245                 250                 255

Lys Thr Ser Leu Trp Lys Glu Met Gln Tyr Asn Arg Asp Ile Ile Ile
            260                 265                 270

Arg Phe Lys Phe Asn Asn Ser Ile Ile Lys Leu Gly Gly Leu Gly Tyr
        275                 280                 285

Lys Trp Ser Glu Ile Ser Phe Lys Ala Ala Asn Tyr Gln Tyr Asn Tyr
290                 295                 300

Leu Arg Asp Gly Glu Gln Val Thr Ala His Thr Thr Cys Ser Val Asn
305                 310                 315                 320

Gly Val Asn Asn Phe Ser Tyr Asn Gly Gly Leu Leu Pro Thr His Phe
                325                 330                 335

Ser Val Ser Arg Tyr Glu Val Ile Lys Glu Asn Ser Tyr Val Tyr Val
            340                 345                 350

Asn Tyr Trp Asp Asp Ser Gln Ala Leu Arg Asn Met Val Tyr Val Arg
        355                 360                 365

Ser Leu Ala Ala Asn Leu Asn Ser Val Lys Cys Thr Gly Gly Asn Tyr
370                 375                 380

Asn Phe Gln Leu Pro Val Gly Ala Trp Pro Val Met Ser Gly Gly Ala
385                 390                 395                 400
```

```
Val  Ser  Leu  His  Phe  Ala  Gly  Val  Thr  Leu  Ser  Thr  Lys  Phe  Thr  Asp
               405            410                      415

Phe  Val  Ser  Leu  Asn  Ser  Leu  Arg  Phe  Arg  Phe  Ser  Leu  Thr  Val  Glu
               420                 425                      430

Glu  Pro  Pro  Phe  Ser  Ile  Leu  Arg  Thr  Arg  Val  Ser  Gly  Leu  Tyr  Gly
               435                 440                      445

Leu  Pro  Ala  Ser  Asn  Pro  Asn  Ser  Gly  His  Glu  Tyr  Tyr  Glu  Ile  Ala
     450                      455                 460

Gly  Arg  Phe  Ser  Leu  Ile  Ser  Leu  Val  Pro  Ser  Asn  Asp  Asp  Tyr  Gln
465                      470                 475                           480

Thr  Pro  Ile  Met  Asn  Ser  Ile  Thr  Val  Arg  Gln  Asp  Leu  Glu  Arg  Gln
               485                      490                           495

Leu  Gly  Asp  Leu  Arg  Glu  Glu  Phe  Asn  Ser  Leu  Ser  Gln  Glu  Ile  Ala
               500                 505                      510

Ile  Thr  Gln  Leu  Ile  Asp  Leu  Ala  Leu  Leu  Pro  Leu  Asp  Met  Phe  Ser
          515                      520                 525

Met  Phe  Ser  Gly  Ile  Lys  Ser  Thr  Ile  Asp  Ala  Ala  Lys  Ser  Met  Ala
     530                 535                      540

Thr  Lys  Val  Met  Lys  Lys  Phe  Lys  Arg  Ser  Gly  Leu  Ala  Thr  Ser  Ile
545                      550                 555                           560

Ser  Glu  Leu  Thr  Arg  Ser  Leu  Ser  Asn  Ala  Ala  Ser  Ser  Ile  Ser  Arg
               565                      570                           575

Ser  Ser  Ser  Ile  Arg  Ser  Asn  Ile  Ser  Ser  Val  Ser  Glu  Trp  Thr  Asp
               580                 585                      590

Val  Ser  Glu  Gln  Ile  Ala  Gly  Ser  Ser  Asp  Ser  Val  Arg  Asn  Ile  Ser
          595                 600                      605

Thr  Gln  Ile  Ser  Ala  Ile  Ser  Arg  Arg  Leu  Arg  Leu  Arg  Glu  Ile  Thr
     610                      615                 620

Thr  Gln  Thr  Glu  Gly  Met  Asn  Phe  Ile  Asp  Ile  Ser  Ala  Ala  Val  Leu
625                      630                 635                           640

Lys  Thr  Lys  Ile  Asp  Arg  Ser  Thr  His  Ile  Arg  Pro  Asp  Thr  Leu  Pro
               645                 650                      655

Asp  Ile  Ile  Thr  Glu  Ser  Ser  Glu  Lys  Phe  Ile  Pro  Lys  Arg  Ala  Tyr
               660                 665                      670

Arg  Val  Leu  Lys  Asp  Asp  Glu  Val  Met  Glu  Ala  Asp  Val  Asp  Gly  Lys
          675                      680                 685

Phe  Phe  Ala  Tyr  Lys  Val  Asp  Thr  Phe  Glu  Glu  Val  Pro  Phe  Asp  Val
     690                      695                 700

Asp  Lys  Phe  Val  Asp  Leu  Val  Thr  Asp  Ser  Pro  Val  Ile  Ser  Ala  Ile
705                      710                 715                           720

Ile  Asp  Phe  Lys  Thr  Leu  Lys  Asn  Leu  Asn  Asp  Asn  Tyr  Gly  Ile  Thr
               725                 730                      735

Arg  Ser  Gln  Ala  Leu  Asp  Leu  Ile  Arg  Ser  Asp  Pro  Arg  Val  Leu  Arg
               740                 745                      750

Asp  Phe  Ile  Asn  Gln  Asn  Asn  Pro  Ile  Ile  Lys  Asn  Arg  Ile  Glu  Gln
               755                 760                      765

Leu  Ile  Leu  Gln  Cys  Arg  Leu
               770            775
```

(2) INFORMATION FOR SEQ ID NO:17:

( i ) SEQUENCE CHARACTERISTICS:
        ( A ) LENGTH: 776 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:17:

| Met | Ala | Ala | Leu | Ile | Tyr | Arg | Gln | Leu | Leu | Thr | Asn | Ser | Tyr | Thr | Val |
|---|---|---|---|---|---|---|---|---|---|---|---|---|---|---|---|
| 1 | | | | 5 | | | | | 10 | | | | | 15 | |
| Glu | Leu | Ser | Asp | Glu | Ile | Gln | Glu | Ile | Gly | Ser | Thr | Lys | Thr | Gln | Asn |
| | | | 20 | | | | | 25 | | | | | 30 | | |
| Val | Thr | Val | Asn | Pro | Gly | Pro | Phe | Ala | Gln | Thr | Asn | Tyr | Ala | Pro | Val |
| | | 35 | | | | | 40 | | | | | 45 | | | |
| Asn | Trp | Gly | Pro | Gly | Glu | Thr | Asn | Asp | Ser | Thr | Thr | Val | Glu | Pro | Val |
| | 50 | | | | | 55 | | | | | 60 | | | | |
| Leu | Asp | Gly | Pro | Tyr | Gln | Pro | Thr | Thr | Phe | Asn | Pro | Pro | Val | Ser | Tyr |
| 65 | | | | | 70 | | | | | 75 | | | | | 80 |
| Trp | Met | Leu | Leu | Ala | Pro | Thr | Asn | Ala | Gly | Val | Val | Val | Glu | Gly | Thr |
| | | | | 85 | | | | | 90 | | | | | 95 | |
| Asn | Asn | Thr | Asn | Arg | Trp | Leu | Ala | Thr | Ile | Leu | Ile | Glu | Pro | Asn | Val |
| | | | 100 | | | | | 105 | | | | | 110 | | |
| Gln | Gln | Val | Glu | Arg | Thr | Tyr | Thr | Leu | Phe | Gly | Gln | Gln | Val | Gln | Val |
| | | | 115 | | | | | 120 | | | | | 125 | | |
| Thr | Val | Ser | Asn | Asp | Ser | Gln | Thr | Lys | Trp | Lys | Phe | Val | Asp | Leu | Ser |
| | 130 | | | | | 135 | | | | | 140 | | | | |
| Lys | Gln | Thr | Gln | Asp | Gly | Asn | Tyr | Ser | Gln | His | Gly | Ser | Leu | Leu | Ser |
| 145 | | | | | 150 | | | | | 155 | | | | | 160 |
| Thr | Pro | Lys | Leu | Tyr | Gly | Val | Met | Lys | His | Gly | Gly | Lys | Ile | Tyr | Thr |
| | | | | 165 | | | | | 170 | | | | | 175 | |
| Tyr | Asn | Gly | Glu | Thr | Pro | Asn | Ala | Asn | Thr | Gly | Tyr | Tyr | Ser | Thr | Thr |
| | | | 180 | | | | | 185 | | | | | 190 | | |
| Asn | Phe | Asp | Thr | Val | Asn | Met | Thr | Ala | Tyr | Cys | Asp | Phe | Tyr | Ile | Ile |
| | | 195 | | | | | 200 | | | | | 205 | | | |
| Pro | Leu | Ala | Gln | Glu | Ala | Lys | Cys | Thr | Glu | Tyr | Ile | Asn | Asn | Gly | Leu |
| | 210 | | | | | 215 | | | | | 220 | | | | |
| Pro | Pro | Ile | Gln | Asn | Thr | Arg | Asn | Ile | Val | Pro | Val | Ser | Ile | Val | Ser |
| 225 | | | | | 230 | | | | | 235 | | | | | 240 |
| Arg | Asn | Ile | Val | Tyr | Thr | Arg | Ala | Gln | Pro | Asn | Gln | Asp | Ile | Val | Val |
| | | | | 245 | | | | | 250 | | | | | 255 | |
| Ser | Lys | Thr | Ser | Leu | Trp | Lys | Glu | Met | Gln | Tyr | Asn | Arg | Asp | Ile | Val |
| | | | 260 | | | | | 265 | | | | | 270 | | |
| Ile | Arg | Phe | Lys | Phe | Ala | Asn | Ser | Ile | Ile | Lys | Ser | Gly | Gly | Leu | Gly |
| | | 275 | | | | | 280 | | | | | 285 | | | |
| Tyr | Lys | Trp | Ser | Glu | Val | Ser | Phe | Lys | Pro | Ala | Phe | Tyr | Gln | Tyr | Thr |
| | 290 | | | | | 295 | | | | | 300 | | | | |
| Tyr | Thr | Arg | Asp | Gly | Glu | Glu | Val | Thr | Ala | His | Thr | Thr | Cys | Ser | Val |
| 305 | | | | | 310 | | | | | 315 | | | | | 320 |
| Asn | Gly | Val | Asn | Asp | Phe | Asn | Tyr | Asn | Gly | Gly | Ser | Leu | Pro | Thr | Asp |
| | | | | 325 | | | | | 330 | | | | | 335 | |
| Phe | Val | Ile | Ser | Lys | Tyr | Glu | Val | Ile | Lys | Glu | Asn | Ser | Phe | Val | Tyr |
| | | | 340 | | | | | 345 | | | | | 350 | | |
| Ile | Asp | Tyr | Trp | Asp | Asp | Ser | Gln | Ala | Phe | Arg | Asn | Met | Val | Tyr | Val |
| | | 355 | | | | | 360 | | | | | 365 | | | |
| Arg | Ser | Leu | Ala | Ala | Asp | Leu | Asn | Ser | Val | Met | Cys | Thr | Gly | Gly | Asp |
| | 370 | | | | | 375 | | | | | 380 | | | | |
| Tyr | Ser | Phe | Ala | Leu | Pro | Val | Gly | Asn | Tyr | Pro | Val | Met | Thr | Gly | Gly |
| 385 | | | | | 390 | | | | | 395 | | | | | 400 |
| Ala | Val | Ser | Leu | His | Ser | Ala | Gly | Val | Thr | Leu | Ser | Thr | Gln | Phe | Thr |
| | | | | 405 | | | | | 410 | | | | | 415 | |

-continued

```
Asp Phe Val Ser Leu Asn Ser Leu Arg Phe Arg Phe Arg Leu Ser Val
            420                 425                 430

Glu Glu Pro Pro Phe Ser Ile Leu Arg Thr Arg Val Ser Gly Leu Tyr
            435                 440                 445

Gly Leu Pro Ala Ala Lys Pro Asn Asn Ser Gln Glu Tyr Tyr Glu Ile
    450                 455                 460

Ala Gly Arg Phe Ser Leu Ile Ser Leu Val Pro Leu Asn Asp Asp Tyr
465                     470                 475                 480

Gln Thr Pro Ile Met Asn Ser Val Thr Val Arg Gln Asp Leu Glu Arg
                485                 490                 495

Gln Leu Gly Glu Leu Arg Asp Glu Phe Asn Asn Leu Ser Gln Gln Ile
            500                 505                 510

Ala Met Ser Gln Leu Ile Asp Leu Ala Leu Leu Pro Leu Asp Met Phe
        515                 520                 525

Ser Met Phe Ser Gly Ile Lys Ser Thr Ile Asp Ala Ala Lys Ser Met
    530                 535                 540

Ala Thr Asn Val Met Lys Arg Phe Lys Lys Ser Ser Leu Ala Asn Ser
545                 550                 555                 560

Val Ser Thr Leu Thr Asp Ser Leu Ser Asp Ala Ala Ser Ser Ile Ser
                565                 570                 575

Arg Ser Ala Ser Val Arg Ser Val Ser Ser Thr Ala Ser Ala Trp Thr
            580                 585                 590

Glu Val Ser Asn Ile Ala Ser Asp Ile Asn Val Thr Thr Ser Ser Ile
        595                 600                 605

Ser Thr Gln Thr Ser Thr Ile Ser Arg Arg Leu Arg Leu Lys Glu Met
    610                 615                 620

Ala Thr Gln Thr Asp Gly Met Asn Phe Asp Asp Ile Ser Ala Ala Val
625                 630                 635                 640

Leu Lys Thr Lys Ile Asp Lys Ser Thr Gln Leu Asn Thr Asn Thr Leu
                645                 650                 655

Pro Glu Ile Val Thr Glu Ala Ser Glu Lys Phe Ile Pro Asn Arg Ala
            660                 665                 670

Tyr Arg Val Ile Lys Asp Asp Glu Val Leu Glu Ala Ser Ile Asp Gly
        675                 680                 685

Lys Tyr Phe Ala Tyr Lys Val Glu Thr Phe Glu Glu Ile Pro Phe Asp
    690                 695                 700

Val Gln Lys Phe Ala Asp Leu Val Thr Asp Ser Pro Val Ile Ser Ala
705                 710                 715                 720

Ile Ile Asp Phe Lys Thr Leu Lys Asn Leu Asn Asp Asn Tyr Gly Ile
                725                 730                 735

Ser Arg Gln Gln Ala Leu Asn Leu Leu Arg Ser Asp Pro Arg Val Leu
            740                 745                 750

Arg Glu Phe Ile Asn Gln Asp Asn Pro Ile Ile Arg Asn Arg Ile Glu
        755                 760                 765

Ser Leu Ile Met Gln Cys Arg Leu
    770                 775
```

( 2 ) INFORMATION FOR SEQ ID NO:18:

( i ) SEQUENCE CHARACTERISTICS:
        ( A ) LENGTH: 776 amino acids
        ( B ) TYPE: amino acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:18:

-continued

| | | | | | | | | | | | | | | |
|---|---|---|---|---|---|---|---|---|---|---|---|---|---|---|
| Met 1 | Ala | Ser | Leu | Ile 5 | Tyr | Arg | Gln | Leu | Leu 10 | Thr | Asn | Ser | Tyr | Thr Val 15 |
| Asp | Leu | Ser | Asp 20 | Glu | Ile | Gln | Glu | Ile 25 | Gly | Ser | Thr | Lys 30 | Thr | Gln Asn |
| Val | Thr | Ile 35 | Asn | Leu | Gly | Pro | Phe 40 | Ala | Gln | Thr | Gly | Tyr 45 | Ala | Pro Val |
| Asn | Trp 50 | Gly | Pro | Gly | Glu | Thr 55 | Asn | Asp | Ser | Thr | Thr 60 | Val | Glu | Pro Val |
| Leu 65 | Asp | Gly | Pro | Tyr 70 | Gln | Pro | Thr | Ser | Phe 75 | Asn | Pro | Pro | Val | Asp Tyr 80 |
| Trp | Met | Leu | Leu | Ala 85 | Pro | Thr | Ala | Ala | Gly 90 | Val | Val | Val | Glu | Gly Thr 95 |
| Asn | Asn | Thr | Asp 100 | Arg | Trp | Leu | Ala | Thr 105 | Ile | Leu | Val | Glu 110 | Pro | Asn Val |
| Thr | Ser | Glu 115 | Thr | Arg | Ser | Tyr | Thr 120 | Leu | Phe | Gly | Thr | Gln 125 | Glu | Gln Ile |
| Thr | Ile 130 | Ala | Tyr | Ala | Ser | Gln 135 | Thr | Gln | Trp | Lys | Phe 140 | Ile | Asp | Val Val |
| Lys 145 | Thr | Thr | Gln | Asn | Gly 150 | Ser | Tyr | Ser | Gln | Tyr 155 | Gly | Pro | Leu | Gln Ser 160 |
| Thr | Pro | Lys | Leu | Tyr 165 | Ala | Val | Met | Lys | His 170 | Asn | Gly | Lys | Ile | Tyr Thr 175 |
| Tyr | Asn | Gly | Glu 180 | Thr | Pro | Asn | Val | Thr 185 | Thr | Lys | Tyr | Tyr 190 | Ser | Thr Thr |
| Asn | Tyr | Asp 195 | Ser | Val | Asn | Met | Thr 200 | Ala | Phe | Cys | Asp | Phe 205 | Tyr | Ile Ile |
| Pro | Arg 210 | Glu | Glu | Glu | Ser | Thr 215 | Cys | Thr | Glu | Tyr | Ile 220 | Asn | Asn | Gly Leu |
| Pro 225 | Pro | Ile | Gln | Asn | Thr 230 | Arg | Asn | Ile | Val | Pro 235 | Leu | Ala | Leu | Ser Ala 240 |
| Arg | Asn | Ile | Ile | Ser 245 | His | Arg | Ala | Gln | Ala 250 | Asn | Glu | Asp | Ile | Val Val 255 |
| Ser | Lys | Thr | Ser 260 | Leu | Trp | Lys | Glu | Met 265 | Gln | Tyr | Asn | Arg 270 | Asp | Ile Thr |
| Ile | Arg | Phe 275 | Lys | Phe | Ala | Ser | Ser 280 | Ile | Val | Lys | Ser | Gly 285 | Gly | Leu Gly |
| Tyr | Lys 290 | Trp | Ser | Glu | Ile | Ser 295 | Phe | Lys | Pro | Ala | Asn 300 | Tyr | Gln | Tyr Thr |
| Tyr 305 | Thr | Arg | Asp | Gly | Glu 310 | Asp | Val | Thr | Ala | His 315 | Thr | Thr | Cys | Ser Val 320 |
| Asn | Gly | Met | Asn | Asp 325 | Phe | Asn | Phe | Asn | Gly 330 | Gly | Ser | Leu | Pro | Thr Asp 335 |
| Phe | Ile | Ile | Ser 340 | Arg | Tyr | Glu | Val | Ile 345 | Lys | Glu | Asn | Ser | Tyr 350 | Val Tyr |
| Val | Asp | Tyr 355 | Trp | Asp | Asp | Ser | Gln 360 | Ala | Phe | Arg | Asn | Met 365 | Val | Tyr Val |
| Arg | Ser 370 | Leu | Ala | Ala | Asn | Leu 375 | Asn | Ser | Val | Ile | Cys 380 | Thr | Gly | Gly Asp |
| Tyr 385 | Ser | Phe | Ala | Leu | Pro 390 | Val | Gly | Gln | Trp | Pro 395 | Val | Met | Thr | Gly Gly 400 |
| Ala | Val | Ser | Leu | His 405 | Ser | Ala | Gly | Val | Thr 410 | Leu | Ser | Thr | Gln | Phe Thr 415 |
| Asp | Phe | Val | Ser 420 | Phe | Asn | Ser | Leu | Arg 425 | Phe | Arg | Phe | Arg 430 | Leu | Thr Val |
| Glu | Glu | Pro | Ser | Phe | Ser | Ile | Thr | Arg | Thr | Arg | Val | Gly | Gly | Leu Tyr |

|     |     |     |     |     | 435 |     |     |     |     | 440 |     |     |     |     | 445 |     |
| --- | --- | --- | --- | --- | --- | --- | --- | --- | --- | --- | --- | --- | --- | --- | --- | --- |
| Gly | Leu | Pro | Ala | Ala | Tyr | Pro | Asn | Asn | Gly | Lys | Glu | Tyr | Tyr | Glu | Val |
|     | 450 |     |     |     |     | 455 |     |     |     |     | 460 |     |     |     |     |
| Ala | Gly | Arg | Leu | Ser | Leu | Ile | Ser | Leu | Val | Pro | Ser | Asn | Asp | Asp | Tyr |
| 465 |     |     |     |     | 470 |     |     |     |     | 475 |     |     |     |     | 480 |
| Gln | Thr | Pro | Ile | Thr | Asn | Ser | Val | Thr | Val | Arg | Gln | Asp | Leu | Glu | Arg |
|     |     |     |     | 485 |     |     |     |     | 490 |     |     |     |     | 495 |     |
| Gln | Leu | Gly | Glu | Leu | Arg | Glu | Glu | Phe | Asn | Ala | Leu | Ser | Gln | Glu | Ile |
|     |     |     | 500 |     |     |     |     | 505 |     |     |     |     | 510 |     |     |
| Ala | Met | Ser | Gln | Leu | Ile | Tyr | Leu | Ala | Leu | Leu | Pro | Leu | Asp | Met | Phe |
|     |     | 515 |     |     |     |     | 520 |     |     |     |     | 525 |     |     |     |
| Ser | Met | Phe | Ser | Gly | Ile | Lys | Ser | Thr | Ile | Asp | Ala | Ala | Lys | Ser | Met |
|     | 530 |     |     |     |     | 535 |     |     |     |     | 540 |     |     |     |     |
| Ala | Thr | Ser | Val | Met | Lys | Lys | Phe | Lys | Lys | Ser | Gly | Leu | Ala | Asn | Ser |
| 545 |     |     |     |     | 550 |     |     |     |     | 555 |     |     |     |     | 560 |
| Val | Ser | Thr | Leu | Thr | Asp | Ser | Leu | Ser | Asp | Ala | Ala | Ser | Ser | Ile | Ser |
|     |     |     |     | 565 |     |     |     |     | 570 |     |     |     |     | 575 |     |
| Arg | Gly | Ala | Ser | Ile | Arg | Ser | Val | Gly | Ser | Ser | Ala | Ser | Ala | Trp | Thr |
|     |     |     | 580 |     |     |     |     | 585 |     |     |     |     | 590 |     |     |
| Asp | Val | Ser | Thr | Gln | Ile | Thr | Asp | Val | Ser | Ser | Ser | Val | Ser | Ser | Ile |
|     |     | 595 |     |     |     |     | 600 |     |     |     |     | 605 |     |     |     |
| Ser | Thr | Gln | Thr | Ser | Thr | Ile | Ser | Arg | Arg | Leu | Arg | Leu | Lys | Glu | Met |
|     | 610 |     |     |     |     | 615 |     |     |     |     | 620 |     |     |     |     |
| Ala | Thr | Gln | Thr | Glu | Gly | Met | Asn | Phe | Asp | Asp | Ile | Ser | Ala | Ala | Val |
| 625 |     |     |     |     | 630 |     |     |     |     | 635 |     |     |     |     | 640 |
| Leu | Lys | Thr | Lys | Ile | Asp | Arg | Ser | Thr | Gln | Ile | Ser | Pro | Asn | Thr | Leu |
|     |     |     |     | 645 |     |     |     |     | 650 |     |     |     |     | 655 |     |
| Pro | Asp | Ile | Val | Thr | Glu | Ala | Ser | Glu | Lys | Phe | Ile | Pro | Asn | Arg | Ala |
|     |     |     | 660 |     |     |     |     | 665 |     |     |     |     | 670 |     |     |
| Tyr | Arg | Val | Ile | Asn | Asn | Asp | Glu | Val | Phe | Glu | Ala | Gly | Thr | Asp | Gly |
|     |     | 675 |     |     |     |     | 680 |     |     |     |     | 685 |     |     |     |
| Arg | Tyr | Phe | Ala | Tyr | Arg | Val | Glu | Thr | Phe | Asp | Glu | Ile | Pro | Phe | Asp |
|     | 690 |     |     |     |     | 695 |     |     |     |     | 700 |     |     |     |     |
| Val | Gln | Lys | Phe | Ala | Asp | Leu | Val | Thr | Asp | Ser | Pro | Val | Ile | Ser | Ala |
| 705 |     |     |     |     | 710 |     |     |     |     | 715 |     |     |     |     | 720 |
| Ile | Ile | Asp | Phe | Lys | Thr | Leu | Lys | Asn | Leu | Asn | Asp | Asn | Tyr | Gly | Ile |
|     |     |     |     | 725 |     |     |     |     | 730 |     |     |     |     | 735 |     |
| Ser | Arg | Gln | Gln | Ala | Phe | Asn | Leu | Leu | Arg | Ser | Asp | Pro | Arg | Val | Leu |
|     |     |     | 740 |     |     |     |     | 745 |     |     |     |     | 750 |     |     |
| Arg | Glu | Phe | Ile | Asn | Gln | Asp | Asn | Pro | Ile | Ile | Arg | Asn | Arg | Ile | Glu |
|     |     | 755 |     |     |     |     | 760 |     |     |     |     | 765 |     |     |     |
| Gln | Leu | Ile | Met | Gln | Cys | Arg | Leu |     |     |     |     |     |     |     |     |
|     | 770 |     |     |     |     | 775 |     |     |     |     |     |     |     |     |     |

( 2 ) INFORMATION FOR SEQ ID NO:19:

( i ) SEQUENCE CHARACTERISTICS:
        ( A ) LENGTH: 2363 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 10..2337

( x i ) SEQUENCE DESCRIPTION: SEQ ID NO:19:

-continued

| | | | | | | | | | | | | | | | | |
|---|---|---|---|---|---|---|---|---|---|---|---|---|---|---|---|---|
| GGCTATAAA | ATG | GCT | TCA | CTC | ATT | TAT | AGA | CAG | TTG | CTT | ACT | AAT | TCA | | | 48 |
| | Met | Ala | Ser | Leu | Ile | Tyr | Arg | Gln | Leu | Leu | Thr | Asn | Ser | | | |
| | 1 | | | | 5 | | | | | 10 | | | | | | |
| TAC | ACA | GTA | GAA | CTT | TCA | GAT | GAA | ATC | CAA | GAA | ATT | GGA | TCG | ACT | AAG | 96 |
| Tyr | Thr | Val | Glu | Leu | Ser | Asp | Glu | Ile | Gln | Glu | Ile | Gly | Ser | Thr | Lys | |
| | 15 | | | | | 20 | | | | | 25 | | | | | |
| ACT | CAA | AAC | GTT | ACC | GTT | AAT | CCA | GGA | CCG | TTC | GCG | CAA | ACA | AAT | TAC | 144 |
| Thr | Gln | Asn | Val | Thr | Val | Asn | Pro | Gly | Pro | Phe | Ala | Gln | Thr | Asn | Tyr | |
| 30 | | | | | 35 | | | | | 40 | | | | | 45 | |
| GCT | TCA | GTT | AAT | TGG | GGA | CCT | GGT | GAA | ACG | AAT | GAC | TCA | ACT | ACA | GTT | 192 |
| Ala | Ser | Val | Asn | Trp | Gly | Pro | Gly | Glu | Thr | Asn | Asp | Ser | Thr | Thr | Val | |
| | | | | 50 | | | | | 55 | | | | | 60 | | |
| GAA | CCA | GTG | CTT | GAT | GGA | CCA | TAT | CAA | CCA | ACG | ACT | TTT | AAT | CCA | CCT | 240 |
| Glu | Pro | Val | Leu | Asp | Gly | Pro | Tyr | Gln | Pro | Thr | Thr | Phe | Asn | Pro | Pro | |
| | | | 65 | | | | | 70 | | | | | 75 | | | |
| GTA | AGT | TAT | TGG | ATG | TTG | TTA | GCA | CCA | ACG | AAC | GCG | GGG | GTG | GTA | GAT | 288 |
| Val | Ser | Tyr | Trp | Met | Leu | Leu | Ala | Pro | Thr | Asn | Ala | Gly | Val | Val | Asp | |
| | | 80 | | | | | 85 | | | | | 90 | | | | |
| CAA | GGT | ACG | AAC | AAT | ACA | AAC | AGA | TGG | TTA | GCG | ACA | ATA | TTA | ATT | AAA | 336 |
| Gln | Gly | Thr | Asn | Asn | Thr | Asn | Arg | Trp | Leu | Ala | Thr | Ile | Leu | Ile | Lys | |
| | 95 | | | | | 100 | | | | | 105 | | | | | |
| CCA | AAT | GTA | CAG | CAA | GTT | GAG | CGA | ACA | TAT | ACA | TTA | TTT | GGG | CAA | CAA | 384 |
| Pro | Asn | Val | Gln | Gln | Val | Glu | Arg | Thr | Tyr | Thr | Leu | Phe | Gly | Gln | Gln | |
| 110 | | | | | 115 | | | | | 120 | | | | | 125 | |
| GTT | CAA | GTA | ACA | GTA | TCA | AAT | GAT | TCA | CAG | ACA | AAG | TGG | AAG | TTT | GTG | 432 |
| Val | Gln | Val | Thr | Val | Ser | Asn | Asp | Ser | Gln | Thr | Lys | Trp | Lys | Phe | Val | |
| | | | | 130 | | | | | 135 | | | | | 140 | | |
| GAT | CTA | AGT | AAG | CAG | ACA | CAA | GAT | GGT | AAT | TAT | TCA | CAA | CAC | GGT | CCT | 480 |
| Asp | Leu | Ser | Lys | Gln | Thr | Gln | Asp | Gly | Asn | Tyr | Ser | Gln | His | Gly | Pro | |
| | | | 145 | | | | | 150 | | | | | 155 | | | |
| CTA | CTG | TCA | ACA | CCG | AAA | CTG | TAT | GGA | GTG | ATG | AAA | CAT | GGA | GGT | AAA | 528 |
| Leu | Leu | Ser | Thr | Pro | Lys | Leu | Tyr | Gly | Val | Met | Lys | His | Gly | Gly | Lys | |
| | | 160 | | | | | 165 | | | | | 170 | | | | |
| ATT | TAC | ACT | TAT | AAT | GGA | GAG | ACA | CCG | AAC | GCA | ACT | ACT | GGT | TAC | TAC | 576 |
| Ile | Tyr | Thr | Tyr | Asn | Gly | Glu | Thr | Pro | Asn | Ala | Thr | Thr | Gly | Tyr | Tyr | |
| | 175 | | | | | 180 | | | | | 185 | | | | | |
| TCT | ACA | ACT | AAC | TTT | GAC | ACT | GTA | AAC | ATG | ACA | GCA | TAT | TGT | GAT | TTT | 624 |
| Ser | Thr | Thr | Asn | Phe | Asp | Thr | Val | Asn | Met | Thr | Ala | Tyr | Cys | Asp | Phe | |
| 190 | | | | | 195 | | | | | 200 | | | | | 205 | |
| TAT | ATA | ATT | CCA | TTA | GCA | CAA | GAA | GCA | AAA | TGC | ACT | GAA | TAC | ATA | AAT | 672 |
| Tyr | Ile | Ile | Pro | Leu | Ala | Gln | Glu | Ala | Lys | Cys | Thr | Glu | Tyr | Ile | Asn | |
| | | | | 210 | | | | | 215 | | | | | 220 | | |
| AAT | GGA | TTA | CCA | CCA | ATA | CAA | AAT | ACG | AGA | AAT | ATC | GTA | CCA | GTT | TCG | 720 |
| Asn | Gly | Leu | Pro | Pro | Ile | Gln | Asn | Thr | Arg | Asn | Ile | Val | Pro | Val | Ser | |
| | | | 225 | | | | | 230 | | | | | 235 | | | |
| ATA | GTA | TCA | AGG | AAT | ATT | GTA | TAT | ACA | AGA | GCA | CAA | CCT | AAT | CAA | GAC | 768 |
| Ile | Val | Ser | Arg | Asn | Ile | Val | Tyr | Thr | Arg | Ala | Gln | Pro | Asn | Gln | Asp | |
| | | 240 | | | | | 245 | | | | | 250 | | | | |
| ATA | GTG | GTA | TCA | AAA | ACT | TCA | TTA | TGG | AAA | GAG | ATG | CAA | TAT | AAT | AGA | 816 |
| Ile | Val | Val | Ser | Lys | Thr | Ser | Leu | Trp | Lys | Glu | Met | Gln | Tyr | Asn | Arg | |
| | 255 | | | | | 260 | | | | | 265 | | | | | |
| GAT | ATA | GTG | ATA | AGA | TTT | AAA | TTT | GCT | AAC | TCA | ATC | ATA | AAA | TCA | GGG | 864 |
| Asp | Ile | Val | Ile | Arg | Phe | Lys | Phe | Ala | Asn | Ser | Ile | Ile | Lys | Ser | Gly | |
| 270 | | | | | 275 | | | | | 280 | | | | | 285 | |
| GGA | TTG | GGA | TAT | AAA | TGG | TCA | GAA | GTG | TCA | TTT | AAA | CCA | GCT | AAT | TAT | 912 |
| Gly | Leu | Gly | Tyr | Lys | Trp | Ser | Glu | Val | Ser | Phe | Lys | Pro | Ala | Asn | Tyr | |
| | | | | 290 | | | | | 295 | | | | | 300 | | |
| CAG | TAC | ACA | TAT | ACC | AGA | GAT | GGT | GAA | GAA | GTT | ACT | GCA | CAT | ACT | ACG | 960 |
| Gln | Tyr | Thr | Tyr | Thr | Arg | Asp | Gly | Glu | Glu | Val | Thr | Ala | His | Thr | Thr | |
| | | | 305 | | | | | 310 | | | | | 315 | | | |
| TGT | TCA | GTA | AAT | GGA | ATA | AAT | GAT | TTT | AAT | TAT | AAT | GGT | GGA | TCA | TTA | 1008 |

-continued

| | | | | | | | | | | | | | | | | |
|---|---|---|---|---|---|---|---|---|---|---|---|---|---|---|---|---|
| Cys | Ser | Val | Asn | Gly | Ile | Asn | Asp | Phe | Asn | Tyr | Asn | Gly | Gly | Ser | Leu | |
| | | 320 | | | | 325 | | | | | 330 | | | | | |

| CCG | ACT | GAT | TTC | GTA | ATA | TCA | AAA | TAT | GAA | GTG | ATT | AAG | GAA | AAT | TCT | 1056 |
| Pro | Thr | Asp | Phe | Val | Ile | Ser | Lys | Tyr | Glu | Val | Ile | Lys | Glu | Asn | Ser | |
| | 335 | | | | | 340 | | | | | 345 | | | | | |

| TTT | GTG | TAT | ATA | GAC | TAC | TGG | GAC | GAT | TCA | CAA | GCA | TTT | AGA | AAC | ATG | 1104 |
| Phe | Val | Tyr | Ile | Asp | Tyr | Trp | Asp | Asp | Ser | Gln | Ala | Phe | Arg | Asn | Met | |
| 350 | | | | | 355 | | | | | 360 | | | | | 365 | |

| GTA | TAT | GTA | CGC | TCG | TTG | GCA | GCC | GAT | TTA | AAT | TCG | GTA | ATG | TGT | ACA | 1152 |
| Val | Tyr | Val | Arg | Ser | Leu | Ala | Ala | Asp | Leu | Asn | Ser | Val | Met | Cys | Thr | |
| | | | | 370 | | | | | 375 | | | | | 380 | | |

| GGA | GGT | GAC | TAT | AGT | TTT | GCG | ATT | CCA | GTT | GGT | AAT | TAT | CCA | GTT | ATG | 1200 |
| Gly | Gly | Asp | Tyr | Ser | Phe | Ala | Ile | Pro | Val | Gly | Asn | Tyr | Pro | Val | Met | |
| | | | 385 | | | | | 390 | | | | | 395 | | | |

| ACT | GGG | GGT | GCT | GTG | TCA | TTG | CAT | TCA | GCA | GGT | GTA | ACT | TTA | TCA | ACG | 1248 |
| Thr | Gly | Gly | Ala | Val | Ser | Leu | His | Ser | Ala | Gly | Val | Thr | Leu | Ser | Thr | |
| | | 400 | | | | | 405 | | | | | 410 | | | | |

| CAG | TTT | ACA | GAT | TTC | GTA | TCA | TTA | AAT | TCA | CTG | AGA | TTT | AGA | TTT | AGA | 1296 |
| Gln | Phe | Thr | Asp | Phe | Val | Ser | Leu | Asn | Ser | Leu | Arg | Phe | Arg | Phe | Arg | |
| | 415 | | | | | 420 | | | | | 425 | | | | | |

| TTA | TCA | GTA | GAA | GAA | CCG | CCG | TTC | TCA | ATT | CTA | CGG | ACC | AGA | GTT | AGT | 1344 |
| Leu | Ser | Val | Glu | Glu | Pro | Pro | Phe | Ser | Ile | Leu | Arg | Thr | Arg | Val | Ser | |
| 430 | | | | | 435 | | | | | 440 | | | | | 445 | |

| GGA | TTG | TAT | GGA | CTT | CCA | GCG | GCA | AAA | CCG | AAT | AAT | TCA | CAA | GAA | TAT | 1392 |
| Gly | Leu | Tyr | Gly | Leu | Pro | Ala | Ala | Lys | Pro | Asn | Asn | Ser | Gln | Glu | Tyr | |
| | | | | 450 | | | | | 455 | | | | | 460 | | |

| TAT | GAG | ATA | GCT | GGG | AGA | TTT | TCA | TTA | ATA | TCA | CTC | GTA | CCG | TCA | AAT | 1440 |
| Tyr | Glu | Ile | Ala | Gly | Arg | Phe | Ser | Leu | Ile | Ser | Leu | Val | Pro | Ser | Asn | |
| | | | 465 | | | | | 470 | | | | | 475 | | | |

| GAT | GAT | TAT | CAG | ACA | CCA | ATA | ATA | AAT | TCA | GTC | ACT | GTA | CGA | CAA | GAT | 1488 |
| Asp | Asp | Tyr | Gln | Thr | Pro | Ile | Ile | Asn | Ser | Val | Thr | Val | Arg | Gln | Asp | |
| | | 480 | | | | | 485 | | | | | 490 | | | | |

| TTA | GAA | CGA | CAA | TTA | GGA | GAA | CTA | AGA | GAT | GAA | TTT | AAC | AAT | TTA | TCA | 1536 |
| Leu | Glu | Arg | Gln | Leu | Gly | Glu | Leu | Arg | Asp | Glu | Phe | Asn | Asn | Leu | Ser | |
| | 495 | | | | | 500 | | | | | 505 | | | | | |

| CAA | CAA | ATC | GCT | ATG | TCA | CAA | CTG | ATA | GAT | CTT | GCG | TTA | CTA | CCG | TTA | 1584 |
| Gln | Gln | Ile | Ala | Met | Ser | Gln | Leu | Ile | Asp | Leu | Ala | Leu | Leu | Pro | Leu | |
| 510 | | | | | 515 | | | | | 520 | | | | | 525 | |

| GAC | ATG | TTC | TCA | ATG | TTT | TCA | GGG | ATT | AAG | AGT | ACA | ATT | GAC | GCA | GCG | 1632 |
| Asp | Met | Phe | Ser | Met | Phe | Ser | Gly | Ile | Lys | Ser | Thr | Ile | Asp | Ala | Ala | |
| | | | | 530 | | | | | 535 | | | | | 540 | | |

| AAG | TCT | ATG | GCG | ACG | AAT | GTA | ATG | AAG | AGA | TTT | AAA | AAG | TCA | AGT | CTC | 1680 |
| Lys | Ser | Met | Ala | Thr | Asn | Val | Met | Lys | Arg | Phe | Lys | Lys | Ser | Ser | Leu | |
| | | | 545 | | | | | 550 | | | | | 555 | | | |

| GCT | AAC | TCA | GTG | TCA | ACG | CTC | ACT | GAT | TCA | TTG | TCT | GAT | GCA | GCA | TCA | 1728 |
| Ala | Asn | Ser | Val | Ser | Thr | Leu | Thr | Asp | Ser | Leu | Ser | Asp | Ala | Ala | Ser | |
| | | 560 | | | | | 565 | | | | | 570 | | | | |

| TCA | ATT | TCT | AGA | AGT | GCA | TCG | GTT | AGA | TCA | GTT | AGT | TCA | ACT | GCA | TCA | 1776 |
| Ser | Ile | Ser | Arg | Ser | Ala | Ser | Val | Arg | Ser | Val | Ser | Ser | Thr | Ala | Ser | |
| | 575 | | | | | 580 | | | | | 585 | | | | | |

| GCT | TGG | ACG | GAA | GTA | TCT | AAC | ATT | ACA | TCA | GAT | ATT | AAT | GTG | ACA | ACG | 1824 |
| Ala | Trp | Thr | Glu | Val | Ser | Asn | Ile | Thr | Ser | Asp | Ile | Asn | Val | Thr | Thr | |
| 590 | | | | | 595 | | | | | 600 | | | | | 605 | |

| AGC | TCG | ATC | TCT | ACA | CAG | ACA | TCA | ACA | ATA | AGC | AGA | AGG | TTA | AGA | CTA | 1872 |
| Ser | Ser | Ile | Ser | Thr | Gln | Thr | Ser | Thr | Ile | Ser | Arg | Arg | Leu | Arg | Leu | |
| | | | | 610 | | | | | 615 | | | | | 620 | | |

| AAA | GAA | ATG | GCG | ACT | CAA | ACG | GAC | GGT | ATG | AAT | TTT | GAT | GAT | ATA | TCA | 1920 |
| Lys | Glu | Met | Ala | Thr | Gln | Thr | Asp | Gly | Met | Asn | Phe | Asp | Asp | Ile | Ser | |
| | | | 625 | | | | | 630 | | | | | 635 | | | |

| GCA | GCA | GTA | CTC | AAG | ACT | AAA | ATT | GAT | AAA | TCA | ACC | CAG | TTA | AAT | ACA | 1968 |
| Ala | Ala | Val | Leu | Lys | Thr | Lys | Ile | Asp | Lys | Ser | Thr | Gln | Leu | Asn | Thr | |
| | | 640 | | | | | 645 | | | | | 650 | | | | |

| | | | | | | | | | | | | | | | | |
|---|---|---|---|---|---|---|---|---|---|---|---|---|---|---|---|---|
|AAT|ACA|TTG|CCG|GAA|ATA|GTA|ACT|GAG|GCT|TCA|GAA|AAG|TTT|ATA|CCA|2016|
|Asn|Thr|Leu|Pro|Glu|Ile|Val|Thr|Glu|Ala|Ser|Glu|Lys|Phe|Ile|Pro| |
| |655| | | |660| | | |665| | | | | | | |
|AAT|AGA|GCG|TAC|CGT|GTA|ATT|AAA|GAT|GAT|GAA|GTG|CTA|GAG|GCT|AGT|2064|
|Asn|Arg|Ala|Tyr|Arg|Val|Ile|Lys|Asp|Asp|Glu|Val|Leu|Glu|Ala|Ser| |
|670| | | |675| | | |680| | | | | | |685| |
|ACT|GAT|GGT|AAA|TAT|TTC|GCT|TAC|AAA|GTT|GAA|ACC|ATT|TTG|AAG|AGA|2112|
|Thr|Asp|Gly|Lys|Tyr|Phe|Ala|Tyr|Lys|Val|Glu|Thr|Ile|Leu|Lys|Arg| |
| | | | |690| | | |695| | | |700| | | | |
|TTC|CAT|TCG|ATG|TAC|AAA|TTC|GCT|GAC|TTA|GTG|ACT|GAC|TCA|CCA|GTT|2160|
|Phe|His|Ser|Met|Tyr|Lys|Phe|Ala|Asp|Leu|Val|Thr|Asp|Ser|Pro|Val| |
| | | |705| | | |710| | | | |715| | | | |
|ATA|TCG|GCA|ATA|ATT|GAC|TTT|AAA|ACT|CTT|AAG|AAT|CTA|AAT|GAT|AAT|2208|
|Ile|Ser|Ala|Ile|Ile|Asp|Phe|Lys|Thr|Leu|Lys|Asn|Leu|Asn|Asp|Asn| |
| | |720| | | |725| | | | |730| | | | | |
|TAC|GGA|ATA|AGC|AGA|CAA|CAA|GCA|CTA|AAT|CTT|CTA|AGA|TCT|GAT|CCG|2256|
|Tyr|Gly|Ile|Ser|Arg|Gln|Gln|Ala|Leu|Asn|Leu|Leu|Arg|Ser|Asp|Pro| |
| |735| | | |740| | | | |745| | | | | | |
|CGA|GTA|TTA|CGT|GAA|TTT|ATT|AAT|CAG|GAT|AAT|CCA|ATA|ATA|CGA|AAT|2304|
|Arg|Val|Leu|Arg|Glu|Phe|Ile|Asn|Gln|Asp|Asn|Pro|Ile|Ile|Arg|Asn| |
|750| | | | |755| | | |760| | | | | |765| |
|AGA|ATA|GAA|AGT|TTG|ATA|ATG|CAA|TGT|CGC|TTG|TAAGCAACTG|AACAAGAGGA| | | |2357|
|Arg|Ile|Glu|Ser|Leu|Ile|Met|Gln|Cys|Arg|Leu| | | | | | |
| | | | |770| | | |775| | | | | | | | |
|TGTGAC| | | | | | | | | | | | | | | |2363|

(2) INFORMATION FOR SEQ ID NO:20:

(i) SEQUENCE CHARACTERISTICS:
        (A) LENGTH: 776 amino acids
        (B) TYPE: amino acid
        (D) TOPOLOGY: linear (ii) MOLECULE TYPE: protein (xi) SEQUENCE DESCRIPTION: SEQ ID NO:20:

| | | | | | | | | | | | | | | |
|---|---|---|---|---|---|---|---|---|---|---|---|---|---|---|
|Met|Ala|Ser|Leu|Ile|Tyr|Arg|Gln|Leu|Leu|Thr|Asn|Ser|Tyr|Thr|Val|
|1| | | |5| | | | |10| | | | |15|
|Glu|Leu|Ser|Asp|Glu|Ile|Gln|Glu|Ile|Gly|Ser|Thr|Lys|Thr|Gln|Asn|
| | | |20| | | |25| | | | |30| | |
|Val|Thr|Val|Asn|Pro|Gly|Pro|Phe|Ala|Gln|Thr|Asn|Tyr|Ala|Ser|Val|
| | |35| | | |40| | | | |45| | | |
|Asn|Trp|Gly|Pro|Gly|Glu|Thr|Asn|Asp|Ser|Thr|Thr|Val|Glu|Pro|Val|
| |50| | | |55| | | | |60| | | | |
|Leu|Asp|Gly|Pro|Tyr|Gln|Pro|Thr|Thr|Phe|Asn|Pro|Pro|Val|Ser|Tyr|
|65| | | |70| | | |75| | | | |80|
|Trp|Met|Leu|Leu|Ala|Pro|Thr|Asn|Ala|Gly|Val|Val|Asp|Gln|Gly|Thr|
| | | |85| | | |90| | | | |95| |
|Asn|Asn|Thr|Asn|Arg|Trp|Leu|Ala|Thr|Ile|Leu|Ile|Lys|Pro|Asn|Val|
| | | |100| | | |105| | | | |110| | |
|Gln|Gln|Val|Glu|Arg|Thr|Tyr|Thr|Leu|Phe|Gly|Gln|Val|Gln|Val|
| | |115| | | |120| | | | |125| | |
|Thr|Val|Ser|Asn|Asp|Ser|Gln|Thr|Lys|Trp|Lys|Phe|Val|Asp|Leu|Ser|
| |130| | | |135| | | | |140| | | | |
|Lys|Gln|Thr|Gln|Asp|Gly|Asn|Tyr|Ser|Gln|His|Gly|Pro|Leu|Leu|Ser|
|145| | | |150| | | |155| | | | |160|
|Thr|Pro|Lys|Leu|Tyr|Gly|Val|Met|Lys|His|Gly|Gly|Lys|Ile|Tyr|Thr|
| | | |165| | | |170| | | | |175| |
|Tyr|Asn|Gly|Glu|Thr|Pro|Asn|Ala|Thr|Thr|Gly|Tyr|Tyr|Ser|Thr|Thr|
| | | |180| | | |185| | | | |190| |

-continued

```
Asn Phe Asp Thr Val Asn Met Thr Ala Tyr Cys Asp Phe Tyr Ile Ile
        195                 200                 205
Pro Leu Ala Gln Glu Ala Lys Cys Thr Glu Tyr Ile Asn Asn Gly Leu
    210                 215                 220
Pro Pro Ile Gln Asn Thr Arg Asn Ile Val Pro Val Ser Ile Val Ser
225                 230                 235                 240
Arg Asn Ile Val Tyr Thr Arg Ala Gln Pro Asn Gln Asp Ile Val Val
                245                 250                 255
Ser Lys Thr Ser Leu Trp Lys Glu Met Gln Tyr Asn Arg Asp Ile Val
            260                 265                 270
Ile Arg Phe Lys Phe Ala Asn Ser Ile Ile Lys Ser Gly Gly Leu Gly
        275                 280                 285
Tyr Lys Trp Ser Glu Val Ser Phe Lys Pro Ala Asn Tyr Gln Tyr Thr
    290                 295                 300
Tyr Thr Arg Asp Gly Glu Glu Val Thr Ala His Thr Thr Cys Ser Val
305                 310                 315                 320
Asn Gly Ile Asn Asp Phe Asn Tyr Asn Gly Gly Ser Leu Pro Thr Asp
                325                 330                 335
Phe Val Ile Ser Lys Tyr Glu Val Ile Lys Glu Asn Ser Phe Val Tyr
            340                 345                 350
Ile Asp Tyr Trp Asp Asp Ser Gln Ala Phe Arg Asn Met Val Tyr Val
        355                 360                 365
Arg Ser Leu Ala Ala Asp Leu Asn Ser Val Met Cys Thr Gly Gly Asp
    370                 375                 380
Tyr Ser Phe Ala Ile Pro Val Gly Asn Tyr Pro Val Met Thr Gly Gly
385                 390                 395                 400
Ala Val Ser Leu His Ser Ala Gly Val Thr Leu Ser Thr Gln Phe Thr
                405                 410                 415
Asp Phe Val Ser Leu Asn Ser Leu Arg Phe Arg Phe Arg Leu Ser Val
            420                 425                 430
Glu Glu Pro Pro Phe Ser Ile Leu Arg Thr Arg Val Ser Gly Leu Tyr
        435                 440                 445
Gly Leu Pro Ala Ala Lys Pro Asn Asn Ser Gln Glu Tyr Tyr Glu Ile
    450                 455                 460
Ala Gly Arg Phe Ser Leu Ile Ser Leu Val Pro Ser Asn Asp Asp Tyr
465                 470                 475                 480
Gln Thr Pro Ile Ile Asn Ser Val Thr Val Arg Gln Asp Leu Glu Arg
                485                 490                 495
Gln Leu Gly Glu Leu Arg Asp Glu Phe Asn Asn Leu Ser Gln Gln Ile
            500                 505                 510
Ala Met Ser Gln Leu Ile Asp Leu Ala Leu Leu Pro Leu Asp Met Phe
        515                 520                 525
Ser Met Phe Ser Gly Ile Lys Ser Thr Ile Asp Ala Ala Lys Ser Met
    530                 535                 540
Ala Thr Asn Val Met Lys Arg Phe Lys Lys Ser Ser Leu Ala Asn Ser
545                 550                 555                 560
Val Ser Thr Leu Thr Asp Ser Leu Ser Asp Ala Ala Ser Ser Ile Ser
                565                 570                 575
Arg Ser Ala Ser Val Arg Ser Val Ser Ser Thr Ala Ser Ala Trp Thr
            580                 585                 590
Glu Val Ser Asn Ile Thr Ser Asp Ile Asn Val Thr Thr Ser Ser Ile
        595                 600                 605
Ser Thr Gln Thr Ser Thr Ile Ser Arg Arg Leu Arg Leu Lys Glu Met
    610                 615                 620
```

| | | | | | | | | | | | | | | |
|---|---|---|---|---|---|---|---|---|---|---|---|---|---|---|
| Ala | Thr | Gln | Thr | Asp | Gly | Met | Asn | Phe | Asp | Asp | Ile | Ser | Ala | Ala | Val |
| 625 | | | | | 630 | | | | | 635 | | | | | 640 |
| Leu | Lys | Thr | Lys | Ile | Asp | Lys | Ser | Thr | Gln | Leu | Asn | Thr | Asn | Thr | Leu |
| | | | | 645 | | | | | 650 | | | | | 655 | |
| Pro | Glu | Ile | Val | Thr | Glu | Ala | Ser | Glu | Lys | Phe | Ile | Pro | Asn | Arg | Ala |
| | | | 660 | | | | | 665 | | | | | 670 | | |
| Tyr | Arg | Val | Ile | Lys | Asp | Asp | Glu | Val | Leu | Glu | Ala | Ser | Thr | Asp | Gly |
| | | 675 | | | | | 680 | | | | | 685 | | | |
| Lys | Tyr | Phe | Ala | Tyr | Lys | Val | Glu | Thr | Ile | Leu | Lys | Arg | Phe | His | Ser |
| | 690 | | | | | 695 | | | | | 700 | | | | |
| Met | Tyr | Lys | Phe | Ala | Asp | Leu | Val | Thr | Asp | Ser | Pro | Val | Ile | Ser | Ala |
| 705 | | | | | 710 | | | | | 715 | | | | | 720 |
| Ile | Ile | Asp | Phe | Lys | Thr | Leu | Lys | Asn | Leu | Asn | Asp | Asn | Tyr | Gly | Ile |
| | | | | 725 | | | | | 730 | | | | | 735 | |
| Ser | Arg | Gln | Gln | Ala | Leu | Asn | Leu | Leu | Arg | Ser | Asp | Pro | Arg | Val | Leu |
| | | | 740 | | | | | 745 | | | | | 750 | | |
| Arg | Glu | Phe | Ile | Asn | Gln | Asp | Asn | Pro | Ile | Ile | Arg | Asn | Arg | Ile | Glu |
| | | | 755 | | | | | 760 | | | | | 765 | | |
| Ser | Leu | Ile | Met | Gln | Cys | Arg | Leu | | | | | | | | |
| | 770 | | | | | 775 | | | | | | | | | |

(2) INFORMATION FOR SEQ ID NO:21:

(i) SEQUENCE CHARACTERISTICS:
        (A) LENGTH: 1062 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 49..1026

(xi) SEQUENCE DESCRIPTION: SEQ ID NO:21:

| | | | | | | | | | | | | | | | | |
|---|---|---|---|---|---|---|---|---|---|---|---|---|---|---|---|---|
| GGCTTTAAAA | GCGAGAATTT | CCGTTTGGCT | AGCGGTTAGC | TCCTTTTA | ATG | TAT | GGT | | | | | | | | | 57 |
| | | | | | Met | Tyr | Gly | | | | | | | | | |
| | | | | | 1 | | | | | | | | | | | |
| ATT | GAA | TAT | ACC | ACA | ATT | CTA | ATC | TTC | TTG | ACA | TCG | ATT | ACA | TTA | TTG | 105 |
| Ile | Glu | Tyr | Thr | Thr | Ile | Leu | Ile | Phe | Leu | Thr | Ser | Ile | Thr | Leu | Leu | |
| | 5 | | | | | 10 | | | | | 15 | | | | | |
| AAT | TAT | ATC | TTA | AAA | TCA | ATA | ACG | AGA | ATA | ATG | GAC | TAT | ATA | ATT | TAC | 153 |
| Asn | Tyr | Ile | Leu | Lys | Ser | Ile | Thr | Arg | Ile | Met | Asp | Tyr | Ile | Ile | Tyr | |
| 20 | | | | | 25 | | | | | 30 | | | | | 35 | |
| AGA | TTT | CTG | CTT | ATA | GTA | GTG | ATC | TTG | GCC | ACC | ATA | ATA | AAT | GCG | CAA | 201 |
| Arg | Phe | Leu | Leu | Ile | Val | Val | Ile | Leu | Ala | Thr | Ile | Ile | Asn | Ala | Gln | |
| | | | | 40 | | | | | 45 | | | | | 50 | | |
| AAC | TAT | GGA | GTA | AAT | TTG | CCA | ATT | ACA | GGT | TCA | ATG | GAT | ACT | GCG | TAT | 249 |
| Asn | Tyr | Gly | Val | Asn | Leu | Pro | Ile | Thr | Gly | Ser | Met | Asp | Thr | Ala | Tyr | |
| | | | 55 | | | | | 60 | | | | | 65 | | | |
| GCA | GAC | TCT | ACA | CAA | AGT | GAG | CCA | TTT | TTG | ACA | TCA | ACC | CTT | TGT | TTG | 297 |
| Ala | Asp | Ser | Thr | Gln | Ser | Glu | Pro | Phe | Leu | Thr | Ser | Thr | Leu | Cys | Leu | |
| | | 70 | | | | | 75 | | | | | 80 | | | | |
| TAT | TAT | CCT | GTT | GAG | GCA | TCA | AAC | GAA | ATA | GCT | GAT | ACC | GAA | TGG | AAA | 345 |
| Tyr | Tyr | Pro | Val | Glu | Ala | Ser | Asn | Glu | Ile | Ala | Asp | Thr | Glu | Trp | Lys | |
| | 85 | | | | | 90 | | | | | 95 | | | | | |
| GAT | ACC | TTA | TCA | CAA | TTG | TTC | TTG | ACA | AAA | GGA | TGG | CCA | ACA | GGA | TCA | 393 |
| Asp | Thr | Leu | Ser | Gln | Leu | Phe | Leu | Thr | Lys | Gly | Trp | Pro | Thr | Gly | Ser | |
| 100 | | | | | 105 | | | | | 110 | | | | | 115 | |
| GTG | TAC | CTT | AAA | GAA | TAT | GCT | GAT | ATA | GCG | GCC | TTT | TCA | GTG | GAA | CCA | 441 |
| Val | Tyr | Leu | Lys | Glu | Tyr | Ala | Asp | Ile | Ala | Ala | Phe | Ser | Val | Glu | Pro | |

-continued

|  |  |  | 120 |  |  |  |  | 125 |  |  |  |  | 130 |  |  |  |
|---|---|---|---|---|---|---|---|---|---|---|---|---|---|---|---|---|
| CAG | TTA | TAC | TGC | GAT | TAT | AAT | TTA | GTT | TTA | ATG | AAA | TAT | GAC | TCT | ACA | 489 |
| Gln | Leu | Tyr 135 | Cys | Asp | Tyr | Asn | Leu | Val 140 | Leu | Met | Lys | Tyr 145 | Asp | Ser | Thr |  |
| CAA | GAA | CTA | GAT | ATG | TCT | GAA | TTG | GCC | GAT | CTT | ATA | TTG | AAC | GAA | TGG | 537 |
| Gln | Glu | Leu 150 | Asp | Met | Ser | Glu | Leu | Ala 155 | Asp | Leu | Ile | Leu 160 | Asn | Glu | Trp |  |
| CTG | TGC | AAT | CCA | ATG | GAC | ATA | ACG | CTA | TAT | TAT | TAT | CAG | CAG | ACT | GAT | 585 |
| Leu | Cys | Asn 165 | Pro | Met | Asp | Ile | Thr | Leu 170 | Tyr | Tyr | Tyr | Gln 175 | Gln | Thr | Asp |  |
| GAA | GCA | AAT | AAA | TCG | ATA | TGG | ACG | GGC | TCT | TCT | TGC | ACG | GTT | AAA | GTG | 633 |
| Glu 180 | Ala | Asn | Lys | Ser | Ile 185 | Trp | Thr | Gly | Ser | Ser 190 | Cys | Thr | Val | Lys | Val 195 |  |
| TGT | CCA | TTA | AAT | ACA | CAA | ACA | CTT | GGT | ATT | GGA | TGT | CTA | ATA | ACT | AAT | 681 |
| Cys | Pro | Leu | Asn | Thr 200 | Gln | Thr | Leu | Gly | Ile 205 | Gly | Cys | Leu | Ile | Thr 210 | Asn |  |
| CCA | GAC | ACG | TTT | GAA | ACA | GTT | GCG | ACA | ATG | GAG | AAG | TTA | GTG | ATT | ACA | 729 |
| Pro | Asp | Thr | Phe 215 | Glu | Thr | Val | Ala | Thr | Met 220 | Glu | Lys | Leu | Val 225 | Ile | Thr |  |
| GAT | GTT | GTA | GAT | GGT | GTC | AAT | CAC | AAA | TTA | AAC | GTC | ACA | ACG | GCA | ACG | 777 |
| Asp | Val | Val 230 | Asp | Gly | Val | Asn | His 235 | Lys | Leu | Asn | Val | Thr 240 | Thr | Ala | Thr |  |
| TGC | ACC | ATA | CGC | AAC | TGT | AAA | AAG | TTA | GGA | CCA | AGG | GAG | AAC | GTA | GCA | 825 |
| Cys | Thr | Ile 245 | Arg | Asn | Cys | Lys | Lys 250 | Leu | Gly | Pro | Arg | Glu 255 | Asn | Val | Ala |  |
| GTC | ATA | CAG | GTA | GGC | GGC | GCG | AAC | ATT | TTA | GAC | ATC | ACA | GCT | GAT | CCA | 873 |
| Val 260 | Ile | Gln | Val | Gly | Gly 265 | Ala | Asn | Ile | Leu | Asp 270 | Ile | Thr | Ala | Asp | Pro 275 |  |
| ACA | ACT | ACA | CCA | CAG | ACA | GAG | ACA | ATG | ATG | CGA | ATA | AAT | TGG | AAA | AAA | 921 |
| Thr | Thr | Thr | Pro | Gln 280 | Thr | Glu | Thr | Met | Met 285 | Arg | Ile | Asn | Trp | Lys 290 | Lys |  |
| TGG | TGG | CAA | GTC | TTT | TAC | ACG | GTA | GTG | GAT | TAC | GTC | AAT | CAG | ATA | ATT | 969 |
| Trp | Trp | Gln | Val 295 | Phe | Tyr | Thr | Val | Val 300 | Asp | Tyr | Val | Asn | Gln 305 | Ile | Ile |  |
| CAG | ACA | ATG | TCC | AAA | AGA | TCT | ACA | TCG | CTT | AAT | TCG | TCG | GCG | TTC | TAC | 1017 |
| Gln | Thr | Met 310 | Ser | Lys | Arg | Ser | Thr 315 | Ser | Leu | Asn | Ser | Ser 320 | Ala | Phe | Tyr |  |
| TAT | AGA | GTG | TAGGTGCATG | CTAGATTAGA | GTTGTATGAT | GTGACC |  |  |  |  |  |  |  |  |  | 1062 |
| Tyr | Arg | Val 325 |  |  |  |  |  |  |  |  |  |  |  |  |  |  |

( 2 ) INFORMATION FOR SEQ ID NO:22:

( i ) SEQUENCE CHARACTERISTICS:
        ( A ) LENGTH: 326 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| Met 1 | Tyr | Gly | Ile | Glu 5 | Tyr | Thr | Thr | Ile | Leu 10 | Ile | Phe | Leu | Thr | Ser 15 | Ile |
|---|---|---|---|---|---|---|---|---|---|---|---|---|---|---|---|
| Thr | Leu | Leu | Asn 20 | Tyr | Ile | Leu | Lys | Ser 25 | Ile | Thr | Arg | Ile | Met 30 | Asp | Tyr |
| Ile | Ile | Tyr 35 | Arg | Phe | Leu | Leu | Ile 40 | Val | Val | Ile | Leu | Ala 45 | Thr | Ile | Ile |
| Asn | Ala 50 | Gln | Asn | Tyr | Gly | Val 55 | Asn | Leu | Pro | Ile | Thr 60 | Gly | Ser | Met | Asp |
| Thr 65 | Ala | Tyr | Ala | Asp | Ser 70 | Thr | Gln | Ser | Glu | Pro 75 | Phe | Leu | Thr | Ser | Thr 80 |
| Leu | Cys | Leu | Tyr | Tyr | Pro | Val | Glu | Ala | Ser | Asn | Glu | Ile | Ala | Asp | Thr |

|  | 85 | 90 | 95 |
|---|---|---|---|

Glu Trp Lys Asp Thr Leu Ser Gln Leu Phe Leu Thr Lys Gly Trp Pro
                100                     105                 110

Thr Gly Ser Val Tyr Leu Lys Glu Tyr Ala Asp Ile Ala Ala Phe Ser
            115                 120                 125

Val Glu Pro Gln Leu Tyr Cys Asp Tyr Asn Leu Val Leu Met Lys Tyr
    130                 135                 140

Asp Ser Thr Gln Glu Leu Asp Met Ser Glu Leu Ala Asp Leu Ile Leu
145                     150                 155                 160

Asn Glu Trp Leu Cys Asn Pro Met Asp Ile Thr Leu Tyr Tyr Tyr Gln
                165                 170                 175

Gln Thr Asp Glu Ala Asn Lys Ser Ile Trp Thr Gly Ser Ser Cys Thr
            180                 185                 190

Val Lys Val Cys Pro Leu Asn Thr Gln Thr Leu Gly Ile Gly Cys Leu
        195                 200                 205

Ile Thr Asn Pro Asp Thr Phe Glu Thr Val Ala Thr Met Glu Lys Leu
    210                 215                 220

Val Ile Thr Asp Val Val Asp Gly Val Asn His Lys Leu Asn Val Thr
225                 230                 235                 240

Thr Ala Thr Cys Thr Ile Arg Asn Cys Lys Lys Leu Gly Pro Arg Glu
            245                 250                 255

Asn Val Ala Val Ile Gln Val Gly Gly Ala Asn Ile Leu Asp Ile Thr
        260                 265                 270

Ala Asp Pro Thr Thr Thr Pro Gln Thr Glu Thr Met Met Arg Ile Asn
    275                 280                 285

Trp Lys Lys Trp Trp Gln Val Phe Tyr Thr Val Val Asp Tyr Val Asn
    290                 295                 300

Gln Ile Ile Gln Thr Met Ser Lys Arg Ser Thr Ser Leu Asn Ser Ser
305                 310                 315                 320

Ala Phe Tyr Tyr Arg Val
            325

(2) INFORMATION FOR SEQ ID NO:23:

(i) SEQUENCE CHARACTERISTICS:
        (A) LENGTH: 326 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:23:

Met Tyr Gly Ile Glu Tyr Thr Thr Ile Leu Ile Phe Leu Thr Ser Ile
1               5                   10                  15

Thr Leu Leu Asn Tyr Ile Leu Lys Ser Ile Thr Arg Ile Met Asp Tyr
            20                  25                  30

Ile Ile Tyr Arg Phe Leu Leu Ile Val Val Ile Leu Ala Thr Ile Ile
        35                  40                  45

Asn Ala Gln Asn Tyr Gly Val Asn Leu Pro Ile Thr Gly Ser Met Asp
    50                  55                  60

Thr Ala Tyr Ala Asp Ser Thr Gln Ser Glu Pro Phe Leu Thr Ser Thr
65                  70                  75                  80

Leu Cys Leu Tyr Tyr Pro Val Glu Ala Ser Asn Glu Ile Ala Asp Thr
            85                  90                  95

Glu Trp Lys Asp Thr Leu Ser Gln Leu Phe Leu Thr Lys Gly Trp Pro
                100                 105                 110

Thr Gly Ser Val Tyr Leu Lys Glu Tyr Ala Asp Ile Ala Ala Phe Ser

|   |   |   |   | 115 |   |   |   |   | 120 |   |   |   |   | 125 |   |   |   |
|---|---|---|---|---|---|---|---|---|---|---|---|---|---|---|---|---|---|

Val Glu Pro Gln Leu Tyr Cys Asp Tyr Asn Leu Val Leu Met Lys Tyr
130                     135                 140

Asp Ser Thr Gln Glu Leu Asp Met Ser Glu Leu Ala Asp Leu Ile Leu
145                 150                 155                 160

Asn Glu Trp Leu Cys Asn Pro Met Asp Ile Thr Leu Tyr Tyr Tyr Gln
                    165                 170                 175

Gln Thr Asp Glu Ala Asn Lys Ser Ile Trp Thr Gly Ser Ser Cys Thr
                180                 185                 190

Val Lys Val Cys Pro Leu Asn Thr Gln Thr Leu Gly Ile Gly Cys Leu
            195                 200                 205

Ile Thr Asn Pro Asp Thr Phe Glu Thr Val Ala Thr Met Glu Lys Leu
210                     215                 220

Val Ile Thr Asp Val Val Asp Gly Val Asn His Lys Leu Asn Val Thr
225                 230                 235                 240

Thr Ala Thr Cys Thr Ile Arg Asn Cys Lys Lys Leu Gly Pro Arg Glu
                245                 250                 255

Asn Val Ala Val Ile Gln Val Gly Gly Ala Asn Ile Leu Asp Ile Thr
            260                 265                 270

Ala Asp Pro Thr Thr Thr Pro Gln Thr Glu Thr Met Met Arg Ile Asn
            275                 280                 285

Trp Lys Lys Trp Trp Gln Val Phe Tyr Thr Val Val Asp Tyr Val Asn
    290                 295                 300

Gln Ile Ile Gln Thr Met Ser Lys Arg Ser Thr Ser Leu Asn Ser Ser
305                 310                 315                 320

Ala Phe Tyr Tyr Arg Val
                325

( 2 ) INFORMATION FOR SEQ ID NO:24:

( i ) SEQUENCE CHARACTERISTICS:
        ( A ) LENGTH: 326 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:24:

Met Tyr Gly Ile Glu Tyr Thr Thr Val Leu Thr Phe Leu Ile Ser Thr
1               5                   10                  15

Ile Leu Leu Asn Tyr Ile Leu Lys Ser Leu Thr Arg Ile Met Asp Phe
                20                  25                  30

Ile Ile Tyr Arg Phe Leu Phe Ile Ile Val Ile Leu Ser Pro Phe Leu
            35                  40                  45

Arg Ala Gln Asn Tyr Gly Ile Asn Leu Pro Ile Ala Gly Ser Met Asp
    50                  55                  60

Thr Ala Tyr Ala Asn Ser Thr Gln Glu Glu Pro Phe Leu Thr Ser Thr
65                  70                  75                  80

Leu Cys Leu Tyr Tyr Pro Thr Glu Ala Ala Thr Glu Ile Asn Asp Asn
                85                  90                  95

Ser Trp Lys Asp Thr Leu Ser Gln Leu Phe Leu Thr Lys Gly Trp Pro
            100                 105                 110

Thr Glu Ser Val Tyr Phe Lys Glu Tyr Thr Asn Ile Ala Ser Phe Ser
            115                 120                 125

Val Asp Pro Gln Leu Tyr Cys Asp Tyr Asn Val Val Leu Met Lys Tyr
            130                 135                 140

Asp Ala Thr Leu Gln Leu Asp Met Ser Glu Leu Ala Asp Leu Ile Leu

|     | 145 |     |     |     | 150 |     |     |     |     | 155 |     |     |     |     | 160 |
| --- | --- | --- | --- | --- | --- | --- | --- | --- | --- | --- | --- | --- | --- | --- | --- |
| Asn | Glu | Trp | Leu | Cys | Asn | Pro | Met | Asp | Ile | Thr | Leu | Tyr | Tyr | Tyr | Gln |
|     |     |     |     | 165 |     |     |     |     | 170 |     |     |     | 175 |     |     |
| Gln | Thr | Asp | Glu | Ala | Asn | Lys | Trp | Ile | Ser | Met | Gly | Ser | Ser | Cys | Thr |
|     |     |     | 180 |     |     |     |     | 185 |     |     |     | 190 |     |     |     |
| Ile | Lys | Val | Cys | Pro | Leu | Asn | Thr | Gln | Thr | Leu | Gly | Ile | Gly | Cys | Leu |
|     |     | 195 |     |     |     |     | 200 |     |     |     |     | 205 |     |     |     |
| Thr | Thr | Asp | Ala | Thr | Thr | Phe | Glu | Glu | Val | Pro | Thr | Ala | Glu | Lys | Leu |
|     | 210 |     |     |     |     | 215 |     |     |     |     | 220 |     |     |     |     |
| Val | Ile | Thr | Asp | Val | Val | Asp | Gly | Val | Asn | His | Lys | Leu | Asp | Val | Thr |
| 225 |     |     |     |     | 230 |     |     |     |     | 235 |     |     |     |     | 240 |
| Thr | Ala | Thr | Cys | Thr | Ile | Arg | Asn | Cys | Lys | Lys | Leu | Gly | Pro | Arg | Glu |
|     |     |     |     | 245 |     |     |     |     | 250 |     |     |     |     | 255 |     |
| Asn | Val | Ala | Val | Ile | Gln | Val | Gly | Gly | Ser | Asp | Ile | Leu | Asp | Ile | Thr |
|     |     |     | 260 |     |     |     |     | 265 |     |     |     |     | 270 |     |     |
| Ala | Asp | Pro | Thr | Thr | Ala | Pro | Gln | Thr | Glu | Arg | Met | Met | Arg | Ile | Asn |
|     |     | 275 |     |     |     |     | 280 |     |     |     |     | 285 |     |     |     |
| Trp | Lys | Lys | Trp | Trp | Gln | Val | Phe | Tyr | Thr | Val | Val | Asp | Tyr | Val | Asp |
|     | 290 |     |     |     |     | 295 |     |     |     |     | 300 |     |     |     |     |
| Gln | Ile | Ile | Gln | Val | Met | Ser | Lys | Arg | Ser | Arg | Ser | Leu | Asn | Ser | Ala |
| 305 |     |     |     |     | 310 |     |     |     |     | 315 |     |     |     |     | 320 |
| Ala | Phe | Tyr | Tyr | Arg | Val |     |     |     |     |     |     |     |     |     |     |
|     |     |     |     | 325 |     |     |     |     |     |     |     |     |     |     |     |

( 2 ) INFORMATION FOR SEQ ID NO:25:

( i ) SEQUENCE CHARACTERISTICS:
        ( A ) LENGTH: 326 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:25:

| Met | Tyr | Gly | Ile | Glu | Tyr | Thr | Thr | Val | Leu | Thr | Phe | Leu | Ile | Ser | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Ile | Leu | Leu | Asn | Tyr | Ile | Leu | Lys | Ser | Leu | Thr | Arg | Met | Met | Asp | Cys |
|     |     |     | 20  |     |     |     |     | 25  |     |     |     |     | 30  |     |     |
| Ile | Ile | Tyr | Arg | Phe | Leu | Phe | Ile | Val | Val | Ile | Leu | Ser | Pro | Leu | Leu |
|     |     |     | 35  |     |     |     |     | 40  |     |     |     |     | 45  |     |     |
| Lys | Ala | Gln | Asn | Tyr | Gly | Ile | Asn | Leu | Pro | Ile | Thr | Gly | Ser | Met | Asp |
|     | 50  |     |     |     |     | 55  |     |     |     |     | 60  |     |     |     |     |
| Thr | Ala | Tyr | Ala | Asn | Ser | Thr | Gln | Glu | Glu | Thr | Phe | Leu | Thr | Ser | Thr |
| 65  |     |     |     |     | 70  |     |     |     |     | 75  |     |     |     |     | 80  |
| Leu | Cys | Leu | Tyr | Tyr | Pro | Thr | Glu | Ala | Ala | Thr | Glu | Ile | Asn | Asp | Asn |
|     |     |     |     | 85  |     |     |     |     | 90  |     |     |     |     | 95  |     |
| Ser | Trp | Lys | Asp | Thr | Leu | Ser | Gln | Leu | Phe | Leu | Thr | Lys | Gly | Trp | Pro |
|     |     |     | 100 |     |     |     |     | 105 |     |     |     |     | 110 |     |     |
| Thr | Gly | Ser | Val | Tyr | Phe | Lys | Glu | Tyr | Thr | Asp | Ile | Ala | Ser | Phe | Ser |
|     |     |     | 115 |     |     |     |     | 120 |     |     |     |     | 125 |     |     |
| Val | Asp | Pro | Gln | Leu | Tyr | Cys | Asp | Tyr | Asn | Val | Val | Leu | Met | Lys | Tyr |
|     |     | 130 |     |     |     |     | 135 |     |     |     |     | 140 |     |     |     |
| Asp | Ala | Thr | Leu | Gln | Leu | Asp | Met | Ser | Glu | Leu | Ala | Asp | Leu | Ile | Leu |
| 145 |     |     |     |     | 150 |     |     |     |     | 155 |     |     |     |     | 160 |
| Asn | Glu | Trp | Leu | Cys | Asn | Pro | Met | Asp | Ile | Ala | Leu | Tyr | Tyr | Tyr | Gln |
|     |     |     |     | 165 |     |     |     |     | 170 |     |     |     | 175 |     |     |
| Gln | Thr | Asp | Glu | Ala | Asn | Lys | Trp | Ile | Ser | Met | Gly | Ser | Ser | Cys | Thr |

```
                    180                       185                       190
Ile Lys Val Cys Pro Leu Asn Thr Gln Thr Leu Gly Ile Gly Cys Leu
        195                       200                       205

Thr Thr Asp Thr Ala Thr Phe Glu Glu Val Ala Thr Ala Glu Lys Leu
    210                       215                       220

Val Ile Thr Asp Val Val Asp Gly Val Asn His Lys Leu Asp Val Thr
225                       230                       235                       240

Thr Ala Thr Cys Thr Ile Arg Asn Cys Lys Lys Leu Gly Pro Arg Glu
                245                       250                       255

Asn Val Ala Val Ile Gln Val Gly Gly Ser Asp Val Leu Asp Ile Thr
                260                       265                       270

Ala Asp Pro Thr Thr Ala Pro Gln Thr Glu Arg Met Met Arg Ile Asn
            275                       280                       285

Trp Lys Lys Trp Trp Gln Val Phe Tyr Thr Val Val Asp Tyr Val Asn
    290                       295                       300

Gln Ile Ile Gln Ala Met Ser Lys Arg Ser Arg Ser Leu Asn Ser Ala
305                       310                       315                       320

Ala Phe Tyr Asn Arg Ile
                325
```

( 2 ) INFORMATION FOR SEQ ID NO:26:

( i ) SEQUENCE CHARACTERISTICS:
 ( A ) LENGTH: 326 amino acids
 ( B ) TYPE: amino acid
 ( C ) STRANDEDNESS: unknown
 ( D ) TOPOLOGY: unknown ( i i ) MOLECULE TYPE: protein ( x i ) SEQUENCE DESCRIPTION: SEQ ID NO:26:

```
Met Tyr Gly Ile Glu Tyr Thr Thr Val Leu Thr Phe Leu Ile Ser Leu
1               5                       10                      15

Val Phe Val Asn Tyr Ile Leu Lys Ser Val Thr Arg Thr Met Asp Phe
                20                      25                      30

Ile Ile Tyr Arg Phe Leu Leu Val Ile Val Val Leu Ala Pro Leu Ile
            35                      40                      45

Lys Ala Gln Asn Tyr Gly Ile Asn Leu Pro Ile Thr Gly Ser Met Asp
    50                      55                      60

Thr Pro Tyr Met Asn Ser Thr Thr Ser Glu Thr Phe Leu Thr Ser Thr
65                      70                      75                      80

Leu Cys Leu Tyr Tyr Pro Asn Glu Ala Ala Thr Glu Ile Ala Asp Thr
                85                      90                      95

Lys Trp Thr Glu Thr Leu Ser Gln Leu Phe Leu Thr Lys Gly Trp Pro
            100                     105                     110

Thr Gly Ser Val Tyr Phe Lys Gly Tyr Ala Asp Ile Ala Ser Phe Ser
        115                     120                     125

Val Glu Pro Gln Leu Tyr Cys Asp Tyr Asn Ile Val Leu Met Lys Tyr
    130                     135                     140

Asp Gly Asn Leu Gln Leu Asp Met Ser Glu Leu Ala Gly Leu Ile Leu
145                     150                     155                     160

Asn Glu Trp Leu Cys Asn Pro Met Asp Ile Met Leu Tyr Tyr Tyr Gln
                165                     170                     175

Gln Thr Asp Glu Ala Asn Lys Trp Ile Ser Met Gly Thr Ser Cys Thr
            180                     185                     190

Ile Lys Val Cys Pro Leu Asn Thr Gln Thr Leu Gly Ile Gly Cys Ser
        195                     200                     205

Thr Thr Asp Ile Asn Ser Phe Glu Thr Val Ala Asn Ala Glu Lys Leu
```

|           |           |           |           | 210       |           |           |           |           | 215       |           |           |           |           | 220       |           |           |           |           |
|-----------|-----------|-----------|-----------|-----------|-----------|-----------|-----------|-----------|-----------|-----------|-----------|-----------|-----------|-----------|-----------|-----------|-----------|-----------|
| Ala<br>225 | Ile | Thr | Asp | Val | Val<br>230 | Asp | Gly | Val | Asn | His<br>235 | Lys | Leu | Asp | Val | Thr<br>240 |
| Thr | Ser | Thr | Cys | Thr<br>245 | Ile | Arg | Asn | Cys | Lys<br>250 | Lys | Leu | Gly | Pro | Arg<br>255 | Glu |
| Asn | Val | Ala | Val<br>260 | Ile | Gln | Val | Gly | Gly<br>265 | Pro | Asn | Ile | Leu | Asp<br>270 | Ile | Thr |
| Ala | Asp | Pro<br>275 | Thr | Thr | Ala | Pro | Gln<br>280 | Thr | Glu | Arg | Met | Met<br>285 | Arg | Ile | Asn |
| Trp | Lys<br>290 | Arg | Trp | Trp | Gln | Val<br>295 | Phe | Tyr | Thr | Ile | Val<br>300 | Asp | Tyr | Val | Asn |
| Gln<br>305 | Ile | Val | Gln | Val | Met<br>310 | Ser | Lys | Arg | Ser | Arg<br>315 | Ser | Leu | Asp | Ser | Ala<br>320 |
| Ala | Phe | Tyr | Tyr | Arg<br>325 | Val |

( 2 ) INFORMATION FOR SEQ ID NO:27:

( i ) SEQUENCE CHARACTERISTICS:
        ( A ) LENGTH: 326 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:27:

| Met<br>1 | Tyr | Gly | Ile | Glu<br>5 | Tyr | Thr | Thr | Ile | Leu<br>10 | Ile | Phe | Leu | Ile | Ser<br>15 | Ile |
| Ile | Leu | Leu | Asn<br>20 | Tyr | Ile | Leu | Lys | Ser<br>25 | Val | Thr | Arg | Ile | Met<br>30 | Asp | Tyr |
| Ile | Ile | Tyr<br>35 | Arg | Phe | Leu | Leu | Ile<br>40 | Thr | Val | Ala | Leu | Phe<br>45 | Ala | Leu | Thr |
| Arg | Ala<br>50 | Gln | Asn | Tyr | Gly | Leu<br>55 | Asn | Leu | Pro | Ile | Thr<br>60 | Gly | Ser | Met | Asp |
| Ala<br>65 | Val | Tyr | Thr | Asn | Ser<br>70 | Thr | Gln | Glu | Glu | Val<br>75 | Phe | Leu | Thr | Ser | Thr<br>80 |
| Leu | Cys | Leu | Tyr | Tyr<br>85 | Pro | Thr | Glu | Ala | Ser<br>90 | Thr | Gln | Ile | Asn | Asp<br>95 | Gly |
| Asp | Trp | Lys | Asp<br>100 | Ser | Leu | Ser | Gln | Met<br>105 | Phe | Leu | Thr | Lys | Gly<br>110 | Trp | Pro |
| Thr | Gly | Ser<br>115 | Val | Tyr | Phe | Lys | Glu<br>120 | Tyr | Ser | Asn | Ile | Val<br>125 | Asp | Phe | Ser |
| Val | Asp<br>130 | Pro | Gln | Leu | Tyr | Cys<br>135 | Asp | Tyr | Asn | Leu | Val<br>140 | Leu | Met | Lys | Tyr |
| Asp<br>145 | Gln | Ser | Leu | Lys | Leu<br>150 | Asp | Met | Ser | Glu | Leu<br>155 | Ala | Asp | Leu | Ile | Leu<br>160 |
| Asn | Glu | Trp | Leu | Cys<br>165 | Asn | Pro | Met | Asp | Val<br>170 | Thr | Leu | Tyr | Tyr | Tyr<br>175 | Gln |
| Gln | Ser | Gly | Glu | Ser<br>180 | Asn | Lys | Trp | Ile | Ser<br>185 | Met | Gly | Ser | Ser | Cys<br>190 | Thr |
| Val | Lys | Val<br>195 | Cys | Pro | Leu | Asn | Thr<br>200 | Gln | Thr | Leu | Gly | Ile<br>205 | Gly | Cys | Gln |
| Thr | Thr<br>210 | Asn | Val | Asp | Ser | Phe<br>215 | Glu | Met | Ile | Ala | Glu<br>220 | Asn | Glu | Lys | Leu |
| Ala<br>225 | Ile | Val | Asp | Val | Val<br>230 | Asp | Gly | Ile | Asn | His<br>235 | Lys | Ile | Asn | Leu | Thr<br>240 |
| Thr | Thr | Thr | Cys | Thr<br>245 | Ile | Arg | Asn | Cys | Lys<br>250 | Lys | Leu | Gly | Pro | Arg<br>255 | Glu |

|     |     |     |     | 245 |     |     |     |     | 250 |     |     |     |     | 255 |     |
| --- | --- | --- | --- | --- | --- | --- | --- | --- | --- | --- | --- | --- | --- | --- | --- |
| Asn | Val | Ala | Val | Ile | Gln | Val | Gly | Gly | Ser | Asn | Val | Leu | Asp | Ile | Thr |
|     |     |     | 260 |     |     |     | 265 |     |     |     |     | 270 |     |     |     |
| Ala | Asp | Pro | Thr | Thr | Asn | Pro | Gln | Thr | Glu | Arg | Met | Met | Arg | Val | Asn |
|     |     | 275 |     |     |     | 280 |     |     |     |     | 285 |     |     |     |     |
| Trp | Lys | Lys | Trp | Trp | Gln | Val | Phe | Tyr | Thr | Ile | Val | Asp | Tyr | Ile | Asn |
|     | 290 |     |     |     | 295 |     |     |     |     | 300 |     |     |     |     |     |
| Gln | Ile | Val | Gln | Val | Met | Ser | Lys | Arg | Ser | Arg | Ser | Leu | Asn | Ser | Ala |
| 305 |     |     |     |     | 310 |     |     |     |     | 315 |     |     |     |     | 320 |
| Ala | Phe | Tyr | Tyr | Arg | Val |     |     |     |     |     |     |     |     |     |     |
|     |     |     |     | 325 |     |     |     |     |     |     |     |     |     |     |     |

( 2 ) INFORMATION FOR SEQ ID NO:28:

( i ) SEQUENCE CHARACTERISTICS:
    ( A ) LENGTH: 326 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:28:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Tyr | Gly | Ile | Glu | Tyr | Thr | Thr | Val | Leu | Leu | Tyr | Leu | Ile | Ser | Phe |
| 1   |     |     |     | 5   |     |     |     |     | 10  |     |     |     |     | 15  |     |
| Val | Leu | Met | Ser | Tyr | Ile | Leu | Lys | Thr | Ile | Thr | Lys | Met | Met | Asp | Tyr |
|     |     |     | 20  |     |     |     |     | 25  |     |     |     |     | 30  |     |     |
| Ile | Ile | Tyr | Arg | Ile | Thr | Phe | Ile | Ile | Val | Val | Leu | Ser | Val | Leu | Ser |
|     |     |     | 35  |     |     |     |     | 40  |     |     |     |     | 45  |     |     |
| Asn | Ala | Gln | Asn | Tyr | Gly | Ile | Asn | Leu | Pro | Ile | Thr | Gly | Ser | Met | Asp |
|     | 50  |     |     |     |     | 55  |     |     |     |     | 60  |     |     |     |     |
| Thr | Ala | Tyr | Ala | Asn | Ser | Thr | Gln | Asp | Asn | Asn | Phe | Leu | Ser | Ser | Thr |
| 65  |     |     |     |     | 70  |     |     |     |     | 75  |     |     |     |     | 80  |
| Leu | Cys | Leu | Tyr | Tyr | Pro | Ser | Glu | Ala | Pro | Thr | Gln | Ile | Asn | Asp | Asn |
|     |     |     |     | 85  |     |     |     |     | 90  |     |     |     |     | 95  |     |
| Glu | Trp | Lys | Asp | Thr | Leu | Ser | Gln | Leu | Phe | Leu | Thr | Lys | Gly | Trp | Pro |
|     |     |     | 100 |     |     |     |     | 105 |     |     |     |     | 110 |     |     |
| Thr | Gly | Ser | Val | Tyr | Phe | Asn | Glu | Tyr | Ser | Asn | Val | Leu | Glu | Phe | Ser |
|     |     | 115 |     |     |     |     | 120 |     |     |     |     | 125 |     |     |     |
| Ile | Asp | Pro | Lys | Leu | His | Cys | Asp | Tyr | Asn | Ile | Val | Leu | Ile | Arg | Phe |
|     | 130 |     |     |     |     | 135 |     |     |     |     | 140 |     |     |     |     |
| Ala | Ser | Gly | Glu | Glu | Leu | Asp | Ile | Ser | Glu | Leu | Ala | Asp | Leu | Ile | Leu |
| 145 |     |     |     |     | 150 |     |     |     |     | 155 |     |     |     |     | 160 |
| Asn | Glu | Trp | Leu | Cys | Asn | Pro | Met | Asp | Ile | Thr | Leu | Tyr | Tyr | Tyr | Gln |
|     |     |     |     | 165 |     |     |     |     | 170 |     |     |     |     | 175 |     |
| Gln | Thr | Gly | Glu | Ala | Asn | Lys | Trp | Ile | Ser | Met | Gly | Ser | Ser | Cys | Thr |
|     |     |     | 180 |     |     |     |     | 185 |     |     |     |     | 190 |     |     |
| Val | Lys | Val | Cys | Pro | Leu | Asn | Thr | Gln | Thr | Leu | Gly | Ile | Gly | Cys | Gln |
|     |     | 195 |     |     |     |     | 200 |     |     |     |     | 205 |     |     |     |
| Thr | Thr | Asn | Thr | Ala | Thr | Phe | Glu | Thr | Val | Ala | Asp | Ser | Glu | Lys | Leu |
|     | 210 |     |     |     |     | 215 |     |     |     |     | 220 |     |     |     |     |
| Ala | Ile | Val | Asp | Val | Val | Asp | Ser | Val | Asn | His | Lys | Leu | Asp | Val | Thr |
| 225 |     |     |     |     | 230 |     |     |     |     | 235 |     |     |     |     | 240 |
| Ser | Thr | Thr | Cys | Thr | Ile | Arg | Asn | Cys | Asn | Lys | Leu | Gly | Pro | Arg | Glu |
|     |     |     |     | 245 |     |     |     |     | 250 |     |     |     |     | 255 |     |
| Asn | Val | Ala | Ile | Ile | Gln | Val | Gly | Gly | Ser | Asn | Ile | Leu | Asp | Ile | Thr |
|     |     |     | 260 |     |     |     |     | 265 |     |     |     |     | 270 |     |     |
| Ala | Asn | Pro | Thr | Thr | Ser | Pro | Gln | Thr | Glu | Arg | Met | Met | Arg | Val | Asn |

```
              275                         280                         285

Trp  Lys  Lys  Trp  Trp  Gln  Val  Phe  Tyr  Thr  Val  Val  Asp  Tyr  Ile  Asn
         290                         295                         300

Gln  Ile  Val  Gln  Val  Met  Ser  Lys  Arg  Ser  Arg  Ser  Leu  Asp  Ser  Ser
    305                         310                         315                         320

Ser  Phe  Tyr  Tyr  Arg  Val
                        325
```

( 2 ) INFORMATION FOR SEQ ID NO:29:

( i ) SEQUENCE CHARACTERISTICS:
        ( A ) LENGTH: 317 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:29:

```
    Met  Ala  Glu  Leu  Ala  Cys  Phe  Cys  Tyr  Pro  His  Leu  Glu  Asn  Asp  Ser
    1                   5                        10                          15

Tyr  Lys  Phe  Ile  Pro  Phe  Asn  Asn  Leu  Ala  Ile  Lys  Cys  Met  Leu  Thr
                   20                        25                        30

Ala  Lys  Val  Asp  Arg  Lys  Asp  Gln  Asp  Lys  Phe  Tyr  Asn  Ser  Ile  Ile
              35                        40                        45

Tyr  Gly  Ile  Ala  Pro  Pro  Pro  Gln  Phe  Lys  Lys  Arg  Tyr  Asn  Thr  Asn
         50                        55                        60

Asp  Asn  Ser  Arg  Gly  Met  Asn  Tyr  Glu  Thr  Ser  Met  Phe  Asn  Lys  Val
    65                        70                        75                        80

Ala  Val  Leu  Ile  Cys  Glu  Ala  Leu  Asn  Ser  Ile  Lys  Val  Thr  Gln  Ser
                        85                        90                        95

Asp  Val  Ala  Asn  Val  Leu  Ser  Arg  Val  Val  Ser  Val  Arg  His  Leu  Glu
                   100                       105                       110

Asn  Leu  Val  Leu  Arg  Arg  Glu  Asn  His  Gln  Asp  Val  Leu  Phe  His  Ser
                   115                       120                       125

Lys  Glu  Leu  Leu  Leu  Lys  Ser  Val  Leu  Ile  Ala  Ile  Gly  His  Ser  Lys
         130                       135                       140

Glu  Ile  Glu  Thr  Thr  Ala  Thr  Ala  Glu  Gly  Gly  Glu  Ile  Val  Phe  Gln
    145                       150                       155                       160

Asn  Ala  Ala  Phe  Thr  Met  Trp  Lys  Leu  Thr  Tyr  Leu  Glu  His  Lys  Leu
                        165                       170                       175

Met  Pro  Ile  Leu  Asp  Gln  Asn  Phe  Ile  Glu  Tyr  Lys  Ile  Thr  Val  Asn
                   180                       185                       190

Glu  Asp  Lys  Pro  Ile  Ser  Glu  Ser  His  Val  Lys  Glu  Leu  Ile  Ala  Glu
              195                       200                       205

Leu  Arg  Trp  Gln  Tyr  Asn  Lys  Phe  Ala  Val  Ile  Thr  His  Gly  Lys  Gly
         210                       215                       220

His  Tyr  Arg  Val  Val  Lys  Tyr  Ser  Ser  Val  Ala  Asn  His  Ala  Asp  Arg
    225                       230                       235                       240

Val  Tyr  Ala  Thr  Phe  Lys  Ser  Asn  Asn  Lys  Asn  Gly  Asn  Val  Leu  Glu
                        245                       250                       255

Phe  Asn  Leu  Leu  Asp  Gln  Arg  Ile  Ile  Trp  Gln  Asn  Trp  Tyr  Ala  Phe
                   260                       265                       270

Thr  Ser  Ser  Met  Lys  Gln  Gly  Asn  Thr  Leu  Asp  Ile  Cys  Lys  Lys  Leu
                   275                       280                       285

Leu  Phe  Gln  Lys  Met  Lys  Arg  Glu  Ser  Asn  Pro  Phe  Lys  Gly  Leu  Ser
         290                       295                       300

Thr  Asp  Arg  Lys  Met  Asp  Glu  Val  Ser  Gln  Ile  Gly  Ile
```

| 305 | 310 | 315 |
|---|---|---|

(2) INFORMATION FOR SEQ ID NO:30:

(i) SEQUENCE CHARACTERISTICS:
        (A) LENGTH: 317 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:30:

```
Met Ala Glu Leu Ala Cys Phe Cys Tyr Pro His Leu Glu Lys Asp Ser
 1               5                  10                  15
Tyr Lys Phe Ile Pro Phe Asn Ser Leu Ala Ile Lys Cys Met Leu Thr
             20                  25                  30
Ala Lys Val Asp Lys Lys Asp Gln Asp Lys Phe Tyr Asn Ser Ile Val
         35                  40                          45
Tyr Gly Ile Ala Pro Pro Pro Gln Phe Lys Lys Arg Tyr Asn Thr Asn
     50                  55                      60
Asp Asn Ser Arg Gly Met Asn Phe Glu Thr Ser Met Phe Asn Lys Val
 65                  70                  75                  80
Ala Ile Leu Ile Cys Glu Ala Leu Asn Ser Ile Lys Val Thr Gln Ser
                 85                  90                  95
Asp Val Ala Asn Val Leu Ser Arg Val Val Ser Val Arg His Leu Glu
                100                 105                 110
Asn Leu Val Leu Arg Lys Glu Asn His Gln Asp Val Leu Phe His Ser
             115                 120                 125
Lys Glu Leu Leu Leu Lys Ala Val Leu Ile Ala Ile Gly Gln Ser Lys
    130                 135                 140
Glu Ile Glu Thr Thr Ala Thr Ala Glu Gly Gly Glu Ile Val Phe Gln
145                 150                 155                 160
Asn Ala Ala Phe Thr Met Trp Lys Leu Thr Tyr Leu Asp His Lys Leu
                165                 170                 175
Met Pro Ile Leu Asp Gln Asn Phe Ile Glu Tyr Lys Ile Thr Leu Asn
             180                 185                 190
Glu Asp Lys Pro Ile Ser Asp Ala Cys Val Lys Glu Leu Val Ala Glu
    195                 200                 205
Leu Arg Trp Gln Tyr Asn Arg Phe Ala Val Ile Thr His Gly Lys Gly
    210                 215                 220
His Tyr Arg Val Val Lys Tyr Ser Ser Val Ala Asn His Ala Asp Arg
225                 230                 235                 240
Val Phe Ala Thr Tyr Lys Asn Asn Ala Lys Ser Gly Asn Val Thr Asp
                245                 250                 255
Phe Asn Leu Leu Asp Gln Arg Ile Ile Trp Gln Asn Trp Tyr Ala Phe
             260                 265                 270
Thr Ser Ser Met Lys Gln Gly Asn Thr Leu Asp Val Cys Lys Lys Leu
        275                 280                 285
Leu Phe Gln Lys Met Lys Gln Glu Lys Asn Pro Phe Lys Gly Leu Ser
    290                 295                 300
Thr Asp Arg Lys Met Asp Glu Val Ser His Val Gly Ile
305                 310                 315
```

As can be seen, vaccination with the viral particles, VP4 alone, and mixed crude cell lysates, provided protection to challenged neonatal mice.

Thus, viral particle assemblies, vaccine compositions containing these assemblies, and methods of treating and preventing rotaviral disease in a vertebrate subject are disclosed. Although preferred embodiments of the subject invention have been described in some detail, it is understood that obvious variations can be made with-

We claim:

1. A viral particle assembly capable of eliciting a protective immunological response in a vertebrate subject, said viral particle assembly consisting of:
   (a) an inner capsid protein, VP6; and
   (b) outer capsid proteins VP4 and VP7.

2. A viral particle assembly capable of eliciting an immunological response in a vertebrate subject, said viral particle assembly consisting of VP6 assembled with VP4 and VP7.

3. A vaccine composition comprising a pharmaceutically acceptable vehicle and the viral particle assembly of claim 2.

4. The vaccine composition of claim 3 further comprising one or more unassembled proteins selected from the group consisting of VP6, VP4 and VP7.

5. The vaccine composition of claim 4 wherein said unassembled protein is provided in a cell lysate.

6. The vaccine composition of claim 3 further comprising an adjuvant.

7. A method of preventing rotaviral disease in a vertebrate subject comprising administering to said subject a therapeutically effective amount of a vaccine composition according to claim 3.

8. A method of preventing rotaviral disease in a vertebrate subject comprising administering to said subject a therapeutically effective amount of a vaccine composition according to claim 4.